(12) United States Patent
Kirsch et al.

(10) Patent No.: US 11,667,845 B2
(45) Date of Patent: Jun. 6, 2023

(54) LIQUID CRYSTALLINE MEDIUM

(71) Applicant: MERCK PATENT GMBH, Darmstadt (DE)

(72) Inventors: Peer Kirsch, Seeheim-Jugenheim (DE); Michael Junge, Pfungstadt (DE); Ursula Patwal, Reinheim (DE); Ewa Ptak, Weiterstadt (DE); Theresa Lorenz, Weiterstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 2 days.

(21) Appl. No.: 16/973,735

(22) PCT Filed: Jun. 7, 2019

(86) PCT No.: PCT/EP2019/064976
§ 371 (c)(1),
(2) Date: Dec. 9, 2020

(87) PCT Pub. No.: WO2019/238567
PCT Pub. Date: Dec. 19, 2019

(65) Prior Publication Data
US 2021/0238481 A1    Aug. 5, 2021

(30) Foreign Application Priority Data
Jun. 11, 2018 (EP) .................................... 18176940

(51) Int. Cl.
| | | |
|---|---|---|
| *G02F 1/1333* | (2006.01) | |
| *C09K 19/60* | (2006.01) | |
| *C07D 519/00* | (2006.01) | |
| *C09K 19/30* | (2006.01) | |
| *C09K 19/04* | (2006.01) | |

(52) U.S. Cl.
CPC .......... *C09K 19/601* (2013.01); *C07D 519/00* (2013.01); *C09K 19/3001* (2013.01); *C09K 19/3003* (2013.01); *C09K 19/3068* (2013.01); *C09K 2019/0466* (2013.01); *C09K 2019/301* (2013.01); *C09K 2019/3004* (2013.01); *C09K 2019/3009* (2013.01); *C09K 2019/3016* (2013.01); *C09K 2019/3019* (2013.01); *C09K 2019/3021* (2013.01); *C09K 2019/3025* (2013.01); *C09K 2019/3071* (2013.01); *C09K 2019/3078* (2013.01)

(58) Field of Classification Search
CPC .............. C09K 19/601; C09K 19/3001; C09K 19/3003; C09K 19/3068; C09K 19/60; C09K 2019/0466; C09K 2019/3004; C09K 2019/3009; C09K 2019/301; C09K 2019/3016; C09K 2019/3019; C09K 2019/3021; C09K 2019/3025; C09K 2019/3071; C09K 2019/3078; C09K 2019/123; C09K 2019/181; C09K 2019/2035; C09K 2019/3027; C09K 2019/3063; C09K 2019/3408; G02F 1/1333; C07D 519/00
See application file for complete search history.

(56) References Cited

U.S. PATENT DOCUMENTS

| | | | |
|---|---|---|---|
| 9,701,905 B2 | 7/2017 | Junge et al. | |
| 10,738,240 B2* | 8/2020 | Kirsch | .................... C09K 19/52 |
| 2018/0335654 A1* | 11/2018 | Kirsch | .................... F24S 50/80 |
| 2019/0153320 A1 | 5/2019 | Kirsch et al. | |

FOREIGN PATENT DOCUMENTS

| | | |
|---|---|---|
| WO | 2014090373 A1 | 6/2014 |
| WO | 2018015320 A1 | 1/2018 |

OTHER PUBLICATIONS

Wang et al., Macromolecules, 2015, vol. 48, pp. 4012-4023 (Year: 2015).*
International Search Report for PCT/EP2019/064976 dated Sep. 18, 2019.
Patal, D.G. et al., "It Takes More Than an Imine: The Role of the Central Atom on the Electron-Accepting Ability of Benzotriazole and Benzothiadiazole Oligomers," Journal of the American Chemical Society, 2012, vol. 134, pp. 2599-2612.

* cited by examiner

*Primary Examiner* — Geraldina Visconti
(74) *Attorney, Agent, or Firm* — Millen White Zelano and Branigan, PC; Csaba Henter

(57) ABSTRACT

The present invention relates to benzotriazole derivatives selected from the group of compounds of formulae Ia, Ib and Ic as defined in claim 1, to mesogenic media comprising the compounds of formulae Ia, Ib and Ic, and to the use of these compounds and mesogenic media in optical, electronic and electro-optical applications, in particular in devices for regulating the passage of energy from an outside space into an inside space, for example in windows.

26 Claims, No Drawings

LIQUID CRYSTALLINE MEDIUM

The present invention relates to benzotriazole derivatives selected from the group of compounds of formulae Ia, Ib and Ic as defined below, to mesogenic media comprising the compounds of formulae Ia, Ib and Ic, and to the use of these compounds and mesogenic media in optical, electronic and electro-optical applications, in particular in devices for regulating the passage of energy from an outside space into an inside space, for example in windows.

Liquid crystals are used in particular as dielectrics in display devices, wherein the optical properties of such materials can be influenced by an applied voltage. Electro-optical devices based on liquid crystals are well known in the art and can be based on various effects. Devices of this type are, for example, cells having dynamic scattering, DAP (deformation of aligned phases) cells, TN cells having a twisted nematic structure, STN ("supertwisted nematic") cells, SBE ("superbirefringence effect") cells, OMI ("optical mode interference") cells and guest-host cells.

Devices based on the guest-host effect were first described by Heilmeier and Zanoni (G. H. Heilmeier et al., Appl. Phys. Lett., 1968, 13, 91f) and have since then found widespread use, principally in liquid crystal (LC) display elements. In a guest-host system, the LC medium comprises one or more dichroic dyes in addition to the liquid crystal. Owing to the directional dependence of the absorption by the dye molecules, the transmissivity of the dye-doped liquid crystal to light can be modulated when the dyes change their alignment together with the liquid crystal.

Besides the use in LC displays, devices of this type are also used as switching elements for regulating the passage of light or energy, as described for example in WO 2009/141295 and WO 2010/118422. For the devices for regulating the passage of energy from an outside space into an inside space, a number of different technical solutions have been proposed.

In one of the possible modes for the devices, a liquid-crystalline medium in combination with one or more dichroic dyes as described above can be used in the switching layer(s). By application of a voltage, a change in the orientational alignment of the dichroic dye molecules can be achieved in these switching layers. Owing to the direction-dependent absorption, a change in the transmissivity of the switching layer can thus be obtained. A corresponding device is described, for example, in WO 2009/141295.

Alternatively, such a change in the transmission behaviour can also be achieved without electrical voltage by a temperature-induced transition from an isotropic state of the liquid-crystalline medium to a liquid-crystalline state, as described, for example, in US 2010/0259698.

WO 2009/141295 and WO 2010/118422 describe liquid-crystalline media for display elements of the guest-host type which comprise cyanobiphenyl derivatives and one or more dichroic dyes. For the same application, U.S. Pat. Nos. 6,033,598 and 5,762,824 describe LC media which, besides one or more dichroic dyes, comprise one or more compounds each consisting of three ring elements which are substituted by one or more fluorine atoms.

Rylene dyes have been described for use in the above-mentioned devices, for example in WO 2009/141295, WO 2013/004677 and WO2014/090373.

Also known are benzobis(thiadiazole) derivatives for various applications, for example for use as organic semi-conductors as described in WO 2015/041026, exemplified by the following structure:

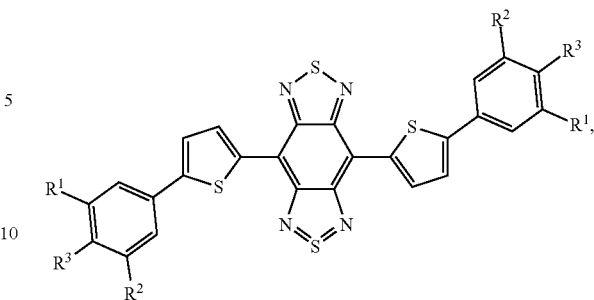

wherein, inter alia, $R^1$ denotes straight chain or branched alkyl and $R^2$ and $R^3$ denote H.

A similar compound with an oxadiazolothiadiazolobenzene central structure of the following formula

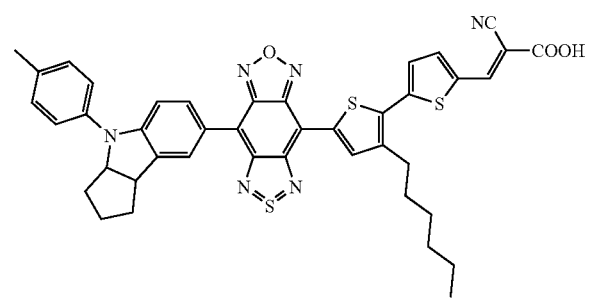 [SMILES: CCCCCCc1cc(-c2c3c(c(-c4ccc5c(c4)C4CCCC4N5c4ccc(C)cc4)c4nonc24)N=S=N3)sc1-c1ccc(/C=C(\C#N)C(=O)O)s1]

is described in M. Li et al., J. Phys. Chem. C 2015, 119, 9782-9790.

WO 2018/015320 describes the use of liquid-crystalline media comprising bis(thiadiazolo)benzene derivatives for use in devices for regulating the passage of energy from an outside space into an inside space.

D. G. Patel et al. in J. Am. Chem. Soc. 2012, 134, 2599-2612 describe electronic and photophysical properties of donor-acceptor-donor oligomers particularly with regard to applications in photonic devices such as dye-sensitized solar cells and show compounds having benzothiadiazole, benzobis(thiadiazole), benzotriazole and benzo(triazole-thiadiazole) moieties.

There is still a need in the art for dichroic dye compounds and media comprising these compounds which give benefits in terms of device performance and reliability.

An object of the present invention is therefore to provide improved compounds which are particularly useful for guest-host type applications and which show favourable lightfastness and a suitably high dichroic ratio together with a favourable solubility in LC media. In particular, it is an object to provide dichroic dyes exhibiting high colour purity and a large extinction coefficient in the VIS and/or NIR region of light while at the same time giving suitable light and temperature stability and only weak or even no discernible fluorescence. It is in particular desired to provide dichroic dyes having a blue colour which exhibit only weak or even no discernible fluorescence. It is furthermore an object to provide improved mesogenic media which comprise these compounds and which exhibit broad and stable LC phase ranges and in particular favourable low-temperature stability and which furthermore can give a suitable high degree of order. It is a further object to provide a stable and reliable switching medium for electro-optical applications which allow a particular beneficial performance in devices for regulating the passage of energy from an outside space into an inside space, in particular in smart switchable windows, e.g. in terms of the stability with respect to direct and prolonged irradiation of sunlight or the aesthetic impression. Further objects of the present invention are immediately evident to the person skilled in the art from the following detailed description.

The objects are solved by the subject-matter defined in the independent claims, while preferred embodiments are set forth in the respective dependent claims and are further described below.

The present invention in particular provides the following items including main aspects, preferred embodiments and particular features, which respectively alone and in combination contribute to solving the above object and eventually provide additional advantages.

A first aspect of the present invention provides a mesogenic medium comprising one or more compounds selected from the group of compounds of formulae Ia, Ib and Ic

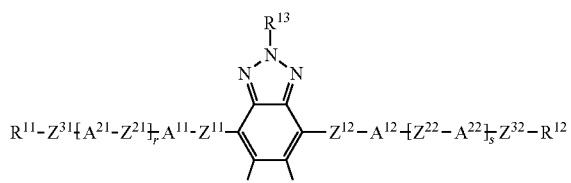

Ia

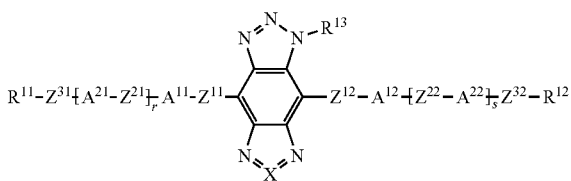

Ib

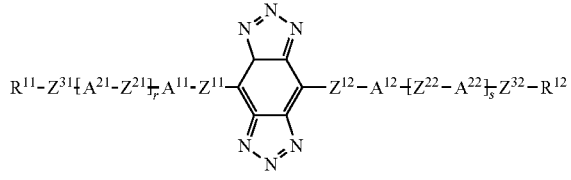

Ic wherein $R^{11}$, $R^{12}$, $R^{13}$ identically or differently, denote H, F, CN, CO, $N(R^z)_2$, $SO_2R^z$,

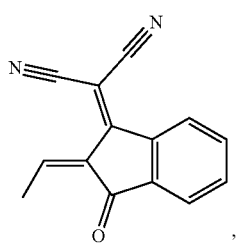

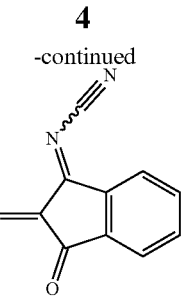

$CH=C(CN)_2$, or straight-chain, branched or cyclic alkyl having 1 to 20 C atoms, in which, in addition, one or more non-adjacent $CH_2$ groups may each be replaced, independently of one another, by $-C(R^z)=C(R^z)-$, $-C\equiv C-$,

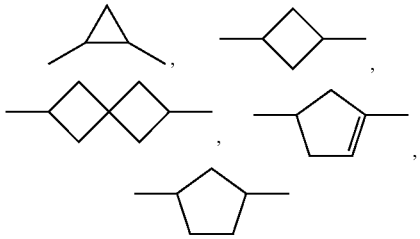

$-N(R^z)-$, $-O-$, $-S-$, $-CO-$, $-CO-O-$, $-O-CO-$ or $-O-CO-O-$ in such a way that O and/or S atoms are not linked directly to one another, and in which, in addition, one or more H atoms may be replaced by F, Cl, Br, I or CN, $R^z$ on each occurrence, identically or differently, denotes H, halogen, straight-chain, branched or cyclic alkyl having 1 to 12 C atoms, in which, in addition, one or more non-adjacent $CH_2$ groups may be replaced by $-O-$, $-S-$, $-CO-$, $-CO-O-$, $-O-CO-$ or $-O-CO-O-$ in such a way that O and/or S atoms are not linked directly to one another, and in which, in addition, one or more H atoms may be replaced by F or Cl, $A^{11}$, $A^{12}$ each, independently of one another, denote an aryl or heteroaryl group, which may be substituted by one or more radicals L, $A^{21}$, $A^{22}$ on each occurrence, identically or differently, denote an aryl or heteroaryl group, which may be substituted by one or more radicals L, or a cyclic alkyl group having 3 to 10 C atoms, in which one or more non-adjacent $CH_2$ groups may be replaced by O, L on each occurrence, identically or differently, denotes F, Cl, CN, OH, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms, X is S, Se or Te, $Z^{11}$, $Z^{12}$ on each occurrence, identically or differently, denote a single bond, $-CR^{x1}=CR^{x2}-$, $-C\equiv C-$, $-C(O)-$, $-CR^{x1}=CR^{x2}-CO-$, $-CO-CR^{x1}=CR^{x2}-$, $-CR^{x1}=CR^{x2}-COO-$, $-COO-CR^{x1}=CR^{x2}-$ or $-N=N-$, $Z^{21}$, $Z^{22}$ on each occurrence, identically or differently, denote a single bond, $-O-$, $-S-$, $-C(O)-$, $-CR^{y1}R^{y2}-$, $-CF_2-$, $-OCF_2-$, $-C(O)-O-$, $-O-C(O)-$, $-O-C(O)-O-$, $-OCH_2-$, $-CH_2O-$, $-SCH_2-$, $-CH_2S-$, $-CF_2S-$, $-SCF_2-$, $-(CH_2)_{n1}-$, $-CF_2CH_2-$, $-CH_2CF_2-$, —$(CF_2)_{n1}$—,  —$CR^{x1}$=$CR^{x2}$—,  —C≡C—, —$CR^{x1}$=$CR^{x2}$—CO—, —CO—$CR^{x1}$=$CR^{x2}$—, —$CR^{x1}$=$CR^{x2}$—COO—, —OCO—$CR^{x1}$=$CR^{x2}$— or —N=N—, $Z^{31}$, $Z^{32}$ on each occurrence, identically or differently, denote a single bond, —O—, —$CF_2O$—, —$OCF_2$—, —$CF_2$—, —$CF_2CF_2$— or —C(O)—, $R^{x1}$, $R^{x2}$ independently of one another, denote H, F, Cl, CN or alkyl having 1 to 12 C atoms, $R^{y1}$ denotes H or alkyl having 1 to 12 C atoms, $R^{y2}$ denotes alkyl having 1 to 12 C atoms, n1 denotes 1, 2, 3 or 4, and r, s independently of one another, denote 0, 1, 2 or 3.

It has surprisingly been found that the compounds of formulae Ia, Ib and Ic can give the desired lightfastness and high dichroic ratio, while at the same time having excellent solubility in mesogenic media. In addition, the compounds exhibit favourable colour purity and large extinction coefficients together with suitable light and temperature stability. The compounds are thus particularly useful for guest-host type applications, wherein the dye-doped mesogenic media can exhibit suitably broad and stable LC phase ranges and in particular favourable low-temperature stability. The mesogenic media according to the invention can thus give benefits in terms of device performance and reliability, in particular in smart switchable windows, e.g. in terms of the stability with respect to direct and prolonged irradiation of sunlight or the aesthetic impression.

In addition, it was found that the compounds not only show favourable solubility in the LC media on their own, but that they can be mixed well together with other dichroic dye compounds in the media. This favourably contributes to improving the capabilities for the provision of tailor-made dye-doped liquid crystal media, especially in terms of giving specific colours or even covering the whole VIS range to achieve a black appearance.

In this respect, the compounds of formulae Ia, Ib and Ic can be chosen and adjusted such to give the desired colour, in particular also blue, while exhibiting only a very weak or even no fluorescence at all.

Another aspect of the invention thus relates to the compounds selected from the group of compounds of formulae Ia, Ib and Ic as described herein above and below.

It has surprisingly been found that the compounds of formulae Ia, Ib and Ic as described herein exhibit excellent combined properties and characteristics, e.g. in terms of the extinction coefficient, stability and solubility, which can give a beneficial performance in optical, electro-optical and electronic applications, and in particular in the use of guest-host applications such as in dimmable smart windows. In particular, the compounds according to the invention have excellent solubility and stability in liquid crystalline media.

Therefore, in a further aspect according to the invention there is provided a device for regulating the passage of energy from an outside space into an inside space, wherein the device contains a switching layer comprising the liquid crystalline medium according to the invention as described herein. In particular, the device can be comprised in a window.

In a further aspect of the invention the compounds and the mesogenic media according to the invention are used in an electro-optical display, a device for regulating the passage of energy from an outside space into an inside space, an electrical semiconductor, an organic field-effect transistor, a printed circuit, a radio frequency identification element, a diode, an organic light-emitting diode, a lighting element, a photovoltaic device, in particular as a sensitizer or semiconductor therein, an optical sensor, an effect pigment, a decorative element or as a dye for colouring polymers, e.g. in the automotive field.

In a further aspect according to the invention there is provided a method for preparing the compounds of formulae Ia, Ib and Ic. In particular, the method gives a facile process with ease of production to obtain the compounds according to the invention.

In particular, favourably and preferably the compound I-SM as defined herein is provided as a precursor and subjected to further chemical reaction.

Without limiting the present invention thereby, in the following the invention is illustrated by the detailed description of the aspects, embodiments and particular features, and particular embodiments are described in more detail.

In the present invention a device for regulating the passage of energy from an outside space into an inside space is preferably taken to mean a device which regulates the passage of energy, in particular light and especially sunlight, through an area which is arranged within a structure of relatively lower energy transmissivity. The structure of lower energy transmissivity can be a wall. The energy can thus for example pass through an open area or in particular a glass area in the wall. The device is thus preferably arranged to be a constituent of a window, for example an insulated glazing unit.

The regulated passage of energy takes place from an outside space, preferably the environment exposed to direct or indirect sunlight radiation, into an inside space, for example a building or a vehicle, or another unit which is substantially sealed off from the environment.

For the purposes of the present invention, the term energy is taken to mean in particular energy by electromagnetic radiation in the UV-A, VIS and NIR region. In particular, it is taken to mean energy by radiation which is not absorbed or is only absorbed to a negligible extent by the materials usually used in windows, for example glass. Herein, the UV-A region is taken to mean the wavelength range from 320 to 380 nm, the VIS region is taken to mean the wavelength range from 380 nm to 780 nm and the NIR region is taken to mean the wavelength range from 780 nm to 2000 nm. Correspondingly, the term light is generally taken to mean electromagnetic radiation having wavelengths between 320 and 2000 nm, and in particular from 380 nm to 780 nm.

Herein, a dichroic dye is taken to mean a light-absorbing compound in which the absorption properties are dependent on the orientation of the compound relative to the direction of polarisation of the light. A dichroic dye compound in accordance with the present invention typically has an elongated shape, i.e. the compound is significantly longer in one spatial direction, i.e. along the longitudinal axis, than in the other two spatial directions.

The term "organic group" denotes a carbon or hydrocarbon group.

The term "carbon group" denotes a mono- or polyvalent organic group containing at least one carbon atom, where this group either contains no further atoms, such as, for example, —C≡C—, or optionally contains one or more further atoms, such as, for example, N, O, S, P, Si, Se, As, Te or Ge, for example carbonyl, etc. The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I, preferably F or Cl.

A carbon or hydrocarbon group can be a saturated group or an unsaturated group. Unsaturated groups are, for example, aryl, alkenyl or alkynyl groups. A carbon or hydrocarbon radical having 3 or more atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, arylalkyl, alkylaryloxy, arylalkyloxy, arylcarbonyl, aryloxycarbonyl, arylcarbonyl-oxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ allyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN and in which one more non-adjacent $CH_2$ groups may each be replaced, independently of one another, by —C($R^z$)=C($R^z$)—, —C≡C—, —N($R^z$)—, —O—, —S—, —CO—, —CO—O—, —O—CO—, —O—CO—O— in such a way that O and/or S atoms are not linked directly to one another.

$R^z$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO— or —O—CO—O— and in which one or more H atoms may be replaced by fluorine, an optionally substituted aryl or aryloxy group having 6 to 40 C atoms, or an optionally substituted heteroaryl or heteroaryloxy group having 2 to 40 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclo-pentyl, n-hexyl, cyclohexyl, 2-ethylhexyl, n-heptyl, cycloheptyl, n-octyl, cyclooctyl, n-nonyl, n-decyl, n-undecyl, n-dodecyl, trifluoromethyl, perfluoro-n-butyl, 2,2,2-trifluoroethyl, perfluorooctyl and perfluorohexyl.

Preferred alkenyl groups are, for example, ethenyl, propenyl, butenyl, pentenyl, cyclopentenyl, hexenyl, cyclohexenyl, heptenyl, cycloheptenyl, octenyl and cyclooctenyl.

Preferred alkynyl groups are, for example, ethynyl, propynyl, butynyl, pentynyl, hexynyl and octynyl.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy and n-dodecoxy.

Preferred amino groups are, for example, dimethylamino, methylamino, methylphenylamino and phenylamino.

Aryl and heteroaryl groups can be monocyclic or polycyclic, i.e. they can contain one ring, such as, for example, phenyl, or two or more rings, which may also be fused, such as, for example, naphthyl, or covalently bonded, such as, for example, biphenyl, or contain a combination of fused and linked rings. Heteroaryl groups contain one or more heteroatoms, preferably selected from O, N, S and Se. A ring system of this type may also contain individual non-conjugated units, as is the case, for example, in the fluorene basic structure.

Particular preference is given to mono-, bi- or tricyclic aryl groups having 6 to 25 C atoms and mono-, bi- or tricyclic heteroaryl groups having 2 to 25 C atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are derived, for example, from the parent structures benzene, biphenyl, terphenyl, [1,1':3',1"]terphenyl, naphthalene, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, dihydrothieno [3,4-b]-1,4-dioxin, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring, such as, for example, cyclohexane, or polycyclic, i.e. contain a plurality of rings, such as, for example, decahydronaphthalene or bicyclooctane. Particular preference is given to saturated groups. Preference is furthermore given to mono-, bi- or tricyclic groups having 3 to 25 C atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent CH$_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

The aryl, heteroaryl, carbon and hydrocarbon radicals optionally have one or more substituents, which are preferably selected from the group comprising silyl, sulfo, sulfonyl, formyl, amine, imine, nitrile, mercapto, nitro, halogen, C$_{1-12}$ alkyl, C$_{6-12}$ aryl, C$_{1-12}$ alkoxy, hydroxyl, or combinations of these groups.

Preferred substituents are, for example, solubility-promoting groups, such as alkyl or alkoxy, electron-withdrawing groups, such as fluorine, nitro or nitrile, or substituents for increasing the glass transition temperature (T$_g$) in the polymer, in particular bulky groups, such as, for example, t-butyl or optionally substituted aryl groups.

Preferred substituents are F, Cl, Br, I, —CN, —NO$_2$, —NCO, —NCS, —OCN, —SCN, —C(=O)N(R$^z$)$_2$, —C(=O)Y$^1$, —C(=O)R$^z$, —N(R$^z$)$_2$, in which R$^z$ has the meaning indicated above, and Y$^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

More preferred substituents, for example, F, Cl, CN, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, furthermore phenyl.

Herein, the substituent denoted L on each occurrence, identically or differently, is F, Cl, ON, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms.

It is preferred that L on each occurrence, identically or differently, denotes F or straight-chain or branched, in each case optionally fluorinated, alkyl or alkoxy having 1 to 7 C atoms, "Substituted silyl or aryl" preferably means substituted by halogen, —CN, R$^{y1}$, —CO—R$^{y1}$, —CO—O—R$^{y1}$, —O—CO—R$^{y1}$ or —O—CO—O—R$^{y1}$, in which R$^{y1}$ has the meaning indicated above.

In a preferred embodiment A$^{11}$, A$^{12}$, A$^{21}$ and A$^{22}$ preferably on each occurrence, identically or differently, represent an aryl group having 6 to 15 C atoms or a heteroaryl group having 2 to 15 C atoms, which may be substituted by one or more radicals L as defined above and below, wherein L preferably is F.

A$^{11}$, A$^{12}$, A$^{21}$ and A$^{22}$ are particularly preferably selected on each occurrence, identically or differently, from groups, optionally substituted by radicals L and in particular F, derived from the parent substances benzene, fluorene, naphthalene, pyridine, pyrimidine, pyridazine, thiophene, selenophene, thiazole, thiadiazole, benzothiadiazole, dihydrothienodioxin, benzothiophene, dibenzothiophene, benzodithiophene, cyclopentadithiophene, thienothiophene, indenothiophene, furan, benzofuran, dibenzofuran and quinoline, and even more preferably from benzene, naphthalene, thiadiazole, thienothiophene and thiophene.

In a particular embodiment the compounds of formulae Ia, Ib and Ic contain one or more heterocyclic structures selected from the following structures

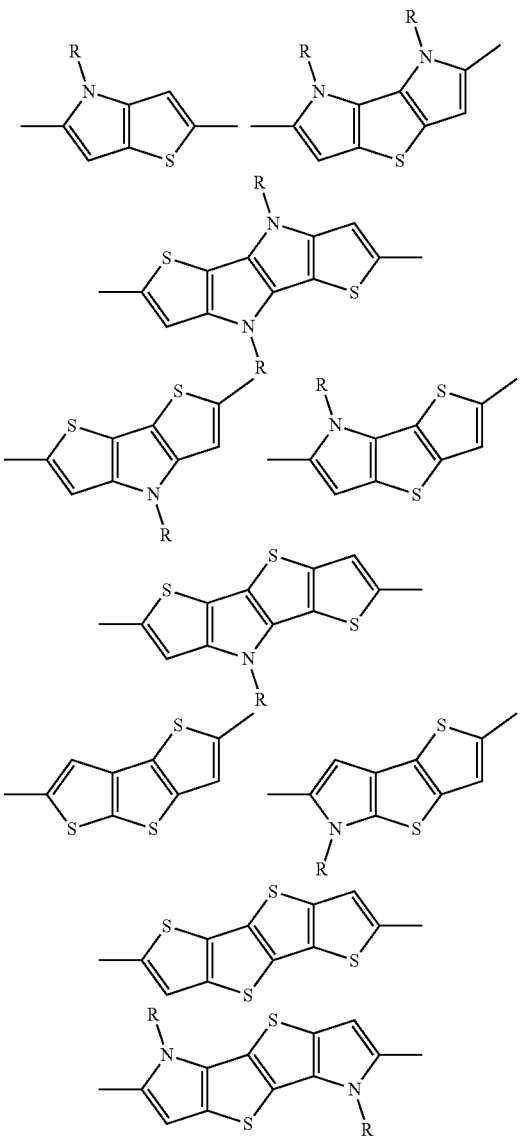

wherein R has the meaning as set forth for R$^{13}$ above and below.

In a particularly preferred embodiment A$^{11}$ and A$^{12}$ denote, independently of one another, 1,4-phenylene, 1,4-naphthylene, 2,6-naphthylene, thiazole-2,5-diyl, thiophene-2,5-diyl or thienothiophene-2,5-diyl, wherein one or more H atoms may be replaced by the group L as defined above and below. Even more preferably A$^{11}$, A$^{12}$ denote, independently of one another, 1,4-phenylene, thiophene-2,5-diyl or thienothiophene-2,5-diyl, wherein one or more H atoms may be replaced by the group L as defined above and below.

According to a preferred embodiment the compounds of formulae Ia, Ib and Ic contain 3, 4 or 5 aromatic or heteroaromatic ring structures.

In a preferred embodiment X in formulae Ia and Ib denotes S or Se, and in particular S.

In a preferred embodiment $Z^{11}$ and $Z^{12}$ denote, independently of one another, a single bond, —CH=CH—, —CF=CF— or —C≡C—. It is particularly preferred that $Z^{11}$ and $Z^{12}$ denote a single bond.

$Z^{21}$ and $Z^{22}$ preferably denote, independently of one another, a single bond, —CH$_2$CH$_2$—, —CF$_2$CF$_2$—, —CH=CH—, —CF=CF—, —C≡C—, —OCH$_2$—, —CH$_2$O—, —OCO—, —COO—, —OCF$_2$— or —CF$_2$O—, more preferably —OCF$_2$—, —CF$_2$O— or a single bond, and particularly preferably a single bond.

Preferably $Z^{31}$, $Z^{32}$ denote on each occurrence, identically or differently, a single bond, —OCF$_2$— or —CF$_2$O—, more preferably a single bond.

Preferably, $R^{11}$, $R^{12}$, $R^{13}$ identically or differently, denote H, F, CN, CO or straight-chain, branched or cyclic alkyl having 1 to 9 C atoms, in which, in addition, one or more non-adjacent CH$_2$ groups may each be replaced, independently of one another, —O—, —S—, —CO—, —CO—O—, —O—CO— or —O—CO—O— in such a way that O and/or S atoms are not linked directly to one another, and in which, in addition, one or more H atoms may be replaced by F, Cl, Br, I or CN, In an preferred embodiment, $R^{11}$ and $R^{12}$, independently of one another, denote a branched alkyl group having 3 to 25 C atoms, preferably 3 to 12 C atoms, in which one or more H atoms can be replaced by F, one or more CH$_2$ groups can be replaced by O and/or NH and one or more CH groups can be replaced by N.

The groups $R^{11}$ and $R^{12}$ particularly preferably, independently of one another, denote an alkyl group, preferably with a methyl, ethyl, n-propyl, n-butyl, or n-pentyl group bonded to an ethyl, n-propyl, n-hexyl, n-heptyl, n-octyl, n-nonyl or n-decyl group, for example 2-ethylhexyl, 2-ethylheptyl, 2-ethyloctyl, 2-ethylnonyl, 2-ethyldecyl, 3-ethylhexyl, 3-ethylheptyl, 3-ethyloctyl, 3-ethylnonyl, 3-ethyldecyl, and the like.

In a particularly preferred embodiment $R^{11}$ and $R^{12}$, independently of one another, denote ethyl, n-propyl, n-butyl, n-pentyl, n-hexyl, n-heptyl or a branched alkyl group having 3 to 12 C atoms.

In another preferred embodiment, the groups $R^{11}$ and $R^{12}$, independently of one another, denote a straight chain or branched alkyl or dialkylamino group having 1 to 12 C atoms per alkyl group.

The groups $R^{x1}$ and $R^{x2}$ are preferably on each occurrence, identically or differently, H, F or an alkyl group having 1 to 6 C atoms, more preferably H or F, and in particular H.

The indices r and s preferably are, independently of one another, equal to 0, 1 or 2, more preferably 1 or 2, and even more preferably 1.

It is particularly preferred that r+s is equal to 1, 2 or 3.

The compounds of formulae Ia and Ib are preferably selected from the compounds of formulae Ia-1 and Ib-1

Ia-1

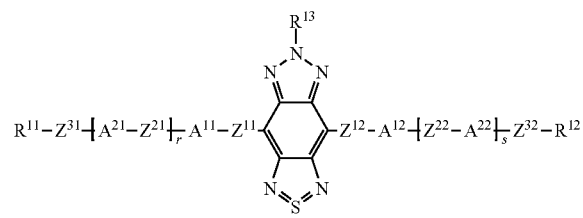

Ib-1

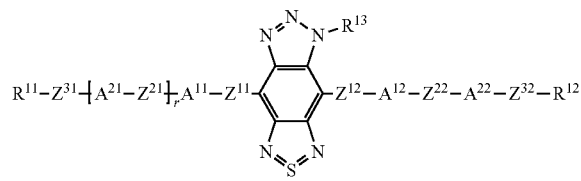

wherein the groups have the meanings as set forth for formulae Ia and Ib above.

The liquid crystalline media according to the invention preferably comprise one or more compounds selected from the group of compounds of formulae Ia-1 and Ib-1.

Preferred compounds of formula Ia-1 are selected from the following structures:

Ia-1-i

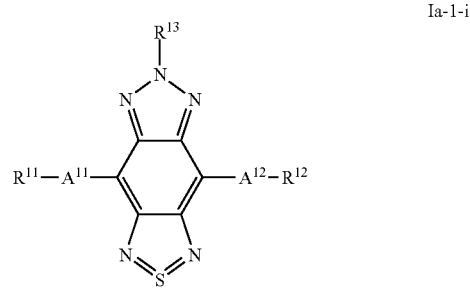

Ia-1-ii

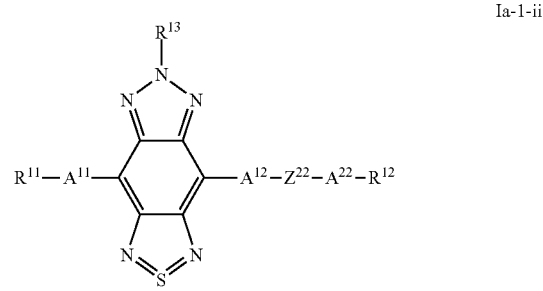

Ia-1-iii

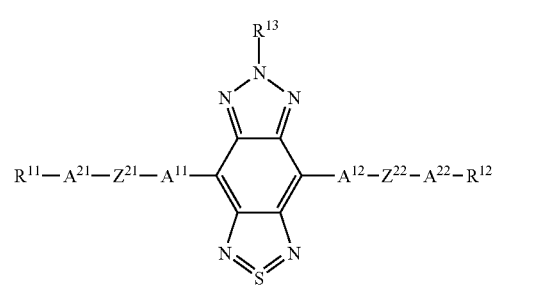

where the groups have the meanings indicated above, and where $Z^{21}$ and $Z^{22}$ on each occurrence, identically or differently, preferably denote a single bond, —CR$^{x1}$=CR$^{x2}$—, —C≡C— or —C(O)—, particularly preferably a single bond.

Preferred compounds of formula Ib-1 are selected from the following structures:

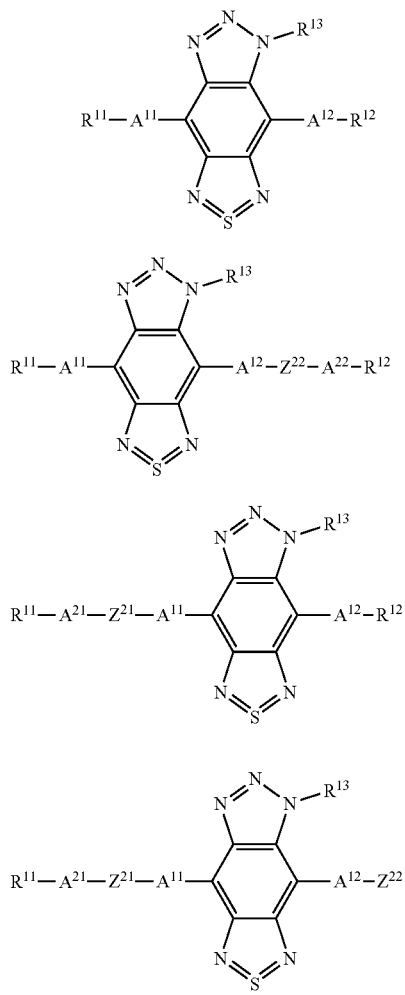

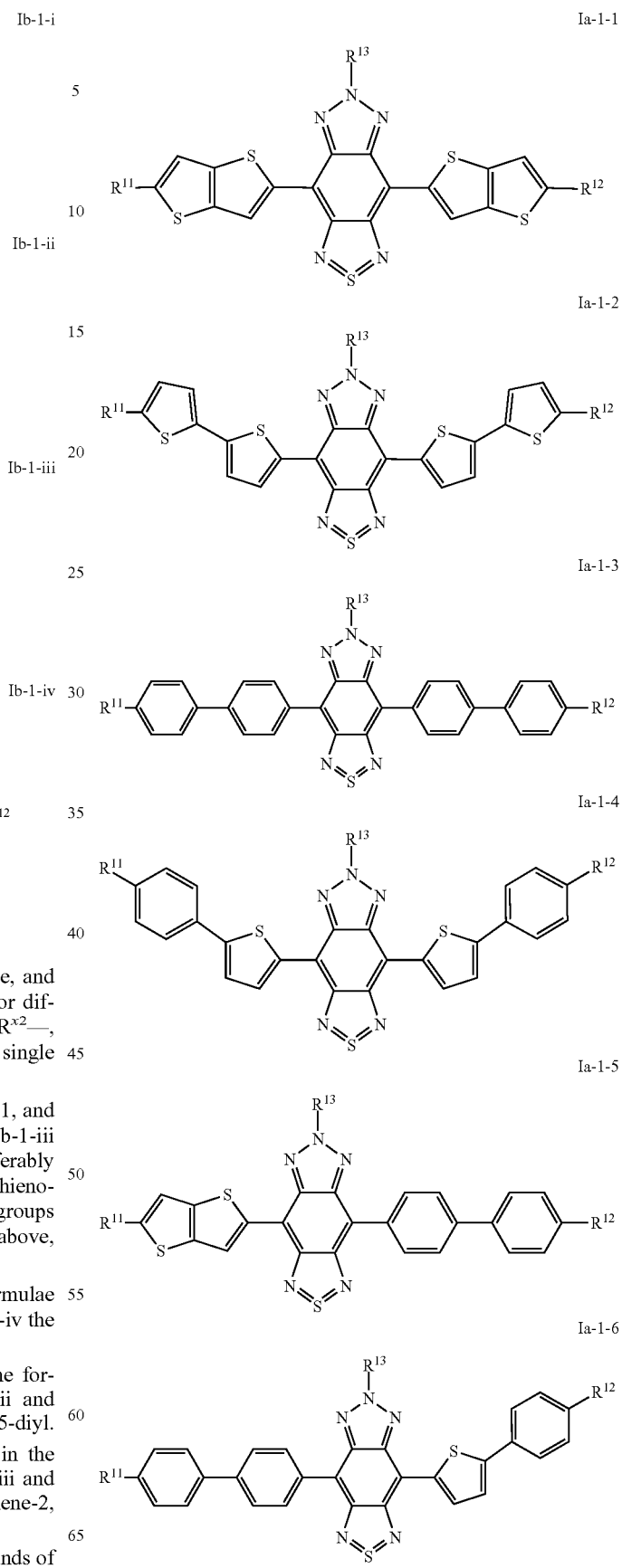

where the groups have the meanings indicated above, and where $Z^{21}$ and $Z^{22}$ on each occurrence, identically or differently, preferably denote a single bond, —CR$^{x1}$═CR$^{x2}$—, —C≡C— or —C(O)—, particularly preferably a single bond.

For the formulae Ia and Ib, preferably Ia-1 and Ib-1, and in particular Ia-1-i, Ia-1-ii, Ia-1-iii, Ib-1-i, Ib-1-ii, Ib-1-iii and Ib-1-iv the groups $A^{11}$, $A^{12}$, $A^{21}$ and $A^{22}$ are preferably selected from 1,4-phenylene, thiophene-2,5-diyl and thienothiophene-2,5-diyl. In another embodiment these groups may be substituted by one or more radicals L defined above, in particular by one or more F.

According to a preferred embodiment in the formulae Ia-1-i, Ia-1-ii, Ia-1-iii, Ib-1-i, Ib-1-ii, Ib-1-iii and Ib-1-iv the groups $A^{11}$ and $A^{12}$ are both 1,4-phenylene.

According to another preferred embodiment in the formulae Ia-1-i, Ia-1-ii, Ia-1-iii, Ib-1-i, Ib-1-ii, Ib-1-iii and Ib-1-iv the groups $A^{11}$ and $A^{12}$ are both thiophene-2,5-diyl.

According to yet another preferred embodiment in the formulae Ia-1-i, Ia-1-ii, Ia-1-iii, Ib-1-i, Ib-1-ii, Ib-1-iii and Ib-1-iv the groups $A^{11}$ and $A^{12}$ are both thienothiophene-2,5-diyl.

In a particularly preferred embodiment the compounds of formula Ia are selected from the following formulae:

Ia-1-7

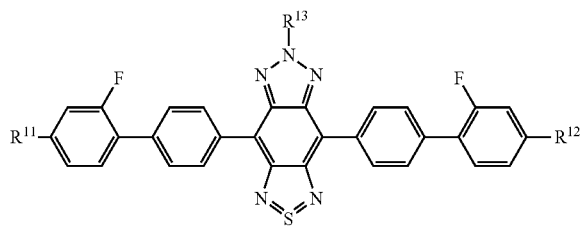

wherein $R^{11}$, $R^{12}$ and $R^{13}$ have the meanings as given above and below, and preferably on each occurrence identically or differently denote a straight-chain alkyl or alkoxy group having 1 to 12 C atoms or a branched alkyl or alkoxy group having 3 to 25 C atoms or CN, more preferably n-pentyl, n-hexyl, n-heptyl, 2-ethylhexyl, 2-ethylheptyl, 2-ethyloctyl, 2-ethylnonyl, 2-ethyldecyl, 3-ethylhexyl, 3-ethylheptyl, 3-ethyloctyl, 3-ethylnonyl, 3-ethyldecyl, 2-octyldodecyl or CN.

In another embodiment the compounds of formula Ia are selected from the following formulae:

Ia-2-1

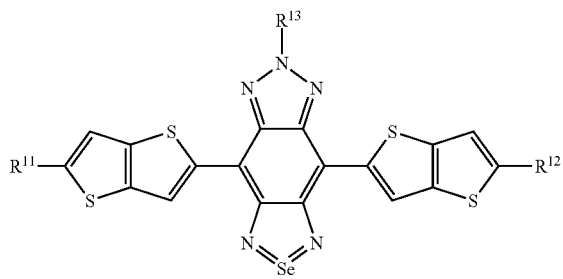

Ia-2-2

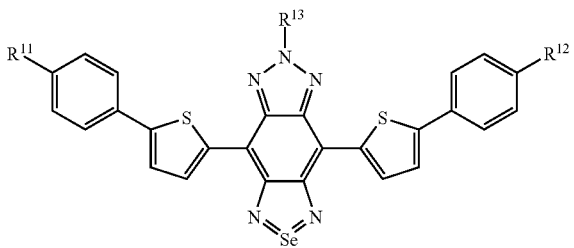

wherein $R^{11}$, $R^{12}$ and $R^{13}$ have the meanings as given above and below.

In a particularly preferred embodiment the compounds of formula Ib are selected from the following formulae:

Ib-1-1

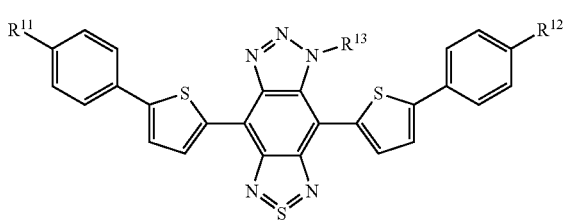

Ib-1-2

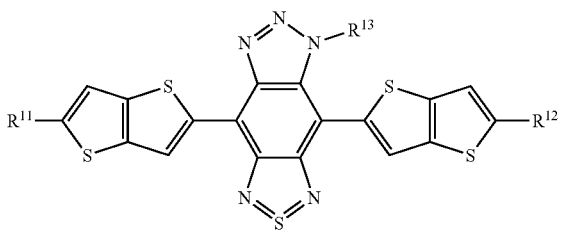

wherein $R^{11}$, $R^{12}$ and $R^{13}$ have the meanings as given above and below, and preferably on each occurrence identically or differently denote a straight-chain alkyl or alkoxy group having 1 to 12 C atoms or a branched alkyl or alkoxy group having 3 to 25 C atoms or CN, more preferably n-pentyl, n-hexyl, n-heptyl, 2-ethylhexyl, 2-ethylheptyl, 2-ethyloctyl, 2-ethylnonyl, 2-ethyldecyl, 3-ethylhexyl, 3-ethylheptyl, 3-ethyloctyl, 3-ethylnonyl, 3-ethyldecyl, 2-octyldodecyl or CN.

In a preferred embodiment the compounds of formula Ic are selected from the following formula:

Ic-1-1

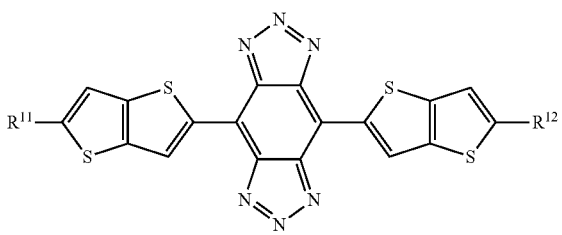

wherein $R^{11}$ and $R^{12}$ have the meanings as given above and below.

Compounds of formula Ia are preferably prepared according to the following scheme.

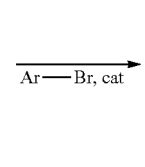

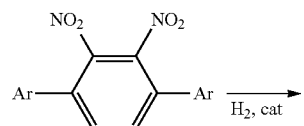

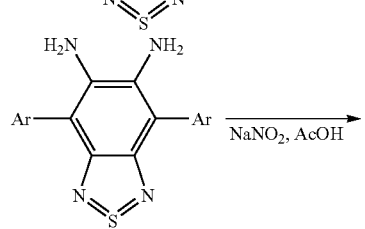

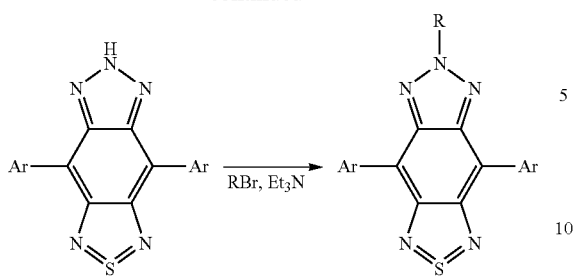

Compounds of formula Ib are preferably prepared according to the following scheme.

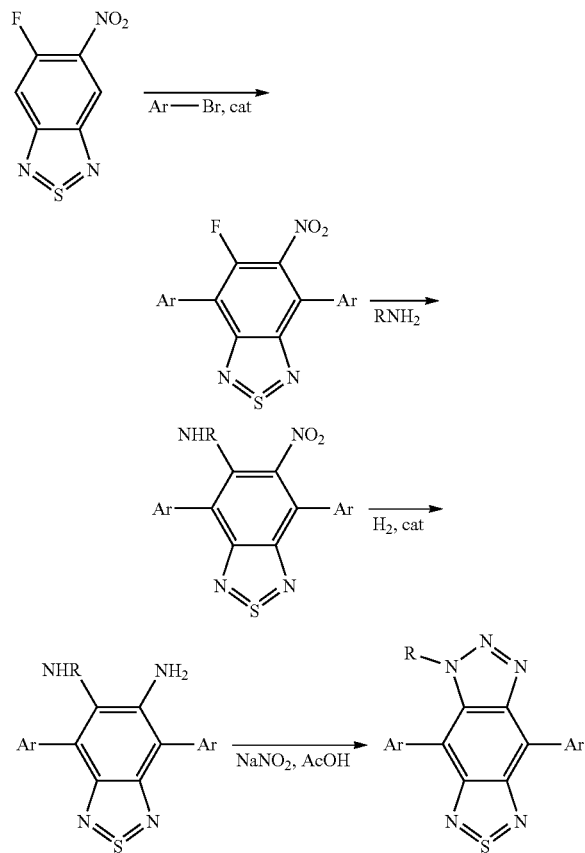

Compounds of formula Ic are preferably prepared according to the following scheme.

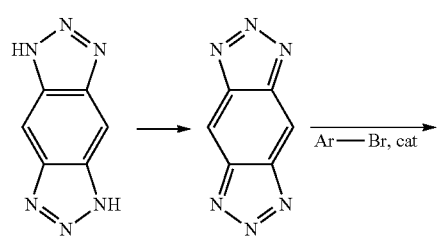

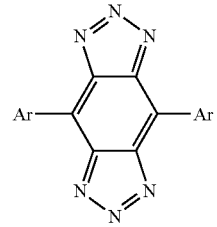

The corresponding selenadiazoles and telluriadiazoles can be prepared analogous to the thiadiazoles, wherein preferably precursors are provided by reacting ortho-phenylenediamine with $SeO_2$ or respectively $TeCl_4$.

Methods for preparing compounds of formulae Ia, Ib and Ic can also be based on or be analogous to known processes, e.g. as described in standard works of organic chemistry, such as, for example, Houben-Weyl, Methoden der organischen Chemie [Methods of Organic Chemistry], Thieme Verlag, Stuttgart. For specific processes for the preparation of compounds of formulae Ia, Ib and Ic, reference is furthermore made to the Examples and also to the known literature.

The compounds of formulae Ia, Ib and Ic preferably are positively dichroic dyes, i.e. dyes which have a positive degree of anisotropy R.

The degree of anisotropy R is determined for the LC mixture comprising the dye from the values of the extinction coefficients for parallel and perpendicular alignment of the molecules relative to the direction of the polarisation of the light.

According to the invention the degree of anisotropy R preferably is greater than 0.4, more preferably greater than 0.6, even more preferably greater than 0.7, and in particular greater than 0.8.

The absorption preferably reaches a maximum when the polarisation direction of the light is parallel to the direction of the longest molecular elongation of the compounds of formula Ia, Ib and Ic, and it preferably reaches a minimum when the polarisation direction of the light is perpendicular to the direction of the longest molecular elongation of the compounds of formula Ia, Ib and Ic.

The compounds according to the invention preferably exhibit an absorption maximum at a wavelength of greater than 600 nm.

The compounds of formulae Ia, Ib and Ic can favourably be used as guest compounds, in particular as dichroic dyes, in liquid crystalline host mixtures.

In a preferred embodiment the mesogenic medium comprises one or more compounds selected from the group of compounds of formulae Ia and Ib as set forth above and below.

In a particularly preferred embodiment the mesogenic medium comprises at least one compound of formula Ia as set forth above and below.

In another particularly preferred embodiment the mesogenic medium comprises at least one compound of formula Ib as set forth above and below.

It is particularly preferred that the mesogenic medium according to the invention comprises at least one compound of formula Ia as set forth above and below and in addition at least one compound of formula Ib as set forth above and below.

In principle, a suitable host mixture is any dielectrically negative or positive LC mixture which is suitable for use in conventional VA, TN, STN, IPS or FFS displays.

Suitable LC mixtures are known in the art and are described in the literature. LC media for VA displays having negative dielectric anisotropy are described in for example EP 1 378 557 A1.

Suitable LC mixtures having positive dielectric anisotropy which are suitable for LCDs and especially for IPS displays are known, for example, from JP 07-181 439 (A), EP 0 667 555, EP 0 673 986, DE 195 09 410, DE 195 28 106, DE 195 28 107, WO 96/23 851, WO 96/28 521 and WO2012/079676.

Preferred embodiments of the liquid crystalline media having negative or positive dielectric anisotropy according to the invention are indicated below.

The LC host mixture preferably is a nematic LC mixture, and preferably does not have a chiral LC phase.

In a preferred embodiment of the present invention the LC medium contains an LC host mixture with negative dielectric anisotropy. Accordingly, in preferred embodiments the mesogenic media according to the invention comprise components selected from the following items a) to w):

a) Mesogenic medium which comprises one or more compounds selected from the group of compounds of the formulae CY, PY and AC:

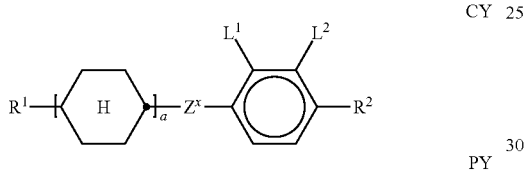

CY

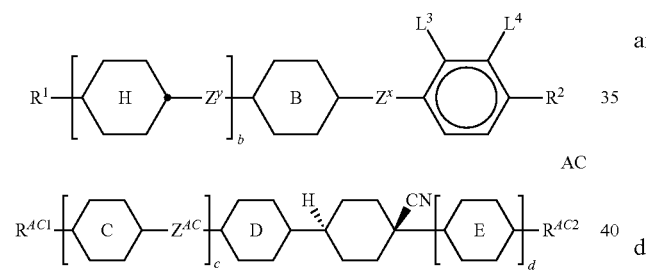

PY

AC wherein
a denotes 1 or 2,
b denotes 0 or 1,
c is 0, 1 or 2,
d is 0 or 1.

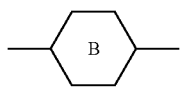

denotes

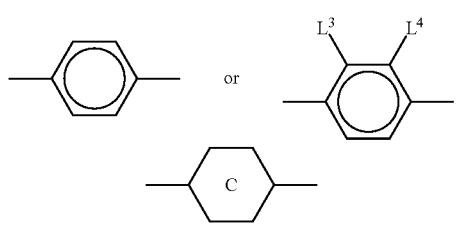

and

denote

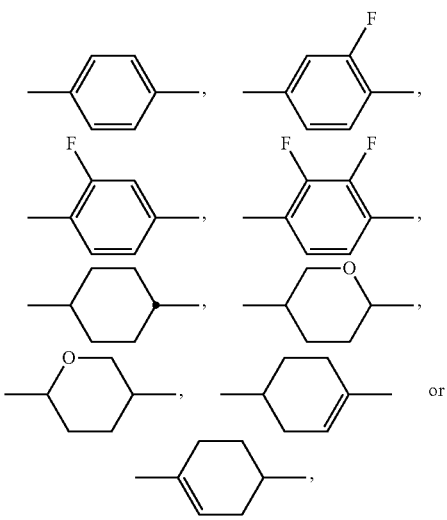

and

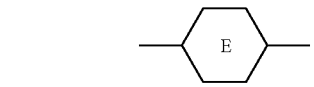

denotes

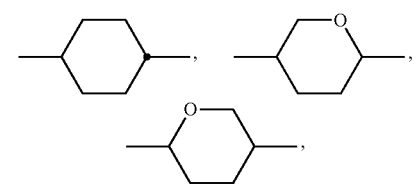

$R^1$ and $R^2$ $R^{AC1}$ and $R^{AC2}$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond, $L^{1-4}$ each, independently of one another, denote F, Cl, CN, $OCF_3$, $CF_3$, $CH_3$, $CH_2F$, $CHF_2$.

in which the individual radicals have the following meanings:

each, independently of one another, denote alkyl having 1 to 12 C atoms, in which, in addition, one or two non-adjacent CH$_2$ groups may be replaced by —O—, —CH=CH—, —CO—, —O—CO— or —CO—O— in such a way that O atoms are not linked directly to one another, $Z^{AC}$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, and Preferably, both $L^1$ and $L^2$ denote F or one of $L^1$ and $L^2$ denotes F and the other denotes Cl, or both $L^3$ and $L^4$ denote F or one of $L^3$ and $L^4$ denotes F and the other denotes Cl.

The compounds of the formula CY are preferably selected from the group consisting of the following sub-formulae:

CY1
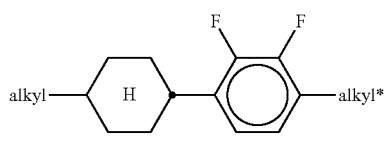

CY2
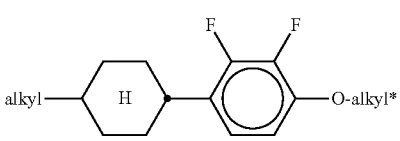

CY3
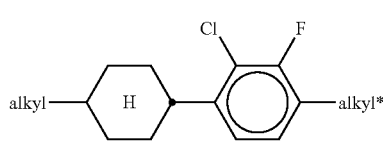

CY4
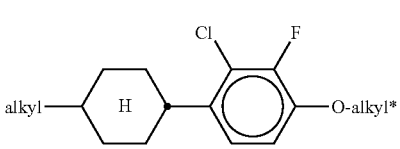

CY5
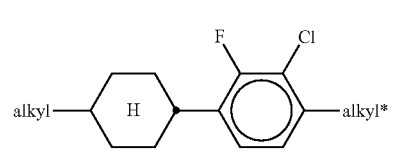

CY6
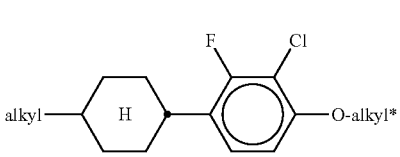

CY7
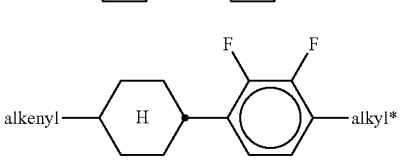

-continued

CY8
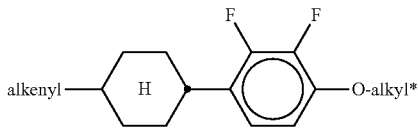

CY9
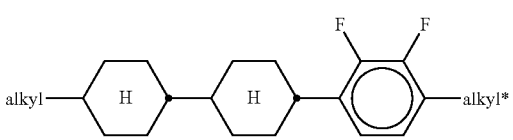

CY10
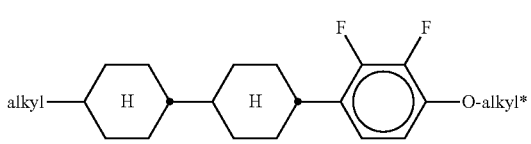

CY11
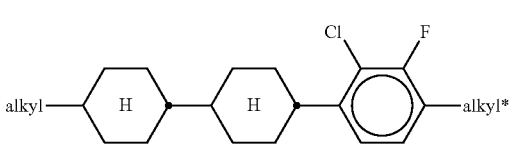

CY12
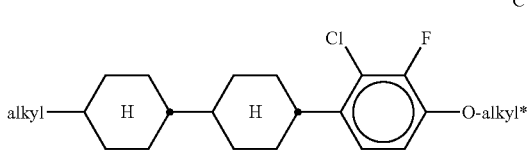

CY13
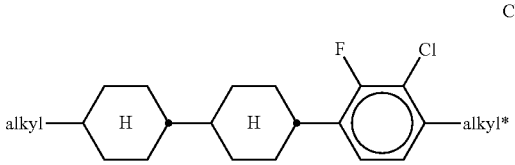

CY14
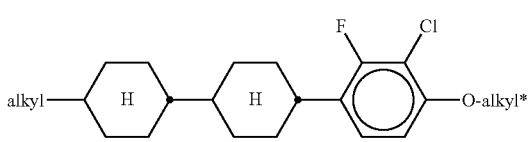

CY15
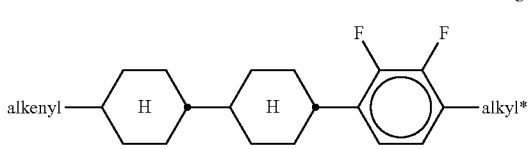

CY16
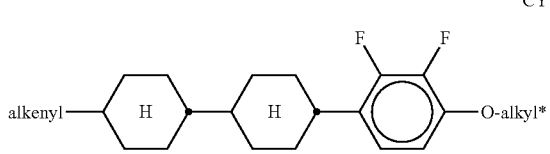

CY17
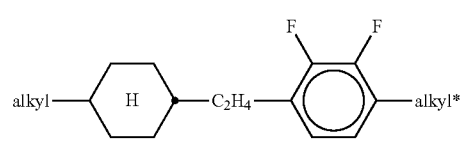

CY18 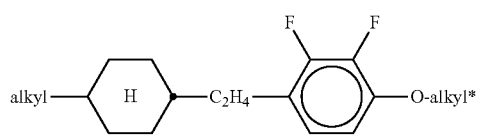

CY19 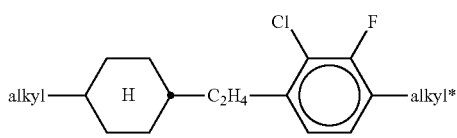

CY20 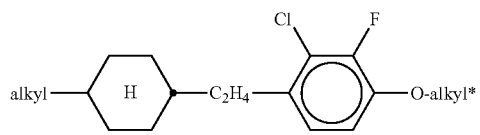

CY21 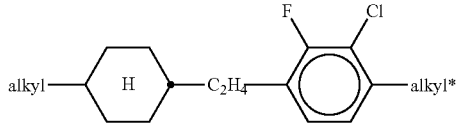

CY22 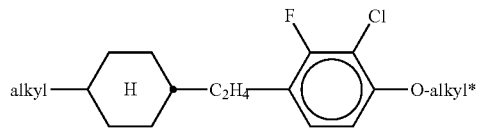

CY23 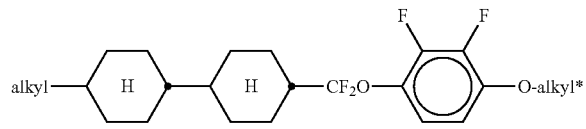

CY24 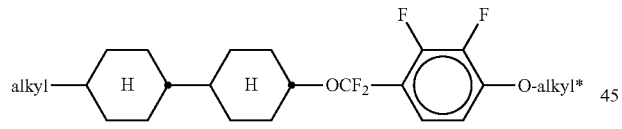

CY25 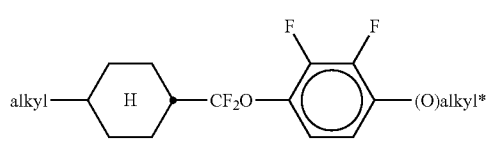

CY26 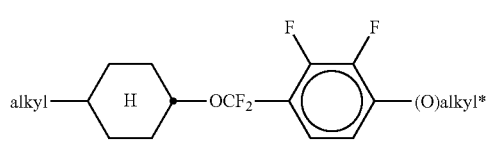

CY27 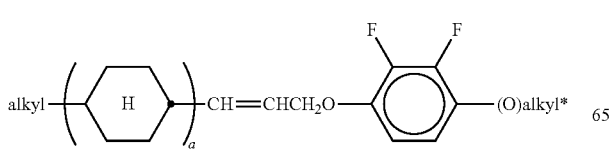

CY28 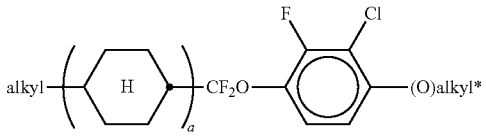

CY29 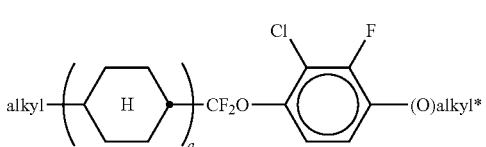

CY30 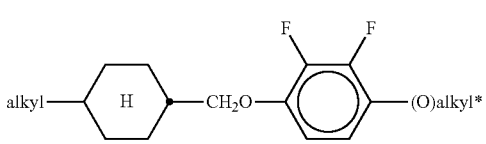

CY31 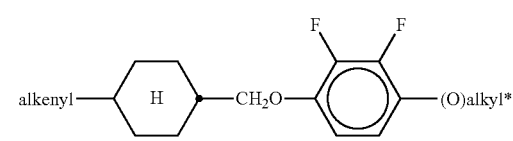

CY32 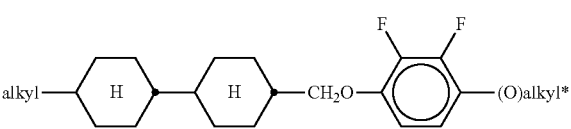

CY33 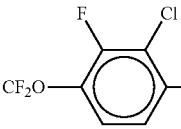

wherein a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

PY1 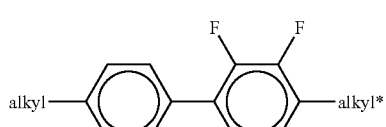

PY2 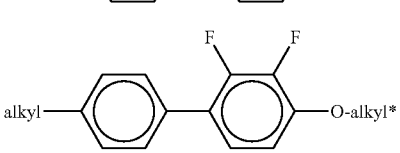

PY3 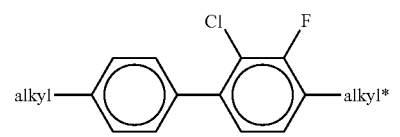

PY4 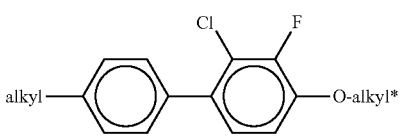

PY5 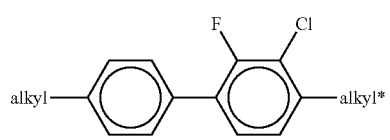

PY6 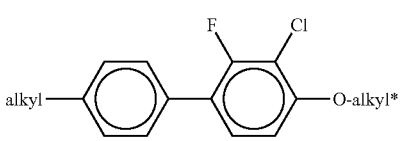

PY7 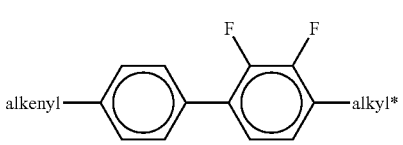

PY8 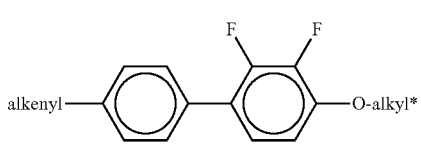

PY9 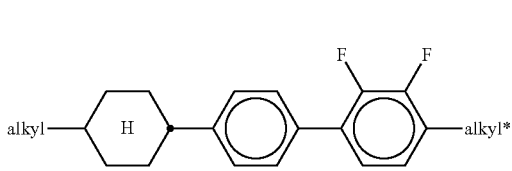

PY10 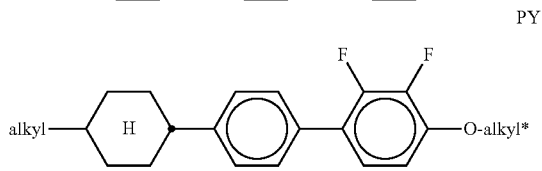

PY11 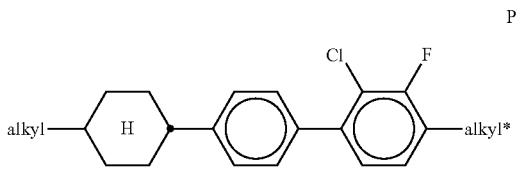

PY12 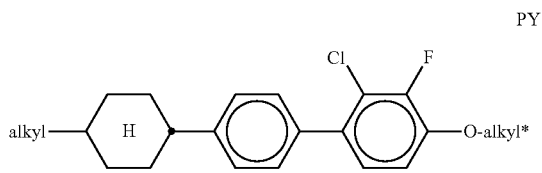

PY13 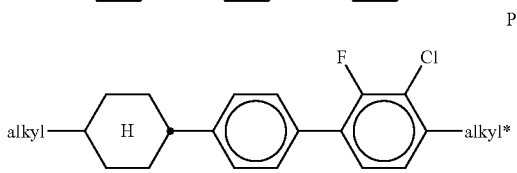

PY14 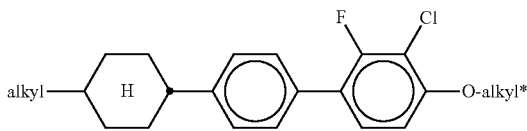

PY15 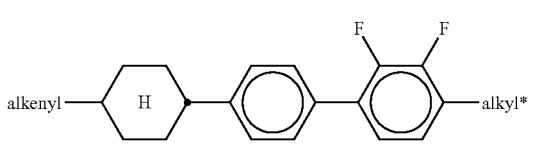

PY16 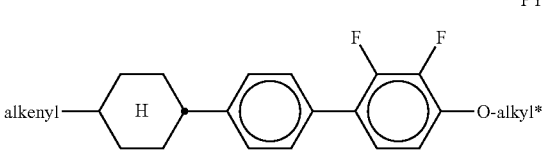

PY17 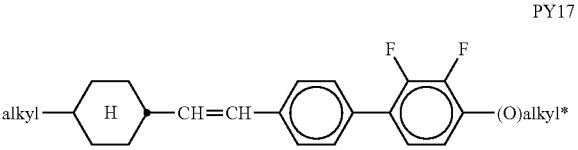

PY18 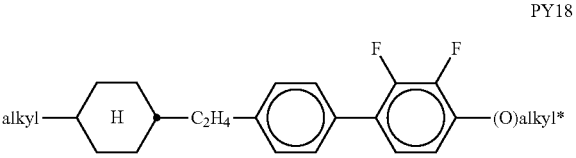

PY19 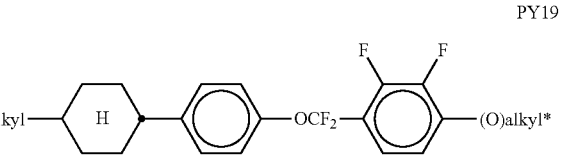

PY20 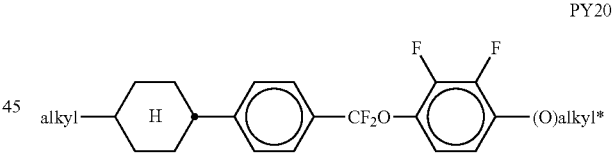

PY21 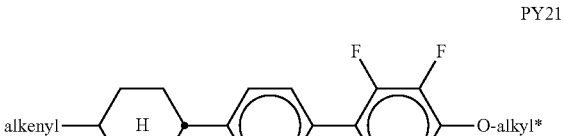

wherein alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula AC are preferably selected from the group of compounds of the following sub-formulae:

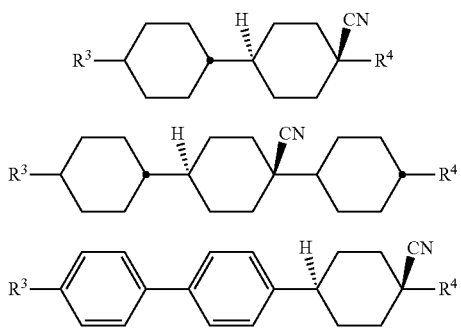

AC1

AC2

AC3 b) Mesogenic medium which additionally comprises one or more compounds of the following formula:

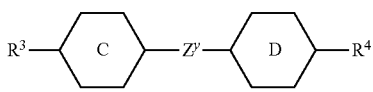

ZK in which the individual radicals have the following meanings:

denotes

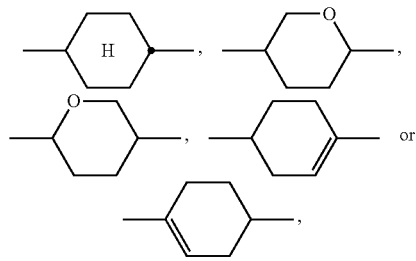

denotes

$R^3$ and $R^4$ each, independently of one another, denote alkyl having 1 to 12 C atoms, in which, in addition, one or two non-adjacent $CH_2$ groups may be replaced by —O—, —CH=CH—, —CO—, —O—CO— or —CO—O— in such a way that O atoms are not linked directly to one another, $Z^y$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, preferably a single bond.

The compounds of the formula ZK are preferably selected from the group consisting of the following sub-formulae:

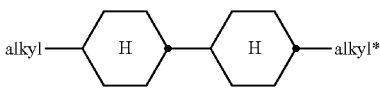

ZK1

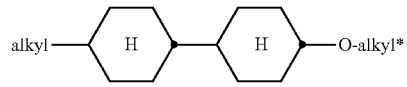

ZK2

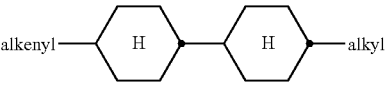

ZK3

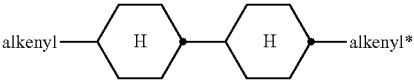

ZK4

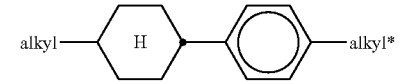

ZK5

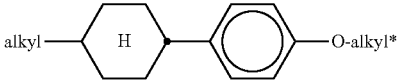

ZK6

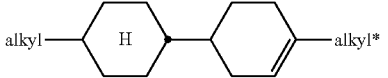

ZK7

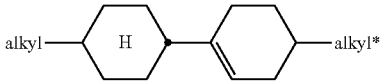

ZK8

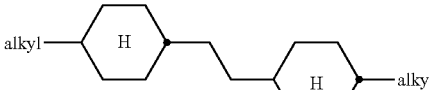

ZK9

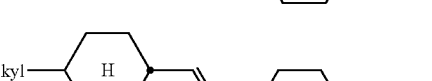

ZK10 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

Especially preferred are compounds of formula ZK1 and ZK3.

Particularly preferred compounds of formula ZK are selected from the following sub-formulae:

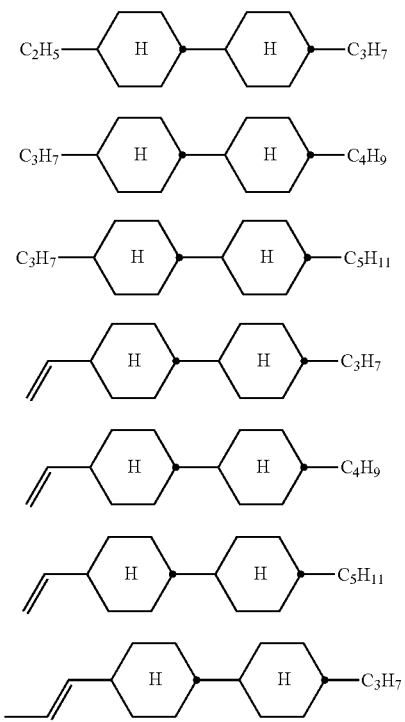

wherein the propyl, butyl and pentyl groups are straight-chain groups.

Most preferred are compounds of formula ZK1a and ZK3a.

c) Mesogenic medium which additionally comprises one or more compounds of the following formula:

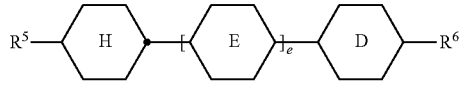

DK in which the individual radicals on each occurrence, identically or differently, have the following meanings:

R⁵ and R⁶ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms,

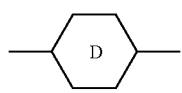

denotes

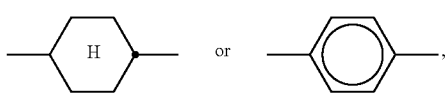

ZK1a
ZK1b
ZK1c
ZK3a
ZK3b
ZK3c
ZK3d denotes or and e denotes 1 or 2.

The compounds of the formula DK are preferably selected from the group consisting of the following sub-formulae:

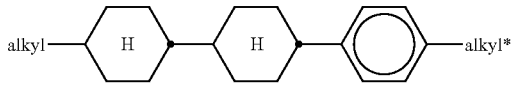

DK1

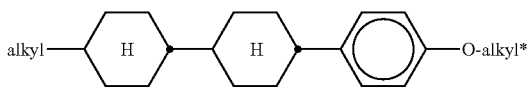

DK2

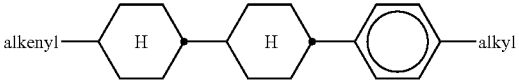

DK3

DK4

DK5

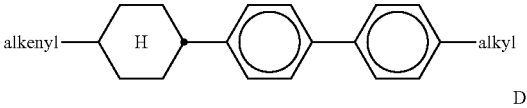

DK6

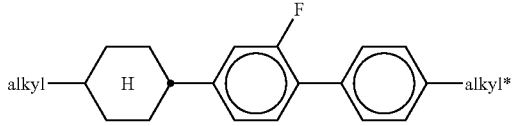

DK7

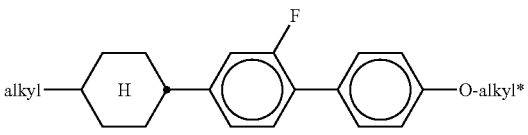

DK8

-continued

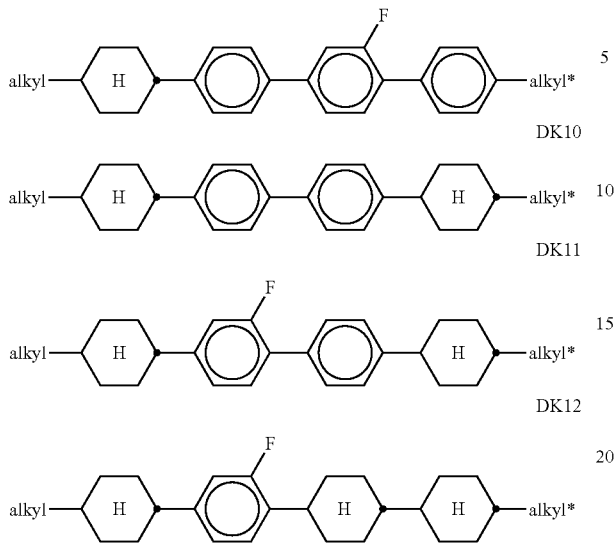

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

Preference is given to compounds of the formulae DK1, DK4, DK7, DK 9, DK10 and DK11.

d) Mesogenic medium which additionally comprises one or more compounds of the following formula:

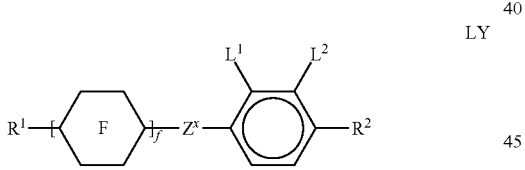

LY in which the individual radicals have the following meanings:

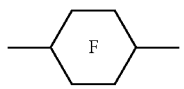

denotes

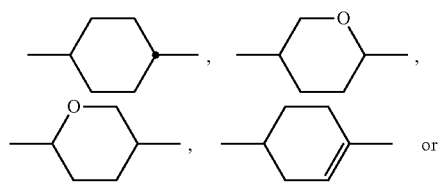

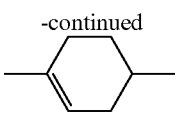

with at least one ring F being different from cyclohexylene, f denotes 1 or 2, $R^1$ and $R^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, $Z^x$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, $L^1$ and $L^2$ each, independently of one another, denote F, Cl, OCF$_3$, CF$_3$, CH$_3$, CH$_2$F, CHF$_2$.

Preferably, both radicals $L^1$ and $L^2$ denote F or one of the radicals $L^1$ and $L^2$ denotes F and the other denotes Cl.

The compounds of the formula LY are preferably selected from the group consisting of the following sub-formulae:

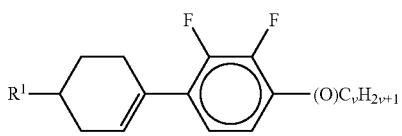

LY1

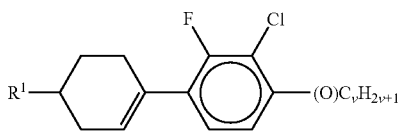

LY2

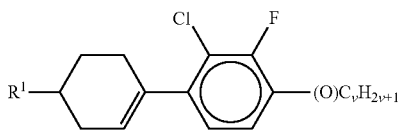

LY3

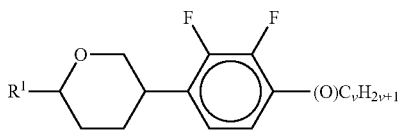

LY4

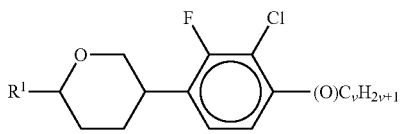

LY5

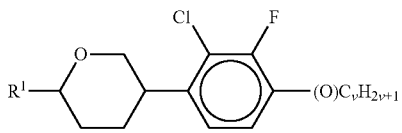

LY6

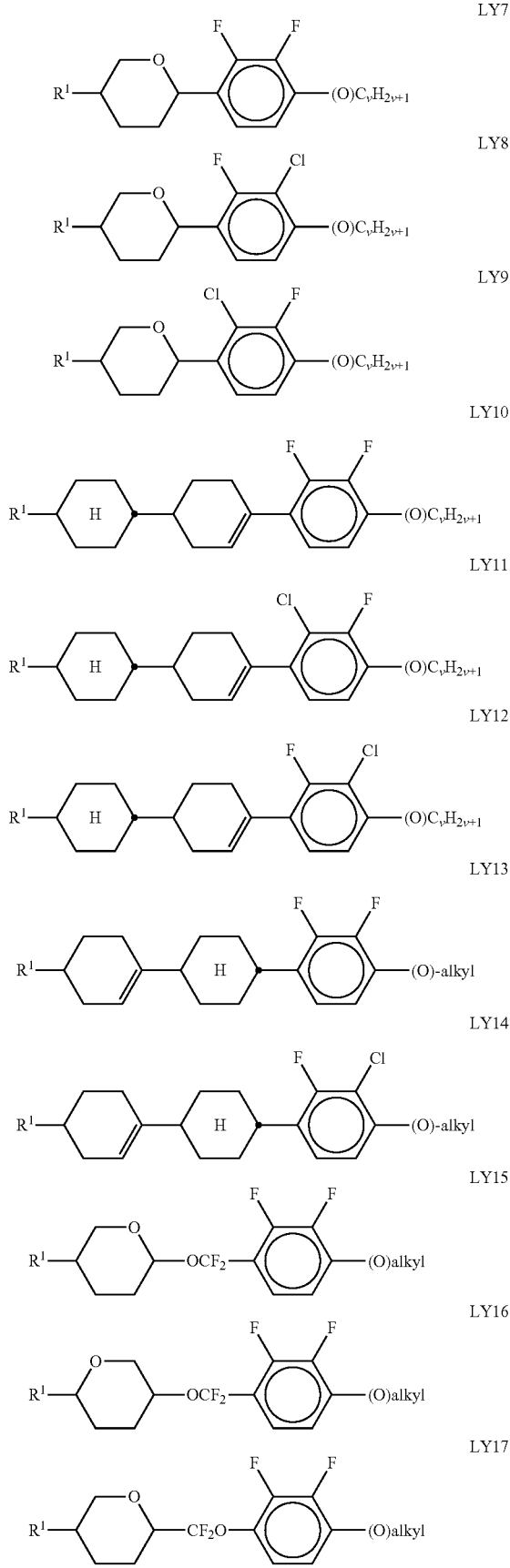

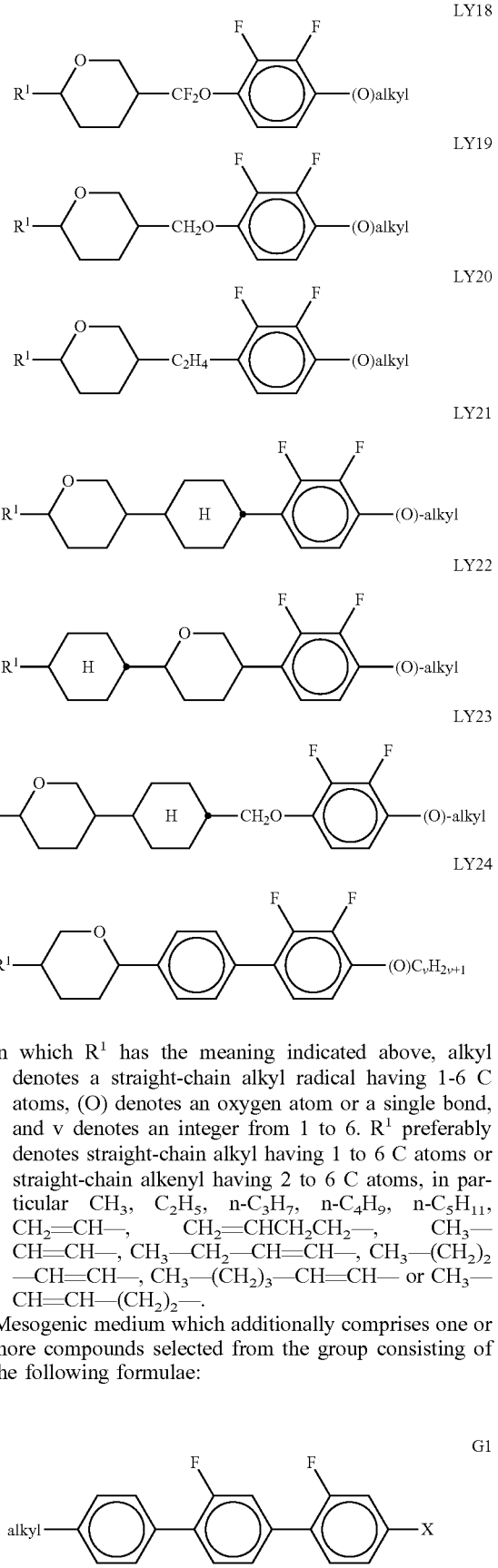

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

e) Mesogenic medium which additionally comprises one or more compounds selected from the group consisting of the following formulae:

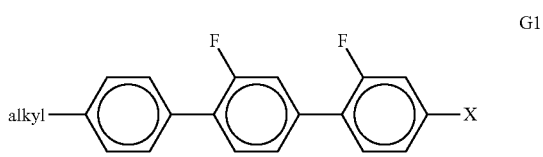

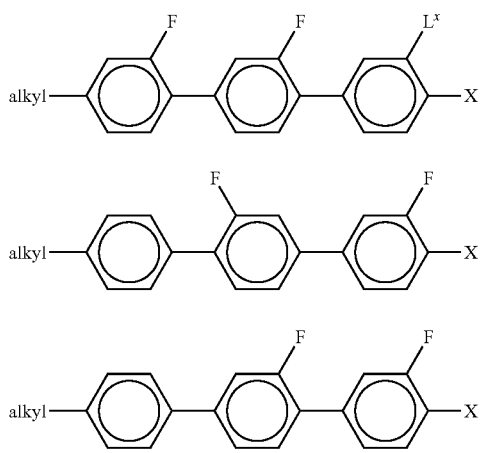

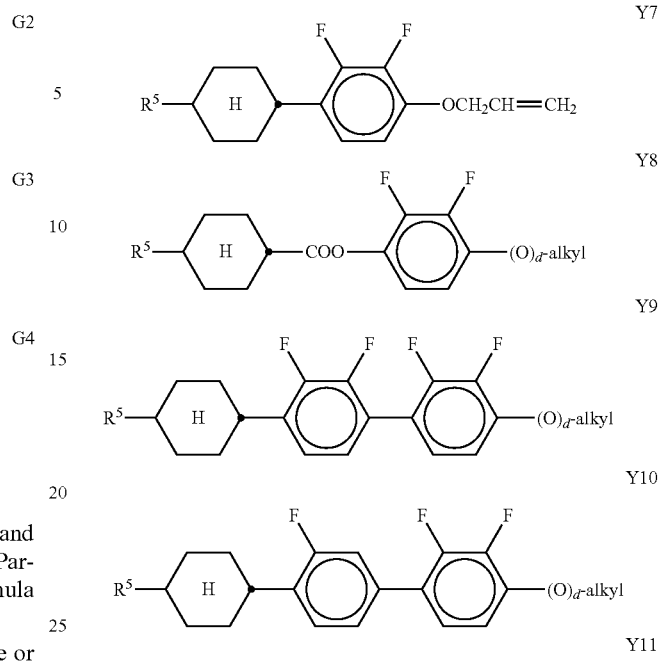

in which alkyl denotes $C_{1-6}$-alkyl, $L^x$ denotes H or F, and X denotes F, Cl, $OCF_3$, $OCHF_2$ or $OCH=CF_2$. Particular preference is given to compounds of the formula G1 in which X denotes F.

f) Mesogenic medium which additionally comprises one or more compounds selected from the group consisting of the following formulae:

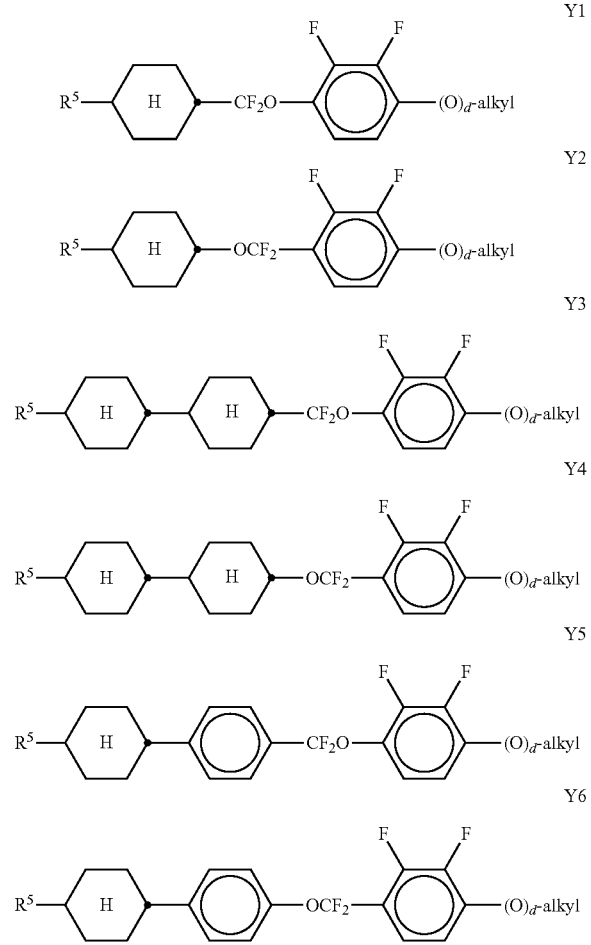

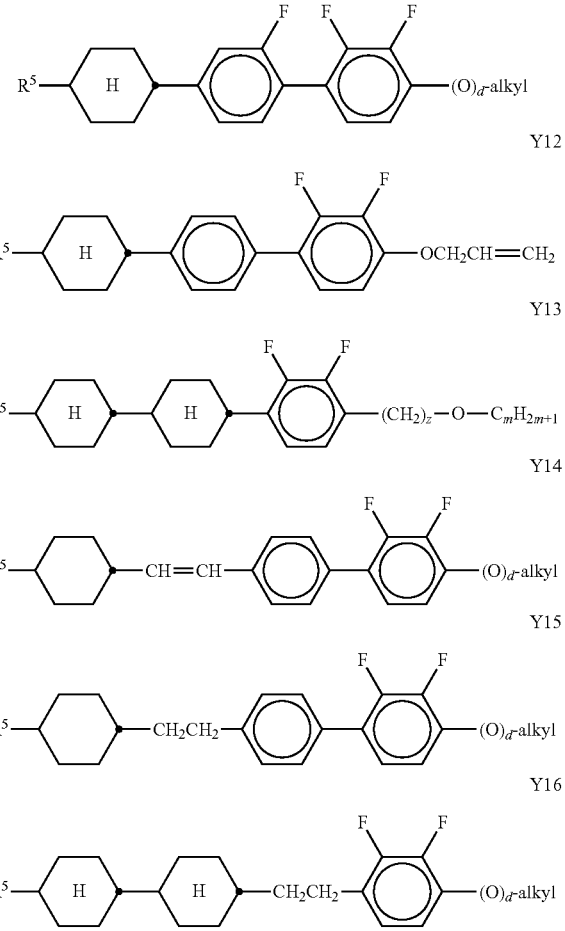

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

g) Mesogenic medium which additionally comprises one or more biphenyl compounds selected from the group consisting of the following formulae:

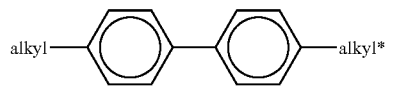

B1

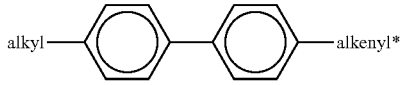

B2

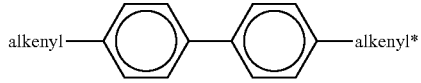

B3 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2$=$CH$—, $CH_2$=$CHCH_2CH_2$—, $CH_3$—$CH$=$CH$—, $CH_3$—$CH_2$—$CH$=$CH$—, $CH_3$—$(CH_2)_2$—$CH$=$CH$—, $CH_3$—$(CH_2)_3$—$CH$=$CH$— or $CH_3$—$CH$=$CH$—$(CH_2)_2$—.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

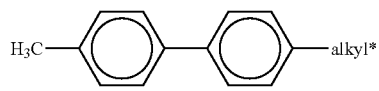

B1a

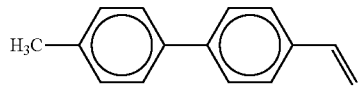

B2a

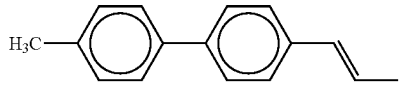

B2b

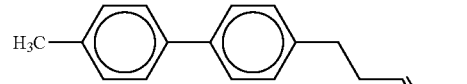

B2c in which alkyl* denotes an alkyl radical having 1-6 C atoms. The medium according to the invention particularly preferably comprises one or more compounds of the formulae B1a and/or B2c.

h) Mesogenic medium which additionally comprises one or more terphenyl compounds of the following formula:

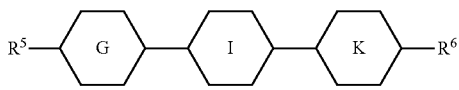

T in which $R^5$ and $R^6$ each, independently of one another, have one of the meanings indicated above, and

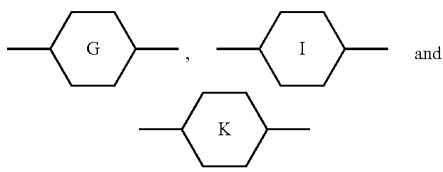

each, independently of one another, denote

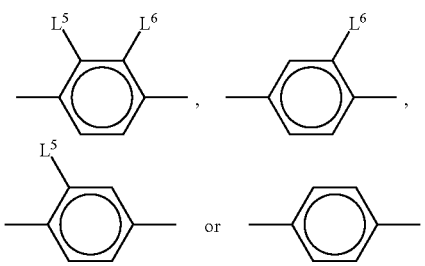

in which $L^5$ denotes F or Cl, preferably F, and $L^6$ denotes F, Cl, $OCF_3$, $CF_3$, $CH_3$, $CH_2F$ or $CHF_2$, preferably F.

The compounds of the formula T are preferably selected from the group consisting of the following sub-formulae:

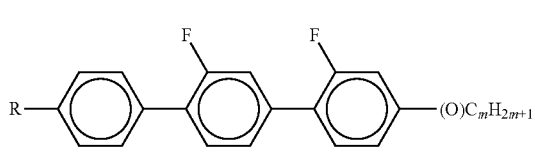

T1

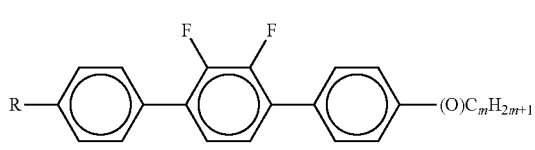

T2

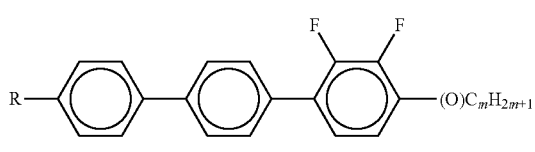

T3

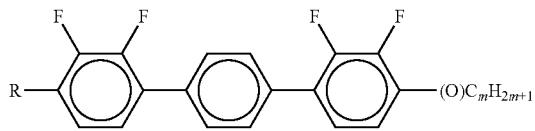

T4

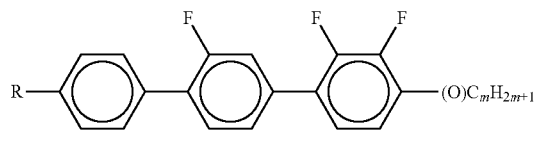
T5
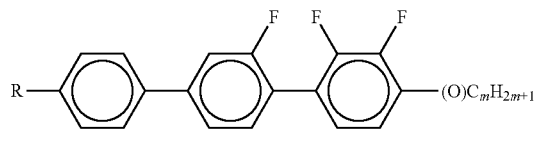
T6
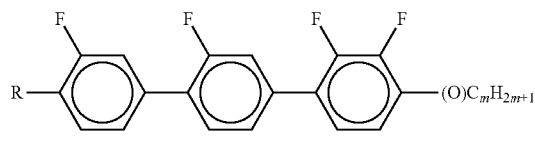
T7
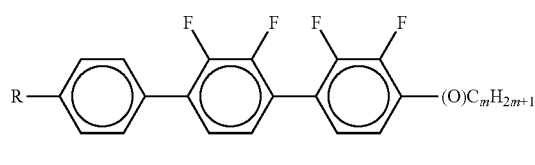
T8
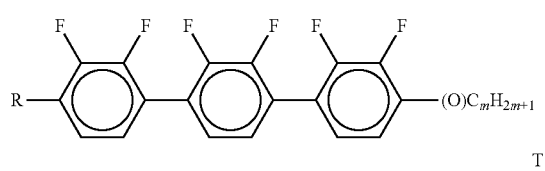
T9
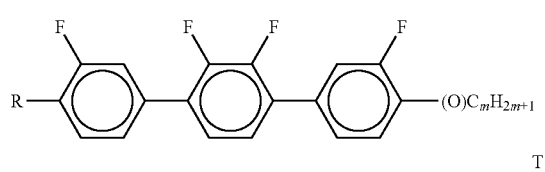
T10
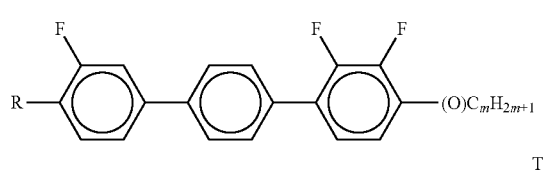
T11
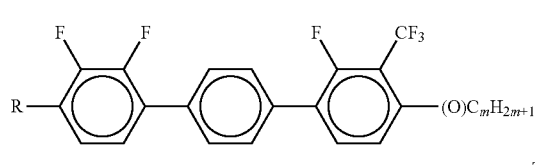
T12
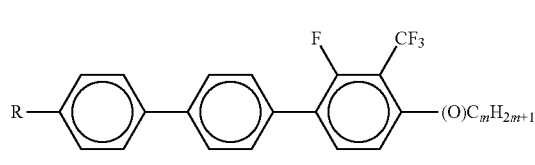
T13
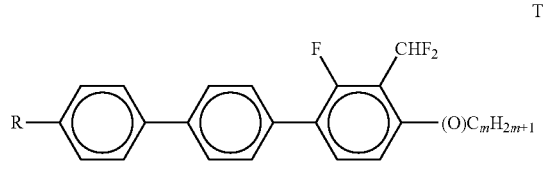
T14
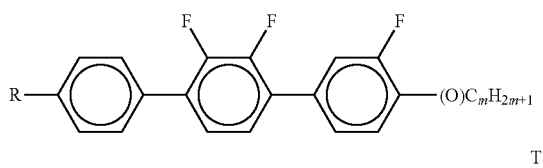
T15
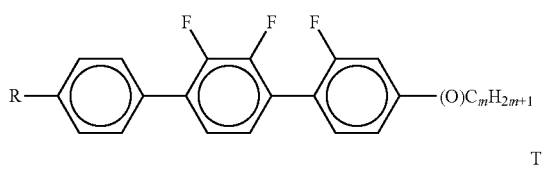
T16
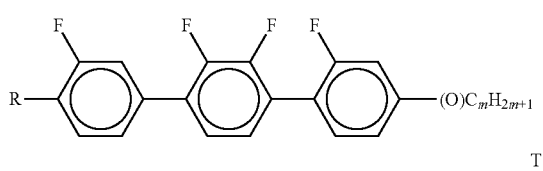
T17
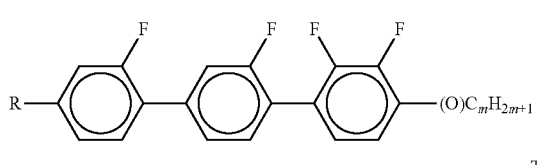
T18
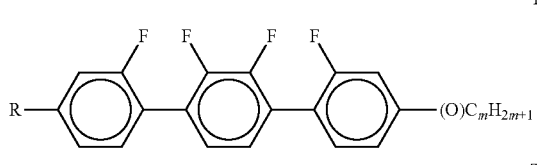
T19
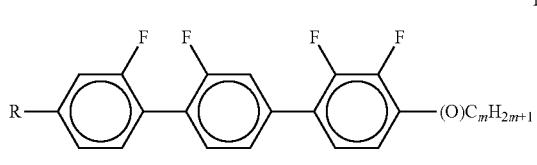
T20
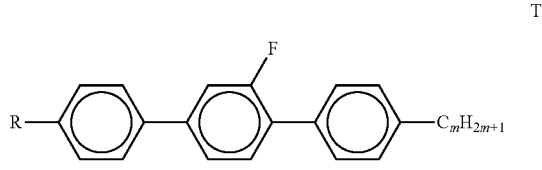
T21
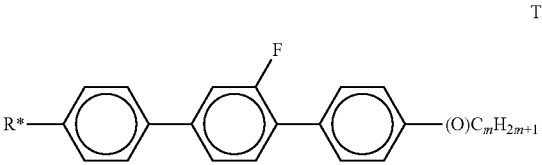
T22
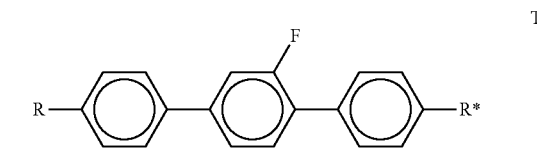
T23
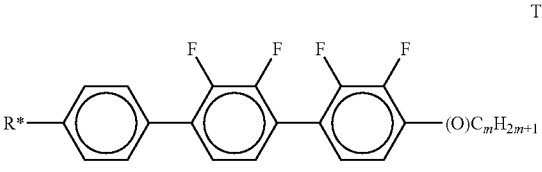
T24

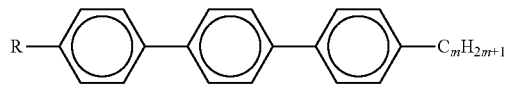 T25

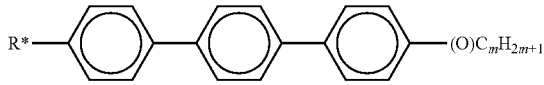 T26

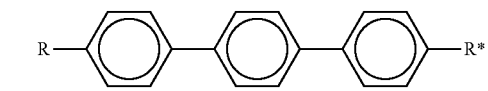 T27

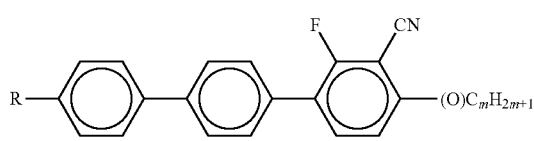 T28 in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

i) Mesogenic medium which additionally comprises one or more compounds of the following formula O:

$$R^{O1}-\boxed{H}-Z^{O1}-\boxed{M}-Z^{O2}-\left[\boxed{N}\right]_o-R^{O2}$$ O wherein $-\boxed{M}-$ denotes $-\boxed{\phantom{}}-$ , $-\boxed{\phantom{}}=$ or $=\boxed{\phantom{}}-$ , $-\boxed{N}-$ denotes

denotes

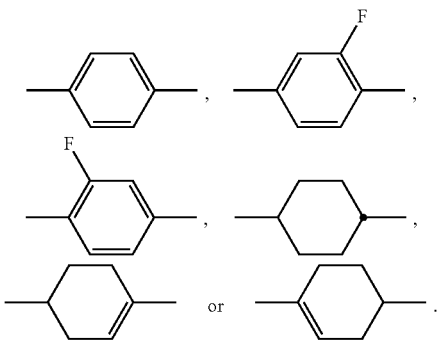

$R^{O1}$, $R^{O2}$ each, independently of one another, denote alkyl having 1 to 12 C atoms, where, in addition, one or two non-adjacent $CH_2$ groups may be replaced by $-O-$, $-CH=CH-$, $-CO-$, $-OCO-$ or $-COO-$ in such a way that O atoms are not linked directly to one another, $Z^{O1}$ denotes $-CH_2CH_2-$, $-CF_2CF_2-$, $-C\equiv C-$ or a single bond, $Z^{O2}$ denotes $CH_2O$, $-C(O)O-$, $-CH_2CH_2-$, $-CF_2CF_2-$, or a single bond, o is 1 or 2.

The compounds of the formula O are preferably selected from the group consisting of the following sub-formulae:

$R^{O1}-\boxed{H}-\boxed{H}-CH_2O-\boxed{H}-R^{O2}$ O1

$R^{O1}-\boxed{H}-\boxed{H}-\boxed{H}-CH_2O-\boxed{H}-\boxed{H}-R^{O2}$ O2

$R^{O1}-\boxed{H}-\boxed{H}-COO-\boxed{H}-R^{O2}$ O3

$R^{O1}-\boxed{H}-\boxed{H}-COO-\boxed{O}^F-R^{O2}$ O4

$R^{O1}-\boxed{H}-\boxed{H}-COO-\boxed{O}-\boxed{H}-R^{O2}$ O5

-continued

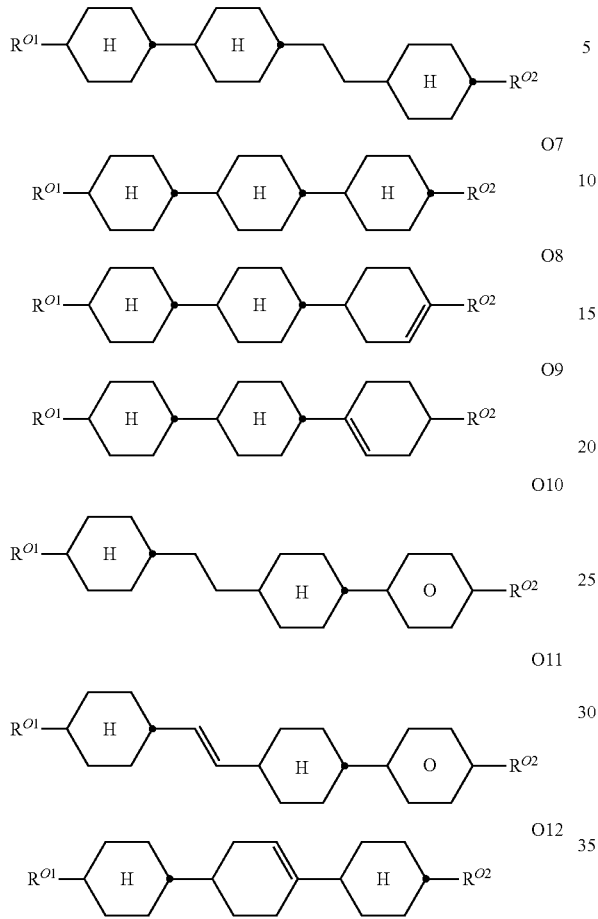

in which $R^{O1}$ and $R^{O2}$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O3, O4 and O5.

k) Mesogenic medium which additionally comprises one or more compounds of the following formula:

FI

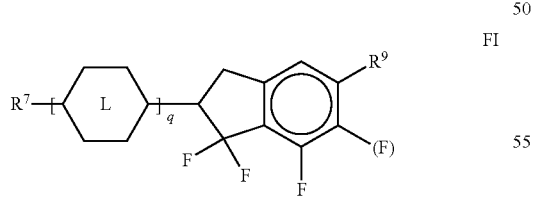

in which

denotes

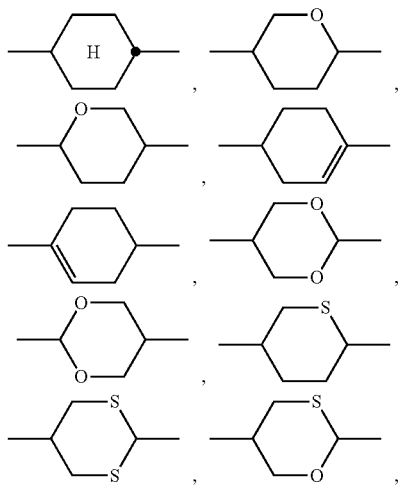

$R^9$ denotes H, $CH_3$, $C_2H_5$ or $n\text{-}C_3H_7$, (F) denotes an optional fluorine substituent, and q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

FI1

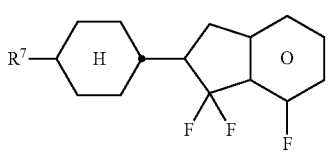

FI2

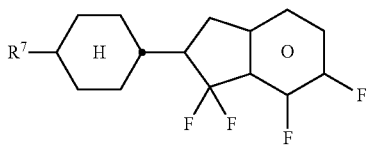

FI3

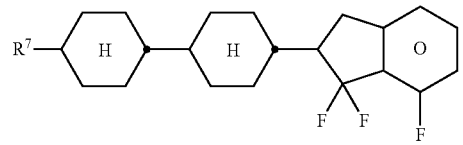

FI4

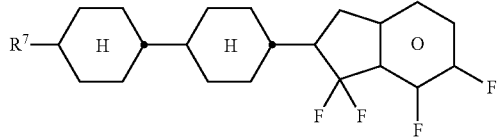

FI5

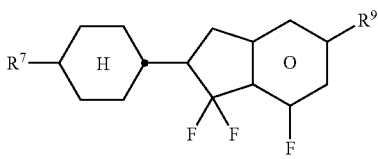

-continued

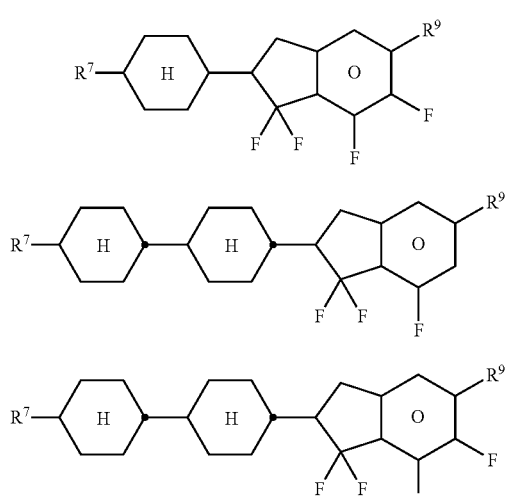

FI6
FI7
FI8 in which R⁷ preferably denotes straight-chain alkyl, and R⁹ denotes CH₃, C₂H₅ or n-C₃H₇. Particular preference is given to the compounds of the formulae FI1, FI2 and FI3.

l) Mesogenic medium which additionally comprises one or more compounds selected from the group consisting of the following formulae:

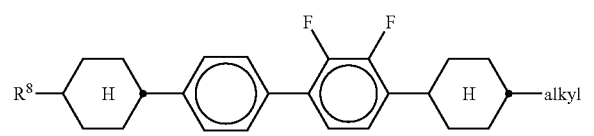

VK1

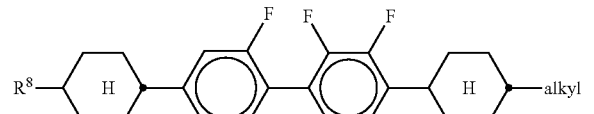

VK2

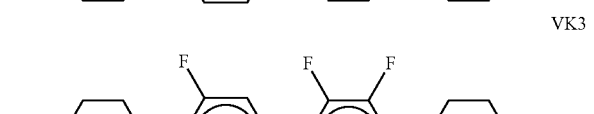

VK3

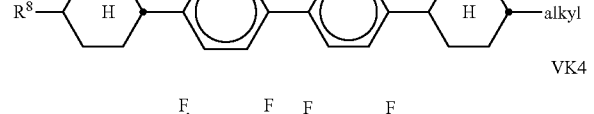

VK4 in which R⁸ has the meaning indicated for R¹, and alkyl denotes a straight-chain alkyl radical having 1-6 C atoms.

m) Mesogenic medium which additionally comprises one or more compounds which contain a tetrahydronaphthyl or naphthyl unit, such as, for example, the compounds selected from the group consisting of the following formulae:

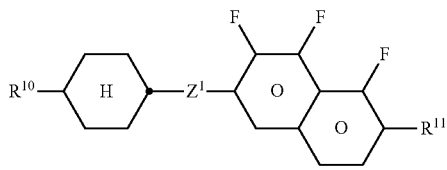

N1

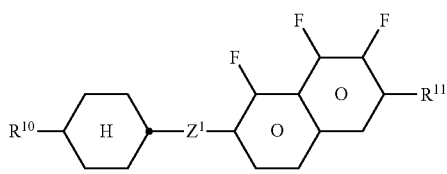

N2

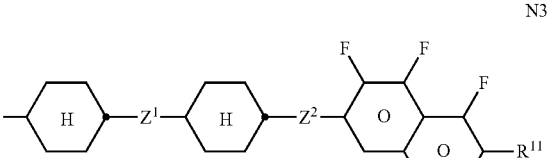

N3

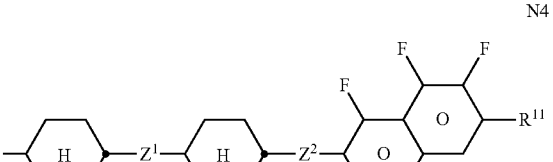

N4

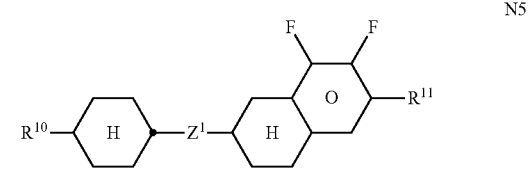

N5

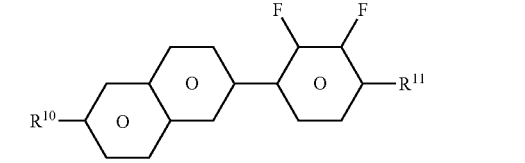

N6

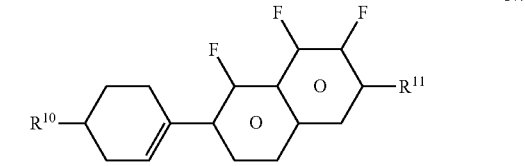

N7

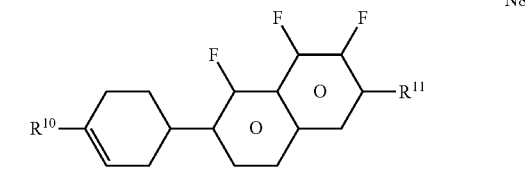

N8

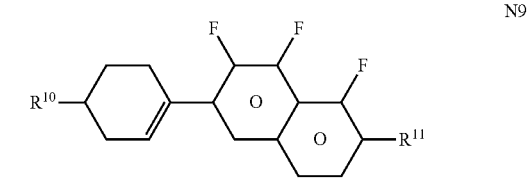

N9

-continued

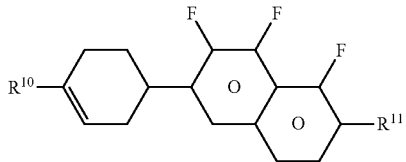
N10 in which
R$^{10}$ and R$^{11}$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, and R$^{10}$ and R$^{11}$ preferably denote straight-chain alkyl or alkoxy having 1 to 6 C atoms or straight-chain alkenyl having 2 to 6 C atoms, and Z$^1$ and Z$^2$ each, independently of one another, denote —C$_2$H$_4$—, —CH=CH—, —(CH$_2$)$_4$—, —(CH$_2$)$_3$O—, —O(CH$_2$)$_3$—, —CH=CH—CH$_2$CH$_2$—, —CH$_2$CH$_2$CH=CH—, —CH$_2$O—, —OCH$_2$—, —CO—O—, —O—CO—, —C$_2$F$_4$—, —CF=CF—, —CF=CH—, —CH=CF—, —CH$_2$— or a single bond.

n) Mesogenic medium which additionally comprises one or more difluorodibenzochromanes and/or chromanes of the following formulae:

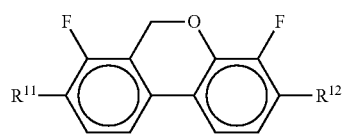
BC

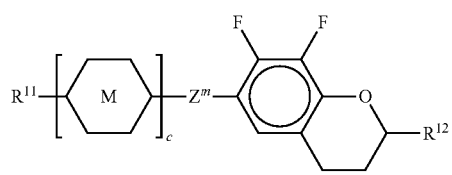
CR

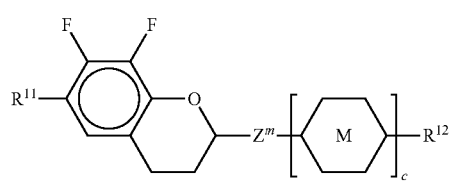
RC in which
R$^{11}$ and R$^{12}$ each, independently of one another, have one of the meanings indicated above for R$^{11}$,
ring M is trans-1,4-cyclohexylene or 1,4-phenylene,
Z$^m$—C$_2$H$_4$—, —CH$_2$O—, —OCH$_2$—, —CO—O— or —O—CO—,
c is 0, 1 or 2,
preferably in amounts of 3 to 20% by weight, in particular in amounts of 3 to 15% by weight.
Particularly preferred compounds of the formulae BC, CR and RC are selected from the group consisting of the following sub-formulae:

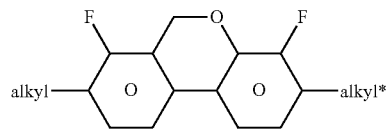
BC1

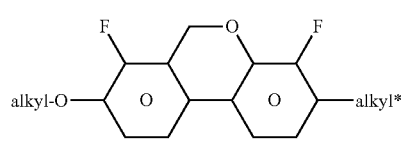
BC2

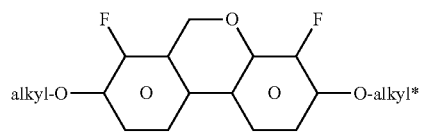
BC3

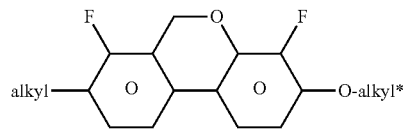
BC4

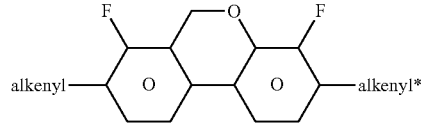
BC5

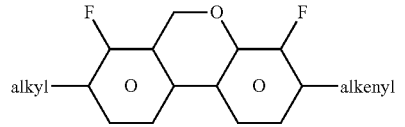
BC6

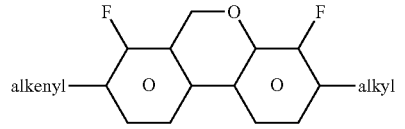
BC7

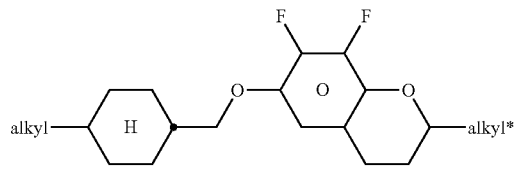
CR1

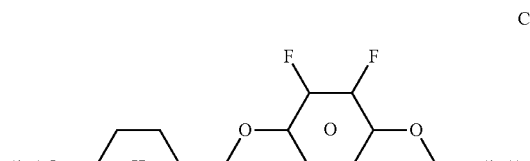
CR2

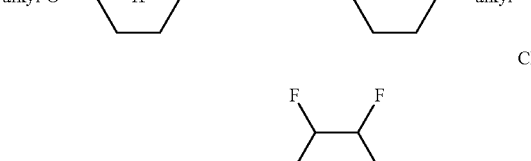
CR3

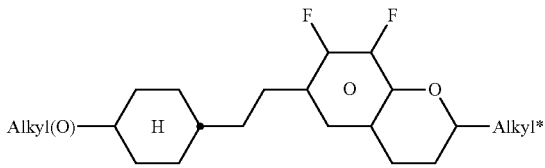

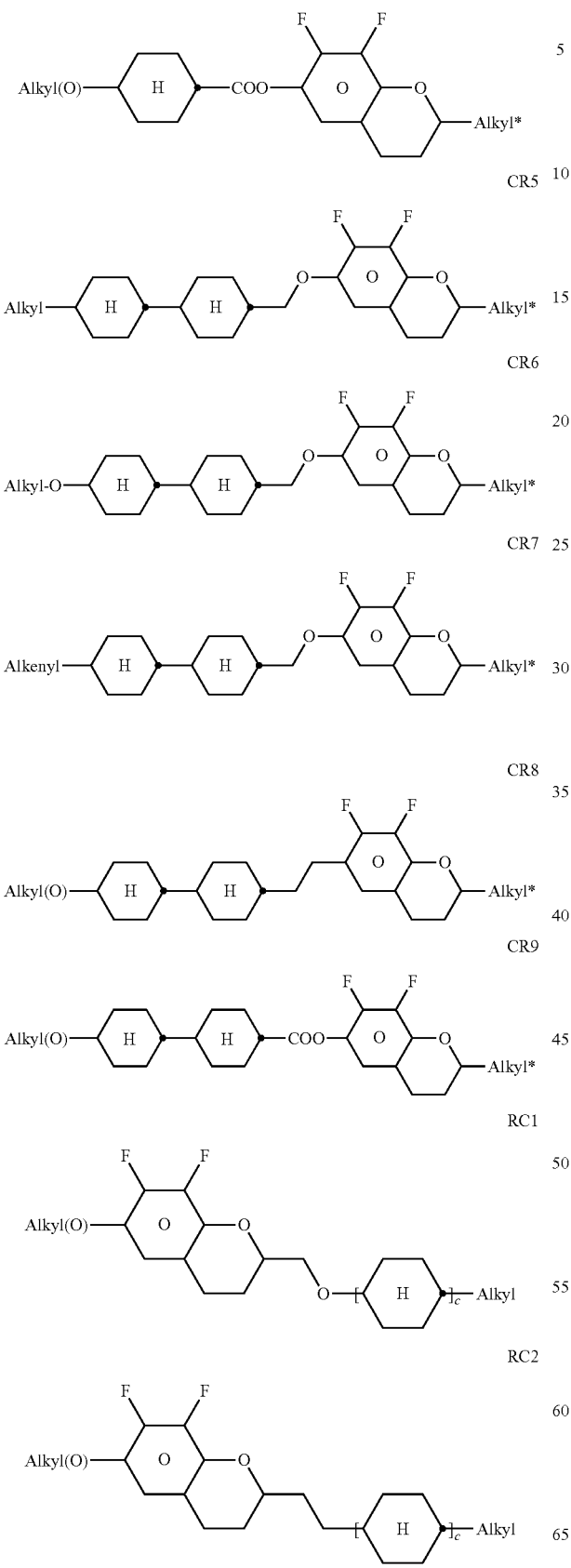

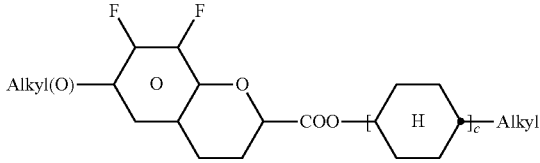

in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Very particular preference is given to mixtures comprising one, two or three compounds of the formula BC-2.

o) Mesogenic medium which additionally comprises one or more fluorinated phenanthrenes and/or dibenzofurans of the following formulae:

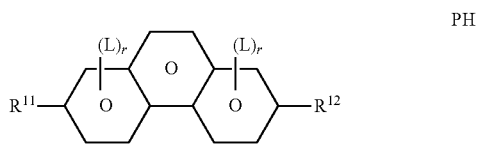

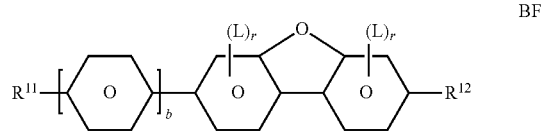

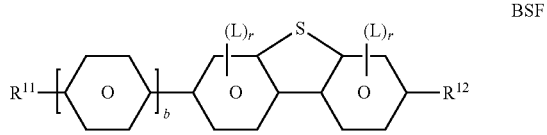

in which $R^{11}$ and $R^{12}$ each, independently of one another, have one of the meanings indicated above for $R^{11}$, b denotes 0 or 1, L denotes F, and r denotes 1, 2 or 3.

Particularly preferred compounds of the formulae PH and BF are selected from the group consisting of the following sub-formulae:

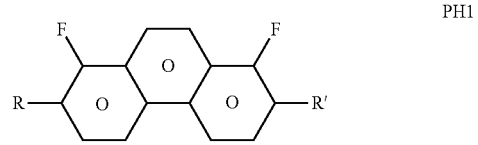

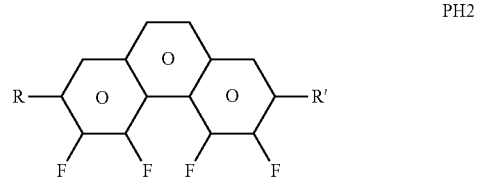

-continued

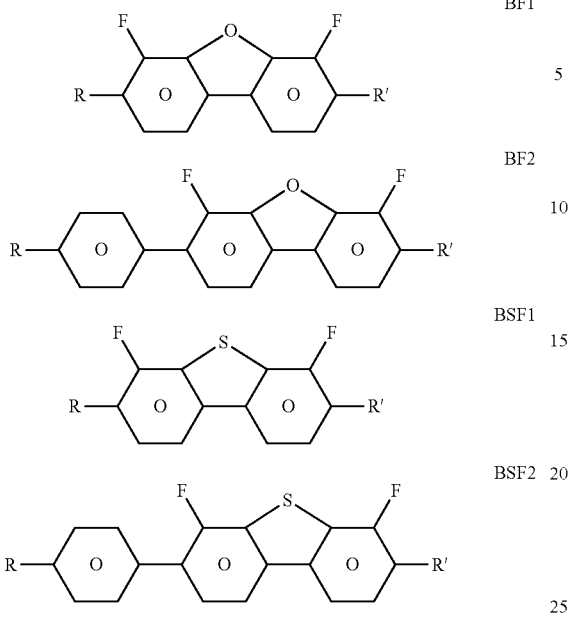

in which R and R' each, independently of one another, denote a straight-chain alkyl or alkoxy radical having 1-7 C atoms.

p) Mesogenic medium which additionally comprises one or more monocyclic compounds of the following formula

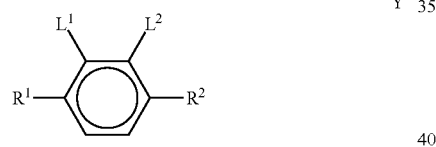

wherein $R^1$ and $R^2$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms, $L^1$ and $L^2$ each, independently of one another, denote F, Cl, $OCF_3$, $CF_3$, $CH_3$, $CH_2F$, $CHF_2$.

Preferably, both $L^1$ and $L^2$ denote F or one of $L^1$ and $L^2$ denotes F and the other denotes Cl, The compounds of the formula Y are preferably selected from the group consisting of the following sub-formulae:

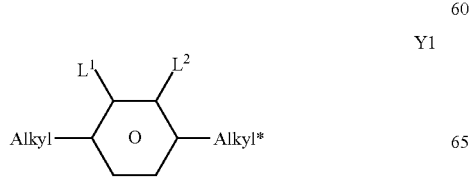

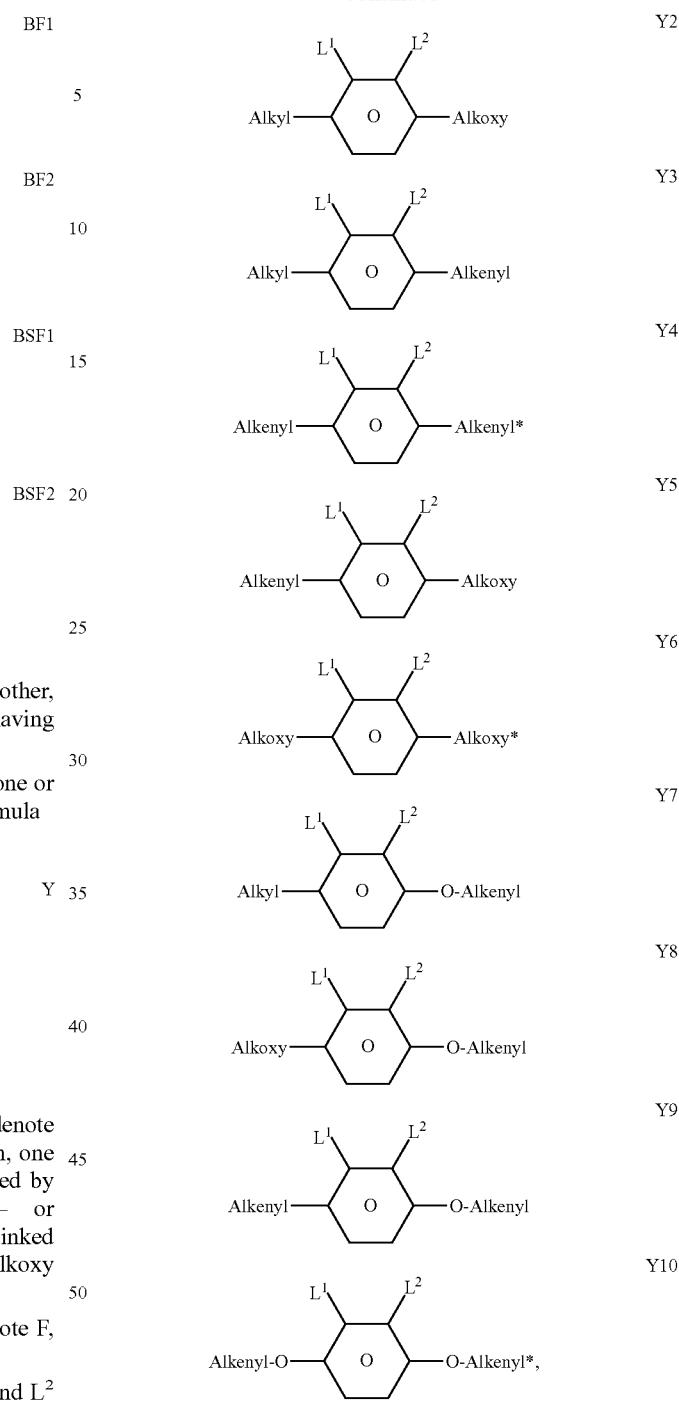

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

Particularly preferred compounds of the formula Y are selected from the group consisting of the following sub-formulae:

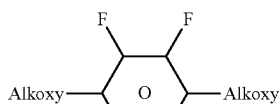
Y6A

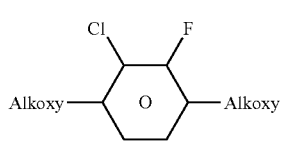
Y6B wherein Alkoxy preferably denotes straight-chain alkoxy with 3, 4, or 5 C atoms.

q) Mesogenic medium which comprises 1 to 15, preferably 3 to 12, compounds of the formulae CY1, CY2, PY1, PY2, AC1, AC2 and/or AC3. The proportion of these compounds in the mixture as a whole is preferably 20 to 99%, more preferably 30 to 95%, particularly preferably 40 to 90%. The content of these individual compounds is preferably in each case 2 to 20%.

r) Mesogenic medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

s) Mesogenic medium in which the proportion of compounds of the formulae CY, PY and ZK in the mixture as a whole is greater than 70%, preferably greater than 80%.

t) Mesogenic medium which contains one or more, preferably 1 to 5, compounds selected of formula PY1-PY8, very preferably of formula PY2. The proportion of these compounds in the mixture as a whole is preferably 1 to 30%, particularly preferably 2 to 20%. The content of these individual compounds is preferably in each case 1 to 20%.

u) Mesogenic medium which contains one or more, preferably 1, 2 or 3, compounds of formula T2. The content of these compounds in the mixture as a whole is preferably 1 to 20%.

The LC medium according to the invention preferably comprises the terphenyls of the formula T and the preferred sub-formulae thereof in an amount of 0.5-30% by weight, in particular 1-20% by weight. Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

v) Mesogenic medium which contains one or more, preferably 1, 2 or 3, compounds of formula BF1 and/or BSF1. The total content of these compounds in the mixture as a whole is preferably 1 to 15%, preferably 2 to 10% particularly preferably 4 to 8%.

v) Preferred media comprise one or more compounds of formula O, preferably selected from the formulae O3, O4 and O5 in a total concentration of 2 to 25%, preferably 3 to 20%, particularly preferably 5 to 15%.

w) Preferred media comprise one or more compounds of formula DK, preferably selected from the formulae DK1, DK4, DK7, DK 9, DK10 and DK11. The total concentration of compounds of formulae DK9, DK10 and DK11 is preferably 2 to 25%, more preferably 3 to 20%, particularly preferably 5 to 15%.

In another preferred embodiment of the present invention the LC medium contains an LC host mixture with positive dielectric anisotropy. Accordingly, in further preferred embodiments the mesogenic media according to the invention comprise components selected from the following items aa) to zz):

aa) Mesogenic medium which comprises one or more compounds selected from the group of compounds of the formulae II to VIII as set forth below, in particular of the formulae II and III

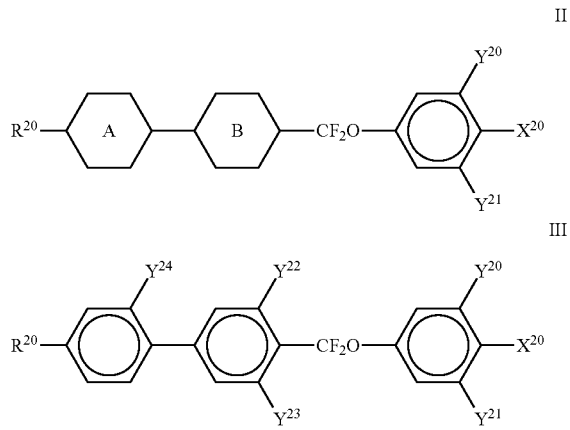

wherein
$R_{20}$ each, identically or differently, denote a halogenated or unsubstituted alkyl or alkoxy radical having 1 to 15 C atoms, where, in addition, one or more $CH_2$ groups in these radicals may each be replaced, independently of one another, by —C≡C—, —$CF_2O$—, —CH=CH—,

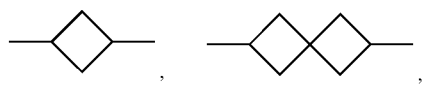

—O—, —CO—O— or —O—CO— in such a way that O atoms are not linked directly to one another,
$X^{20}$ each, identically or differently, denote F, Cl, CN, $SF_5$, SCN, NCS, a halogenated alkyl radical, a halogenated alkenyl radical, a halogenated alkoxy radical or a halogenated alkenyloxy radical, each having up to 6 C atoms, and
$Y^{20-24}$ each, identically or differently, denote H or F;

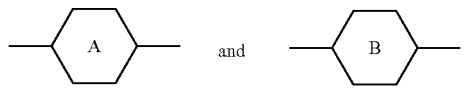

each, independently of one another, denote

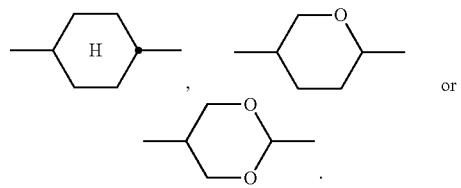

, or

The compounds of the formula II are preferably selected from the following formulae:

IIa
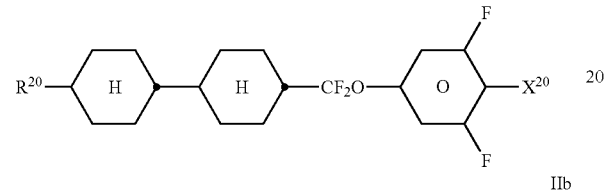

IIb
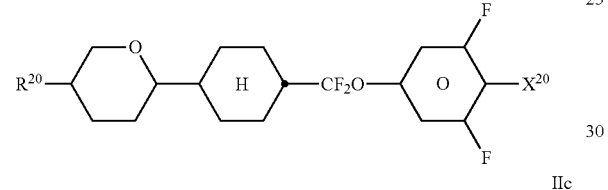

IIc
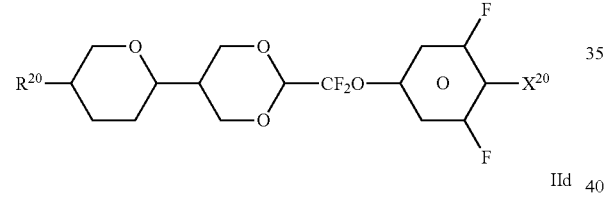

IId
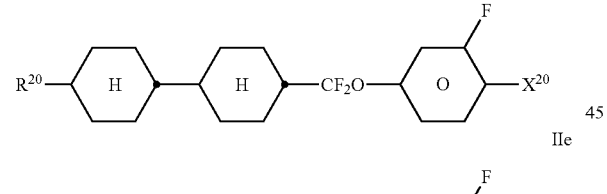

IIe
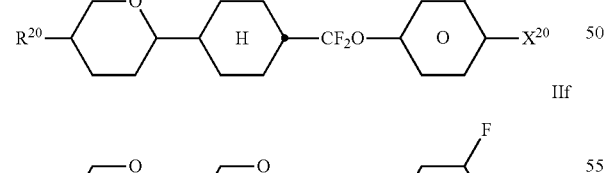

IIf
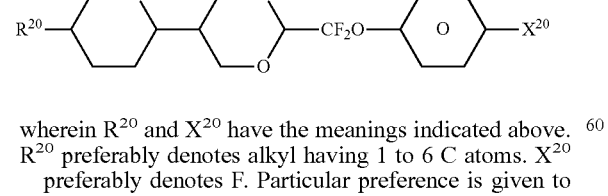

wherein $R^{20}$ and $X^{20}$ have the meanings indicated above. $R^{20}$ preferably denotes alkyl having 1 to 6 C atoms. $X^{20}$ preferably denotes F. Particular preference is given to compounds of the formulae IIa and IIb, in particular compounds of the formulae IIa and IIb wherein X denotes F.

The compounds of the formula III are preferably selected from the following formulae:

IIIa
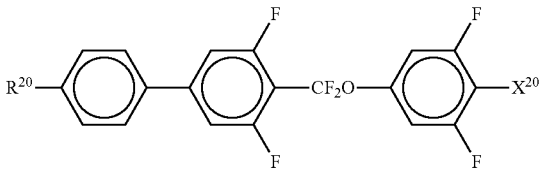

IIIb
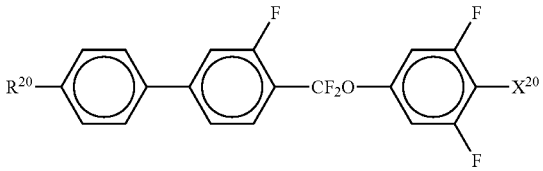

IIIc
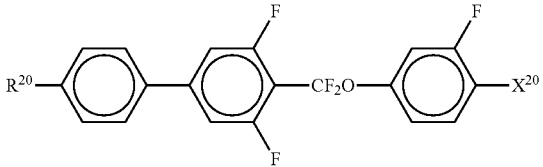

IIId
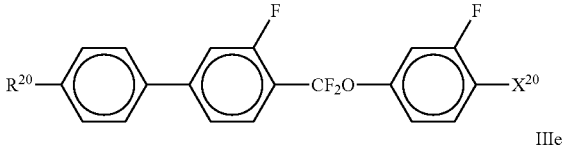

IIIe
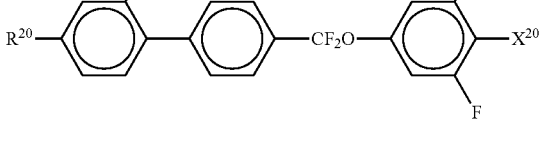

wherein $R^{20}$ and $X^{20}$ have the meanings indicated above.

$R^{20}$ preferably denotes alkyl having 1 to 6 C atoms. $X^{20}$ preferably denotes F. Particular preference is given to compounds of the formulae IIIa and IIIe, in particular compounds of the formula IIIa;

bb) Mesogenic medium alternatively or additionally comprising one or more compounds selected from the following formulae:

IV
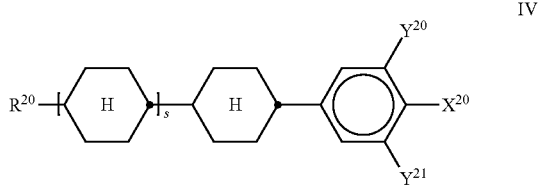

V
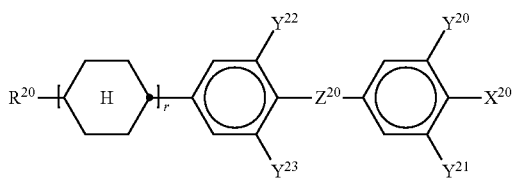

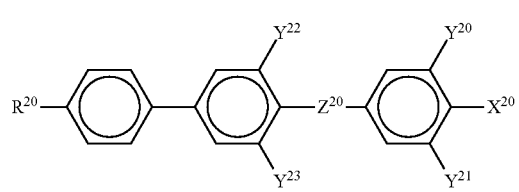
VI

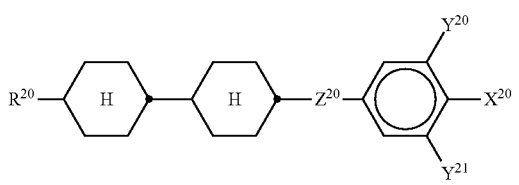
VII

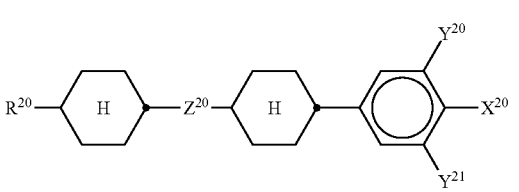
VIII wherein
$R^{20}$, $X^{20}$ and $Y^{20\text{-}23}$ have the meanings indicated above, and
$Z^{20}$ denotes —$C_2H_4$—, —$(CH_2)_4$—, —CH=CH—, —CF=CF—, —$C_2F_4$—, —$CH_2CF_2$—, —$CF_2CH_2$—, —$CH_2O$—, —$OCH_2$—, —COO— or —$OCF_2$—, in formulae V and VI also a single bond, in formulae V and VIII also —$CF_2O$—,
r denotes 0 or 1, and
s denotes 0 or 1;

The compounds of the formula IV are preferably selected from the following formulae:

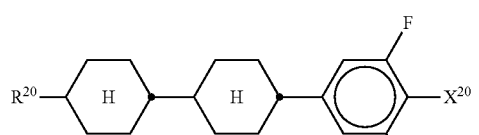
IVa

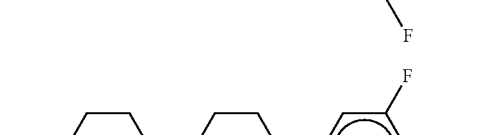
IVb

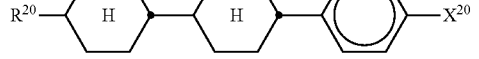
IVc

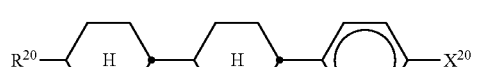
IVd

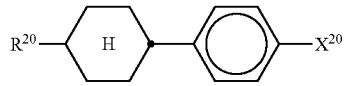

wherein $R^{20}$ and $X^{20}$ have the meanings indicated above. $R^{20}$ preferably denotes alkyl having 1 to 6 C atoms. $X^{20}$ preferably denotes F, CN or $OCF_3$, furthermore OCF=$CF_2$ or Cl;

The compounds of the formula V are preferably selected from the following formulae:

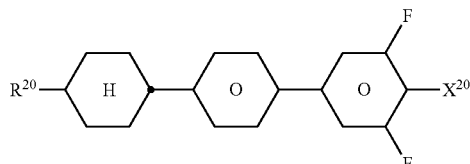
Va

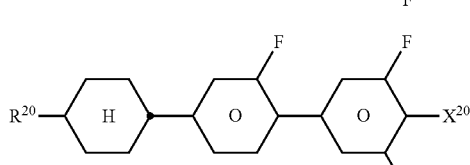
Vb

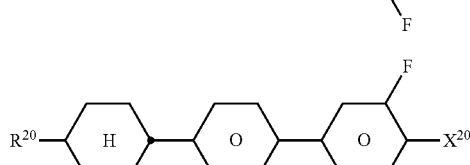
Vc

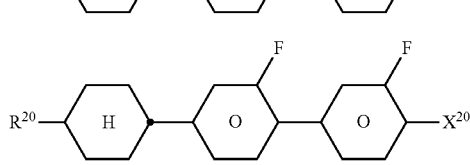
Vd

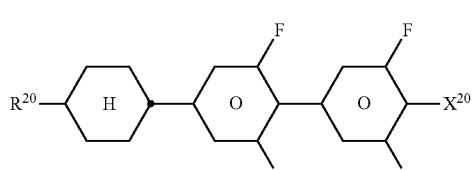
Ve

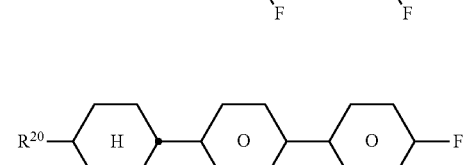
Vf

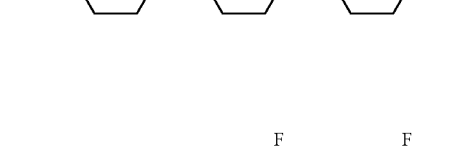
Vg

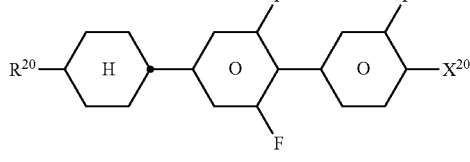
Vh

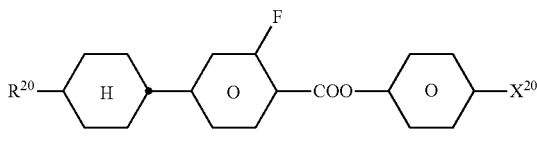

wherein $R^{20}$ and $X^{20}$ have the meanings indicated above. $R^{20}$ preferably denotes alkyl having 1 to 6 C atoms. $X^{20}$ preferably denotes F and $OCF_3$, furthermore $OCHF_2$, $CF_3$, OCF=$CF_2$ and OCH=$CF_2$;

The compounds of the formula VI are preferably selected from the following formulae:

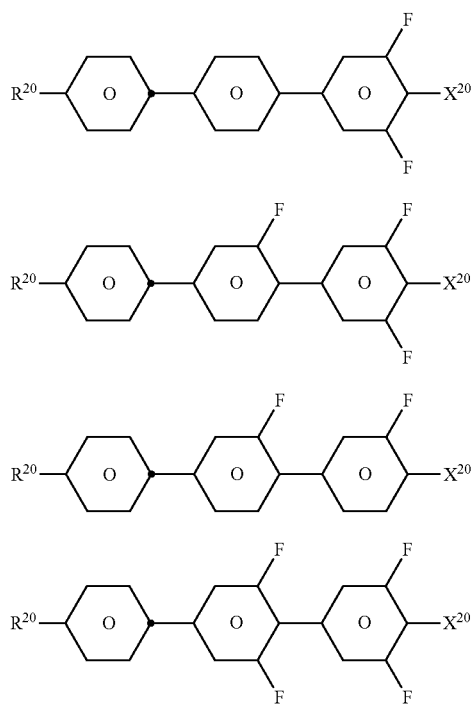

wherein $R^{20}$ and $X^{20}$ have the meanings indicated above. $R^{20}$ preferably denotes alkyl having 1 to 6 C atoms. $X^{20}$ preferably denotes F, furthermore OCF$_3$, CF$_3$, CF=CF$_2$, OCHF$_2$ and OCH=CF$_2$;

The compounds of the formula VII are preferably selected from the following formulae:

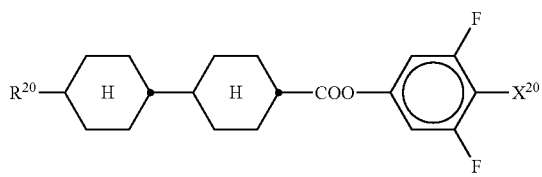

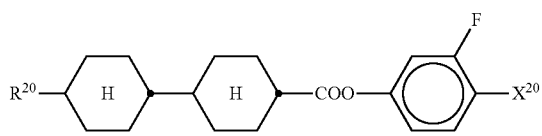

wherein $R^{20}$ and $X^{20}$ have the meanings indicated above. $R^{20}$ preferably denotes alkyl having 1 to 6 C atoms. $X^{20}$ preferably denotes F, furthermore OCF$_3$, OCHF$_2$ and OCH=CF$_2$.

cc) Mesogenic medium which additionally comprises one or more compounds selected from the formulae ZK1 to ZK10 given above. Especially preferred are compounds of formula ZK1 and ZK3. Particularly preferred compounds of formula ZK are selected from the sub-formulae ZK1a, ZK1b, ZK1c, ZK3a, ZK3b, ZK3c and ZK3d.

dd) The mesogenic medium additionally comprises one or more compounds selected from the formulae DK1 to DK12 given above. Especially preferred compounds are DK1, DK4, DK7, DK 9, DK10 and DK11.

ee) The mesogenic medium additionally comprises one or more compounds selected from the following formula:

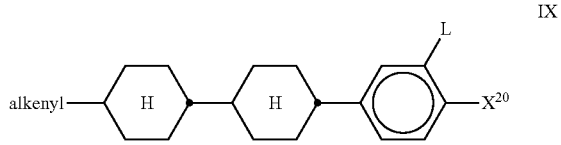

wherein $X^{20}$ has the meanings indicated above,
L denotes H or F, and
"alkenyl" denotes C$_{2-6}$-alkenyl.

ff) The compounds of the formulae DK-3a and IX are preferably selected from the following formulae:

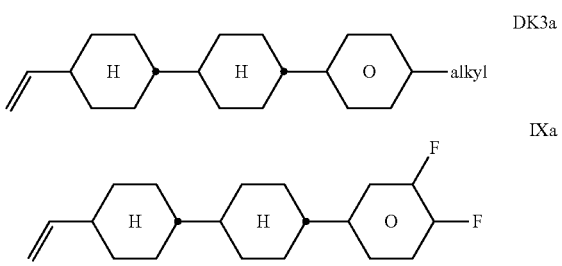

wherein "alkyl" denotes C$_{1-6}$-alkyl, preferably n-C$_3$H$_7$, n-C$_4$H$_9$ or n-C$_5$H$_{11}$, in particular n-C$_3$H$_7$.

gg) The medium additionally comprises one or more compounds selected from the formulae B1, B2 and B3 given above, preferably from the formula B2. The compounds of the formulae B1 to B3 are particularly preferably selected from the formulae B1a, B2a, B2b and B2c.

hh) The medium additionally comprises one or more compounds selected from the following formula:

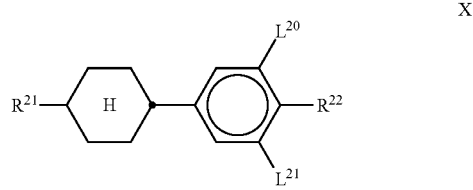

wherein $L^{20}$, $L^{21}$ denote H or F, and $R^{21}$ and $R^{22}$ each, identically or differently, denote n-alkyl, alkoxy, oxaalkyl, fluoroalkyl or alkenyl, each having up to 6 C atoms, and preferably each, identically or differently, denote alkyl having 1 to 6 C atoms.

ii) The medium comprises one or more compounds of the following formulae:

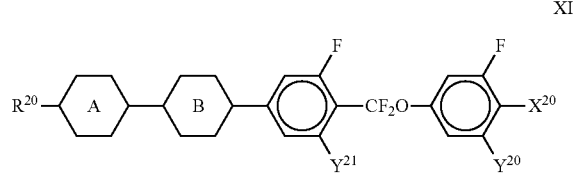

XII
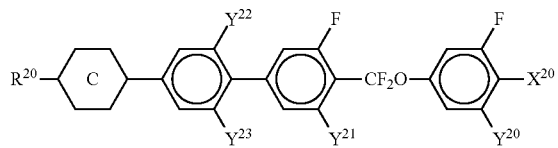
wherein $R^{20}$, $X^{20}$ and $Y^{20-23}$ have the meanings indicated in formula III, and
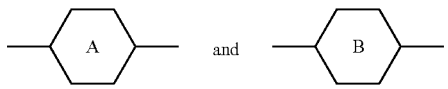
each, independently of one another, denote
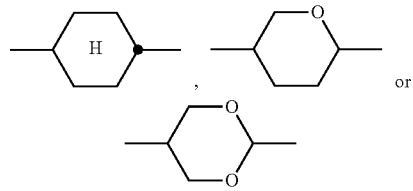
and
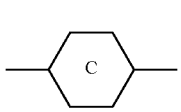
denotes
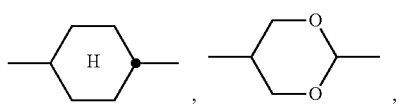
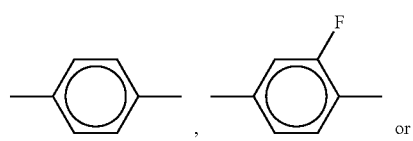
or
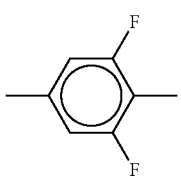
The compounds of the formulae XI and XII are preferably selected from the following formulae:
XIa
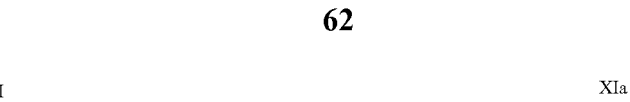
XIb
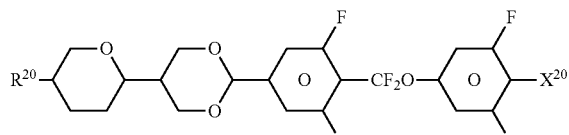
XIc
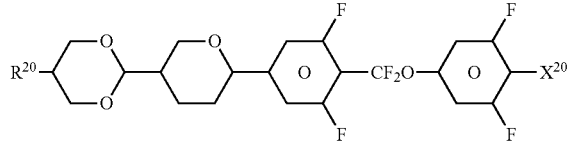
XId
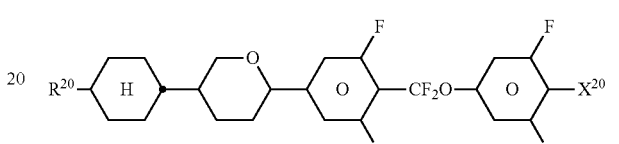
XIe
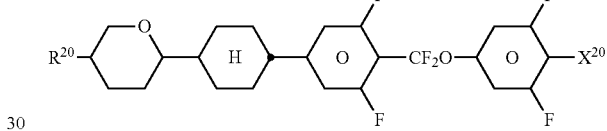
XIf
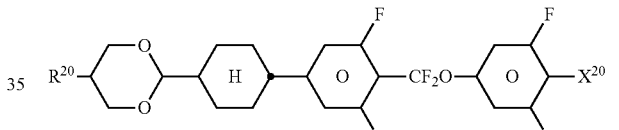
XIIa
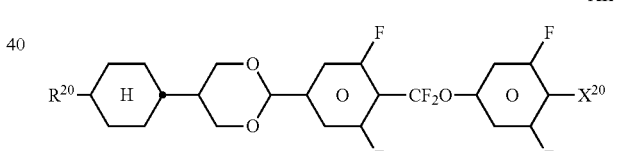
XIIb
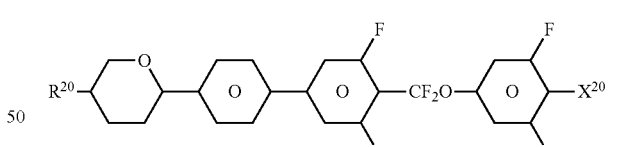
XIIc
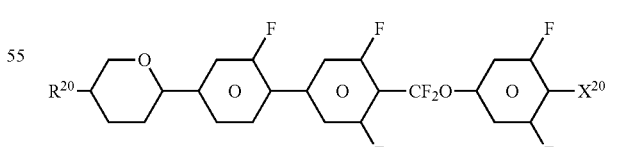
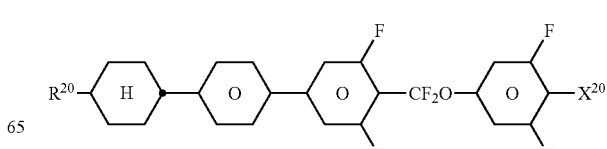

XIId
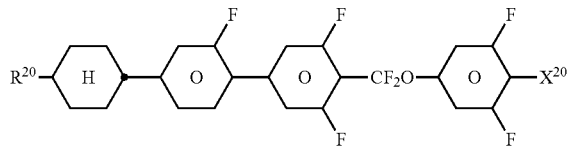

XIIe
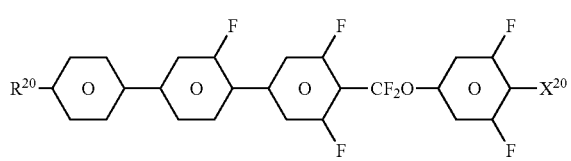

XIIf
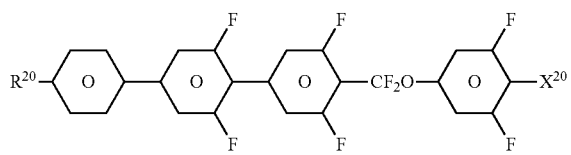

wherein $R^{20}$ and $X^{20}$ have the meaning indicated above and preferably $R^{20}$ denotes alkyl having 1 to 6 C atoms and $X^{20}$ denotes F.

The mixture according to the invention particularly preferably comprises at least one compound of the formula XIIa and/or XIIe.

jj) The medium comprises one or more compounds of formula T given above, preferably selected from the group of compounds of the formulae T21 to T23 and T25 to T27.

Particular preference is given to compounds of the formulae T21 to T23. Very particular preference is given to the compounds of the formulae

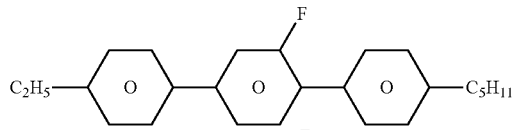

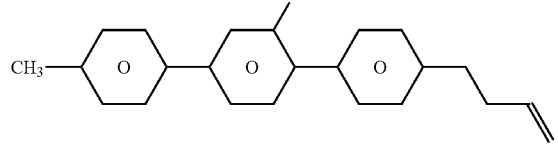

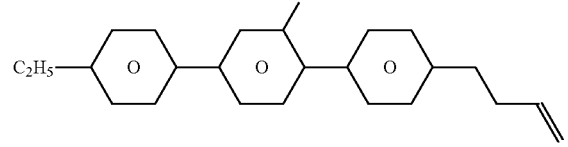

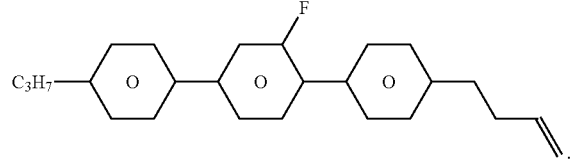

kk) The medium comprises one or more compounds selected from the group of formulae DK9, DK10 and DK11 given above.

ll) The medium additionally comprises one or more compounds selected from the following formulae:

XIII
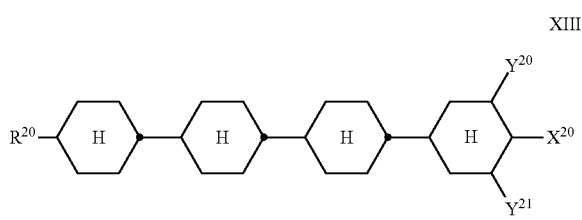

XIV
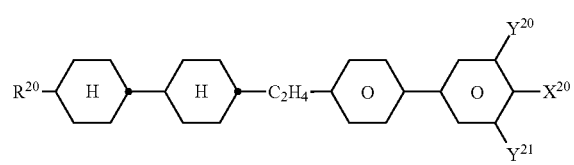

XV
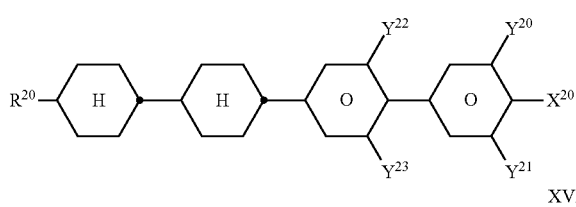

XVI
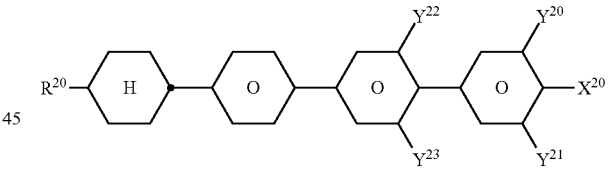

XVII
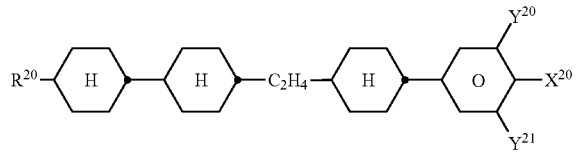

XVIII
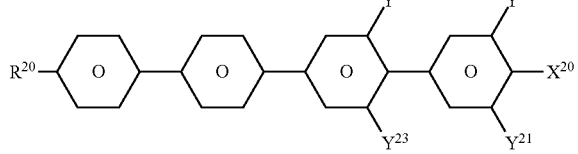

wherein $R^{20}$ and $X^{20}$ each, independently of one another, have one of the meanings indicated above, and $Y^{20-23}$ each, independently of one another, denote H or F. $X^{20}$ is preferably F, Cl, $CF_3$, $OCF_3$ or $OCHF_2$. $R^{20}$ preferably denotes alkyl, alkoxy, oxaalkyl, fluoroalkyl or alkenyl, each having up to 6 C atoms.

The mixture according to the invention particularly preferably comprises one or more compounds of the formula XVIII-a,

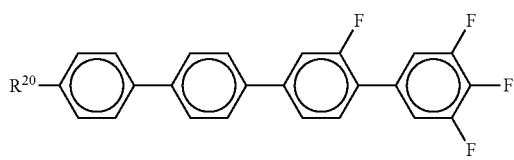

XVIII-a wherein $R^{20}$ has the meanings indicated above. $R^{20}$ preferably denotes straight-chain alkyl, in particular ethyl, n-propyl, n-butyl and n-pentyl and very particularly preferably n-propyl. The compound(s) of the formula XVIII, in particular of the formula XVIII-a, is (are) preferably employed in the mixtures according to the invention in amounts of 0.5-20% by weight, particularly preferably 1-15% by weight.

mm) The medium additionally comprises one or more compounds of the formula XIX,

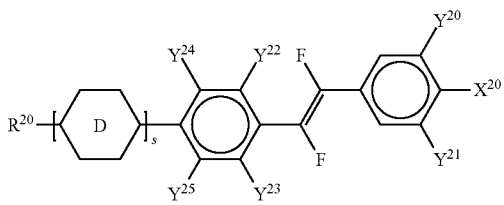

XIX wherein $R^{20}$, $X^{20}$ and $Y^{20-25}$ have the meanings indicated in formula III, s denotes 0 or 1, and

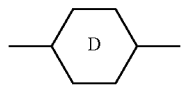

denotes

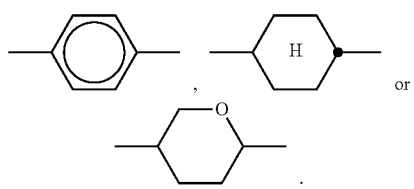

, or

In the formula XIX, $X^{20}$ may also denote an alkyl radical having 1-6 C atoms or an alkoxy radical having 1-6 C atoms. The alkyl or alkoxy radical is preferably straight-chain.

$R^{20}$ preferably denotes alkyl having 1 to 6 C atoms. $X^{20}$ preferably denotes F;

The compounds of the formula XIX are preferably selected from the following formulae:

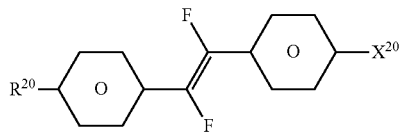

XIXa

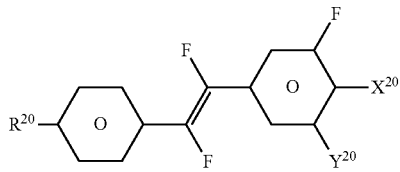

XIXb

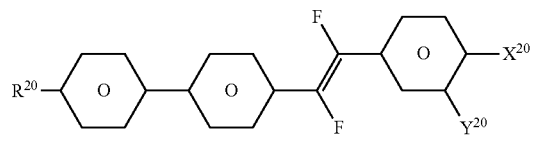

XIXc

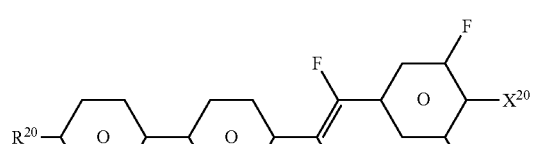

XIXd

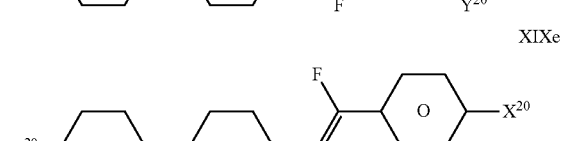

XIXe

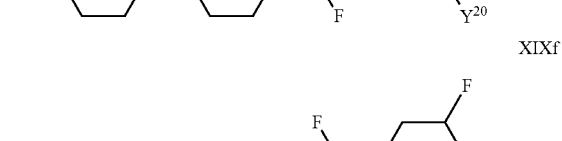

XIXf

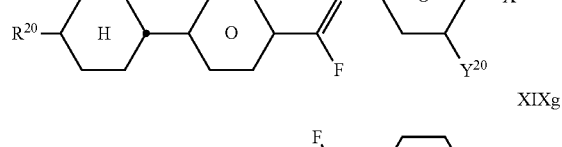

XIXg

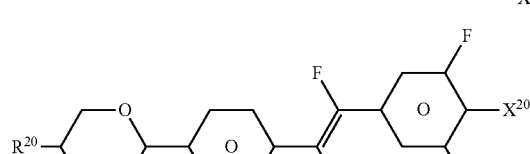

XIXh wherein $R^{20}$, $X^{20}$ and $Y^{20}$ have the meanings indicated above. $R^{20}$ preferably denotes alkyl having 1 to 6 C atoms. $X^{20}$ preferably denotes F, and $Y^{20}$ is preferably F;

is preferably

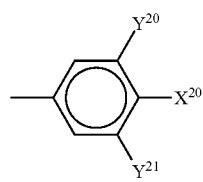

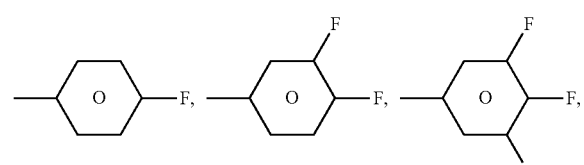

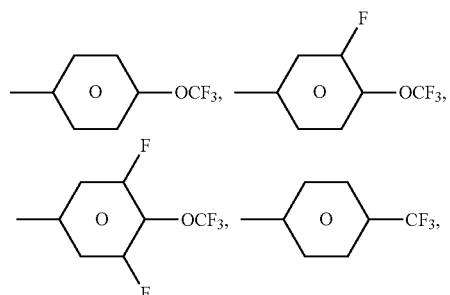

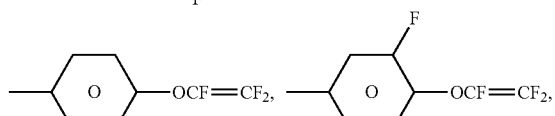

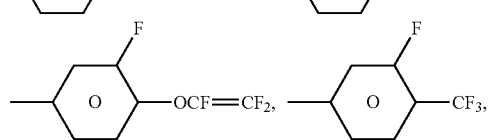

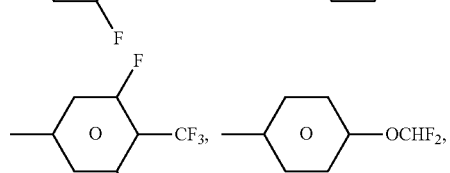

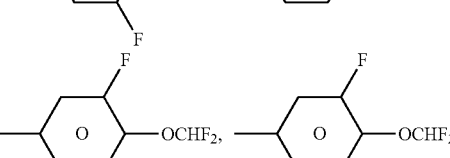

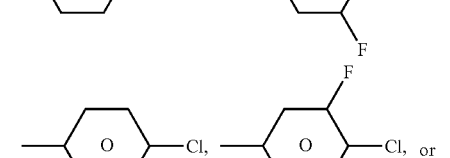

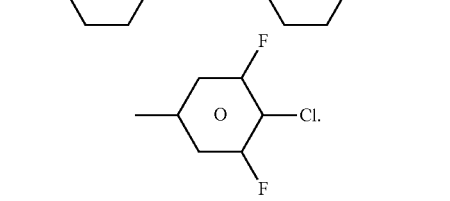

$R^{20}$ is straight-chain alkyl or alkenyl having 2 to 6 C atoms.

nn) The medium comprises one or more compounds of the formulae G1 to G4 given above, preferably selected from G1 and G2 wherein alkyl denotes $C_{1-6}$-alkyl, $L^x$ denotes H and X denotes F or Cl. In G2, X particularly preferably denotes Cl.

oo) The medium comprises one or more compounds of the following formulae:

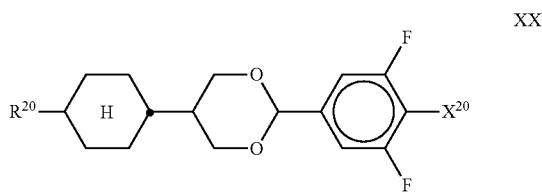

XX

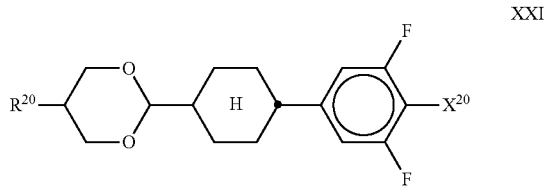

XXI

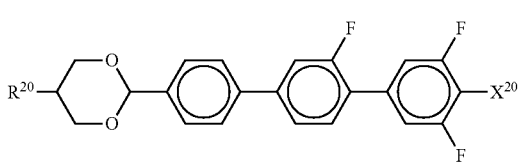

XXII wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula XXII wherein $X^{20}$ preferably denotes F. The compound(s) of the formulae XX-XXII is (are) preferably employed in the mixtures according to the invention in amounts of 1-20% by weight, particularly preferably 1-15% by weight. Particularly preferred mixtures comprise at least one compound of the formula XXII.

pp) The medium comprises one or more compounds of the following pyrimidine or pyridine compounds of the formulae

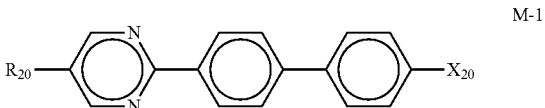

M-1

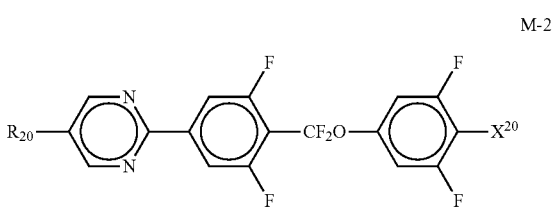

M-2

M-3

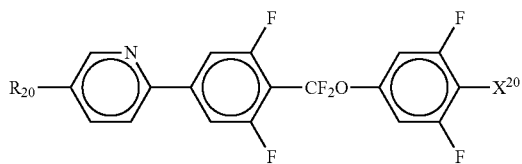

wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula M-1, wherein $X^{20}$ preferably denotes F. The compound(s) of the formulae M-1-M-3 is (are) preferably employed in the mixtures according to the invention in amounts of 1-20% by weight, particularly preferably 1-15% by weight.

qq) The medium comprises two or more compounds of the formula XII, in particular of the formula XIIa and/or XIIe.

rr) The medium comprises 2-30% by weight, preferably 3-20% by weight, particularly preferably 3-15% by weight, of compounds of the formula XII.

ss) Besides the compounds of the formulae XII, the medium comprises further compounds selected from the group of the compounds of the formulae II-XVIII.

tt) The proportion of compounds of the formulae II-XVIII in the mixture as a whole is 40 to 95%, preferably 50 to 90%, particularly preferably 55 to 88% by weight.

uu) The medium preferably comprises 10-40%, more preferably 12-30%, particularly preferably 15 to 25% by weight of compounds of the formulae II and/or III.

vv) The medium comprises 1-10% by weight, particularly preferably 2-7% by weight, of compounds of the formula XV and/or XVI.

ww) The medium comprises at least one compound of the formula XIIa and/or at least one compound of the formula XIIe and at least one compound of the formula IIIa and/or IIa.

xx) Preferred media comprise one or more compounds of formula O, preferably selected from the formulae O3, O4 and O5 in a total concentration of 2 to 25%, preferably 3 to 20%, particularly preferably 5 to 15%.

yy) Preferred media comprise one or more compounds of formula DK, preferably selected from the formulae DK1, DK4, DK7, DK 9, DK10 and DK11. The total concentration of compounds of formulae DK9, DK10 and DK11 is preferably 2 to 25%, more preferably 3 to 20%, particularly preferably 5 to 15%.

zz) Preferred media comprise one or more compounds of formulae IV to VI, preferably selected from the group of compounds of formulae IVa, IVb, IVc, IVd, Va, Vc and VIb in a concentration of 10 to 80%, preferably 12 to 75% particularly preferably 15 to 70% by weight.

In case the medium has negative dielectric anisotropy, the value for the dielectric anisotropy ($\Delta\varepsilon$) is preferably in the range from −2.0 to −8.0, more preferably in the range from −3.0 to −6.0, and particularly preferably from −3.5 to −5.0.

In case the medium has positive dielectric anisotropy, the value for $\Delta\varepsilon$ is preferably in the range from 3.0 to 60.0, more preferably in the range from 5.0 to 30.0, and particularly preferably from 8.0 to 15.0.

The liquid-crystal media in accordance with the present invention preferably have a clearing point of 70° C. or more, more preferably 80° C. or more, even more preferably 90° C. or more, still more preferably 105° C. or more, and particularly preferably 110° C. or more.

The nematic phase of the media according to the invention preferably extends at least from −10° C. or less to 80° C. or more. An even broader nematic phase range is more preferred, in particular extending up to 90° C. or more, more preferably extending at least from −20° C. or less to 100° C. or more and particularly preferably extending from −30° C. or less to 110° C. or more.

In a preferred embodiment of the present invention the birefringence ($\Delta n$) of the liquid crystal media is in the range of 0.040 or more to 0.080 or less, more preferably in the range of 0.045 or more to 0.070 or less and most preferably in the range of 0.050 or more to 0.060 or less. In this embodiment, the dielectric anisotropy is positive or negative, preferably negative.

In another preferred embodiment of the present invention the $\Delta n$ of the liquid crystal media is n the range of 0.075 or more to 0.130 or less, more preferably in the range of 0.090 or more to 0.125 or less and most preferably in the range of 0.095 or more to 0.120 or less.

In yet another preferred embodiment of the present invention the $\Delta n$ of the liquid crystal media is in the range of 0.100 or more to 0.200 or less, more preferably in the range of 0.110 or more to 0.180 or less and most preferably in the range of 0.120 or more to 0.160 or less.

The one or more compounds selected from the group of compounds of formulae Ia, Ib and Ic as set forth above and below are preferably present in the mesogenic medium in a proportion of 0.01% by weight to 15% by weight, more preferably 0.025% by weight to 10% by weight, even more preferably 0.05% by weight to 7.5% by weight and particularly preferably 0.1% by weight to 5% by weight.

In an embodiment where two or more compounds selected from the group of compounds of formulae Ia, Ib and Ic as set forth above and below are present in the mesogenic medium, the total concentration of these compounds in the medium is particularly preferably in the range of 0.05% by weight to 15% by weight and even more preferably 0.1% by weight to 10% by weight. In this case it is particularly preferred that an individual dye compound is present in the medium in a concentration in the range of 0.025% by weight to 5% by weight and even more preferably 0.05% by weight to 2.5% by weight and in particular 0.1% by weight to 1% by weight.

The media preferably comprise one, two, three, four, five, six, seven, eight or nine compounds of formula Ia, Ib and/or Ic according to the invention. In a particular embodiment the medium comprises at least three compounds selected from the group of compounds of formulae Ia, Ib and Ic.

The LC medium according to the invention preferably is a nematic liquid crystal.

The media according to the invention are prepared in a manner conventional per se. In general, the components are dissolved in one another, preferably at elevated temperature. The mixing is preferably carried out under inert gas, for example under nitrogen or argon. One or more dyes of formula Ia, Ib and/or Ic and optionally further dichroic dyes are subsequently added, preferably at elevated temperature, more preferably at above 40° C. and particularly preferably at above 50° C. In general, the desired amount of the components used in smaller amount is dissolved in the components making up the principal constituent. It is also possible to mix solutions of the components in an organic solvent, for example in acetone, toluene, chloroform or methanol, and to remove the solvent again, for example by distillation, after mixing.

The invention furthermore relates to a process for the preparation of the mesogenic media according to the invention.

The invention furthermore relates to the use of an LC medium comprising the at least one compound selected from the compounds of formulae Ia, Ib and Ic in a liquid-crystal device of the guest-host type, wherein the device in particular is a window component or a display. In the device the compound(s) and medium according to the invention are preferably provided in one or more switching layers.

The invention furthermore relates to a liquid-crystal display of the guest-host type containing an LC medium which comprises at least one compound of formula Ia, Ib and/or Ic.

The invention furthermore relates to the use of a mixture comprising a liquid-crystalline medium and at least one compound of a formula Ia, Ib and/or Ic in a device for regulating the passage of energy from an outside space into an inside space.

The device according to the invention, in addition to one or more compounds selected from the compounds of formulae Ia, Ib and Ic, and preferably a liquid-crystalline medium, preferably also comprises further dichroic dyes having a different structure to formulae Ia, Ib and Ic in the switching layer. It particularly preferably comprises one, two, three or four further dyes, very particularly preferably two or three further dyes and most preferably two further dyes having a different structure to formulae Ia, Ib and Ic.

With respect to the property of dichroism, the preferred properties described for the compounds of formulae Ia, Ib and Ic are also preferred for the optional further dichroic dyes.

The absorption spectra of the dichroic dyes of the switching layer preferably complement one another in such a way that the impression of a black colour arises for the eye. The preferably two or more dichroic dyes of the liquid-crystalline medium according to the invention preferably cover a large part of the visible spectrum. The precise way in which a mixture of dyes which appears black or grey to the eye can be prepared is known in the art and is described, for example, in M. Richter, Einführung in die Farbmetrik [Introduction to Colorimetry], 2nd Edition, 1981, ISBN 3-11-008209-8, Walter de Gruyter & Co.

The setting of the colour location of a mixture of dyes is described in the area of colorimetry. To this end, the spectra of the individual dyes are calculated taking into account the Lambert-Beer law to give an overall spectrum and converted into the corresponding colour locations and luminance values under the associated illumination, for example illuminant D65 for daylight, in accordance with the rules of colorimetry. The position of the white point is fixed by the respective illuminant, for example D65, and is quoted in tables, for example in the reference above. Different colour locations can be set by changing the proportions of the various dyes.

According to a preferred embodiment, the switching layer comprises one or more dichroic dyes which absorb light in the red and NIR region, i.e. at a wavelength of 600 nm to 2000 nm, preferably in the range from 600 nm to 1800 nm, particularly preferably in the range from 650 nm to 1300 nm.

In a preferred embodiment, the mesogenic medium further contains at least one dichroic dye in addition to the compound(s) selected from the group of compounds of formulae Ia, Ib and Ic. Preferably these further one or more dichroic dyes are selected from azo dyes, anthraquinones, methine compounds, azomethine compounds, merocyanine compounds, naphthoquinones, tetrazines, perylenes, terrylenes, quaterrylenes, higher rylenes, pyrromethenes, thiadiazoles, benzothiadiazoles, nickel dithiolenes, (metal) phthalocyanines, (metal) naphthalocyanines and (metal) porphyrins. Of these, particular preference is given to azo dyes, thiadiazoles and benzothiadiazoles.

In an embodiment the further dichroic dyes which are preferably provided in the switching layer having a different structure to the formulae Ia, Ib and Ic are preferably selected from the dye classes indicated in B. Bahadur, Liquid Crystals—Applications and Uses, Vol. 3, 1992, World Scientific Publishing, Section 11.2.1, and particularly preferably from the explicit compounds given in the table present therein.

Said dyes belong to the classes of dichroic dyes which are known in the art and have been described in the literature. Thus, for example, anthraquinone dyes are described in EP 34832, EP 44893, EP 48583, EP 54217, EP 56492, EP 59036, GB 2065158, GB 2065695, GB 2081736, GB 2082196, GB 2094822, GB 2094825, JP-A 55-123673, DE 3017877, DE 3040102, DE 3115147, DE 3115762, DE 3150803 and DE 3201120, naphthoquinone dyes are described in DE 3126108 and DE 3202761, azo dyes in EP 43904, DE 3123519, WO 82/2054, GB 2079770, JP-A 56-57850, JP-A 56-104984, U.S. Pat. Nos. 4,308,161, 4,308,162, 4,340,973, T. Uchida, C. Shishido, H. Seki and M. Wada: Mol. Cryst. Lig. Cryst. 39, 39-52 (1977), and H. Seki, C. Shishido, S. Yasui and T. Uchida: Jpn. J. Appl. Phys. 21, 191-192 (1982), and perylenes are described in EP 60895, EP 68427 and WO 82/1191. Rylene dyes as described, for example, in EP 2166040, US 2011/0042651, EP 68427, EP 47027, EP 60895, DE 3110960 and EP 698649.

Examples of preferred further dichroic dyes which may be present in the switching layer of the device are shown below

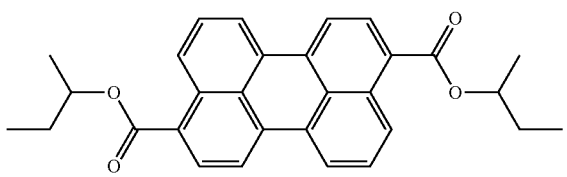

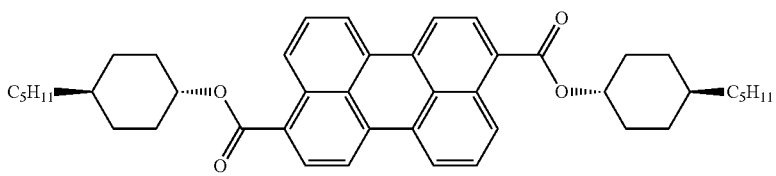

-continued
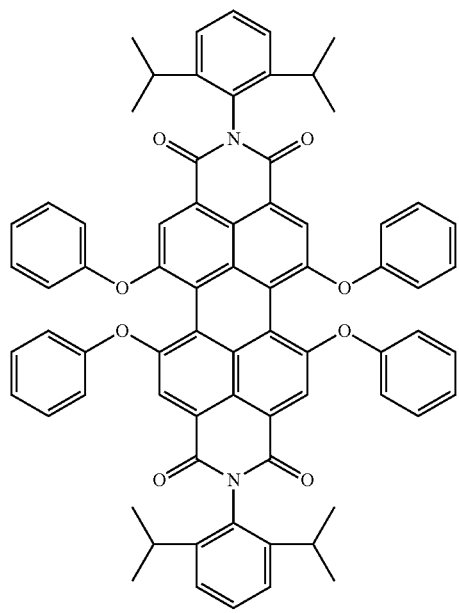
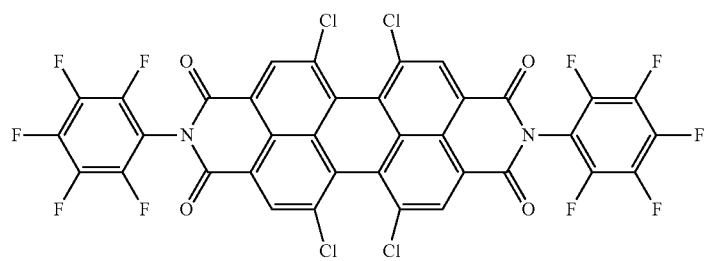
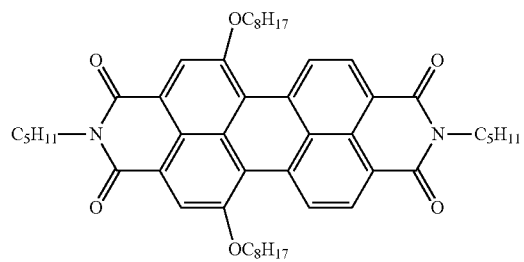
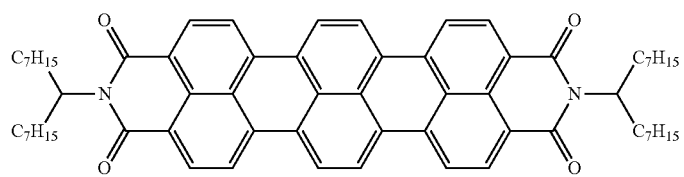

-continued
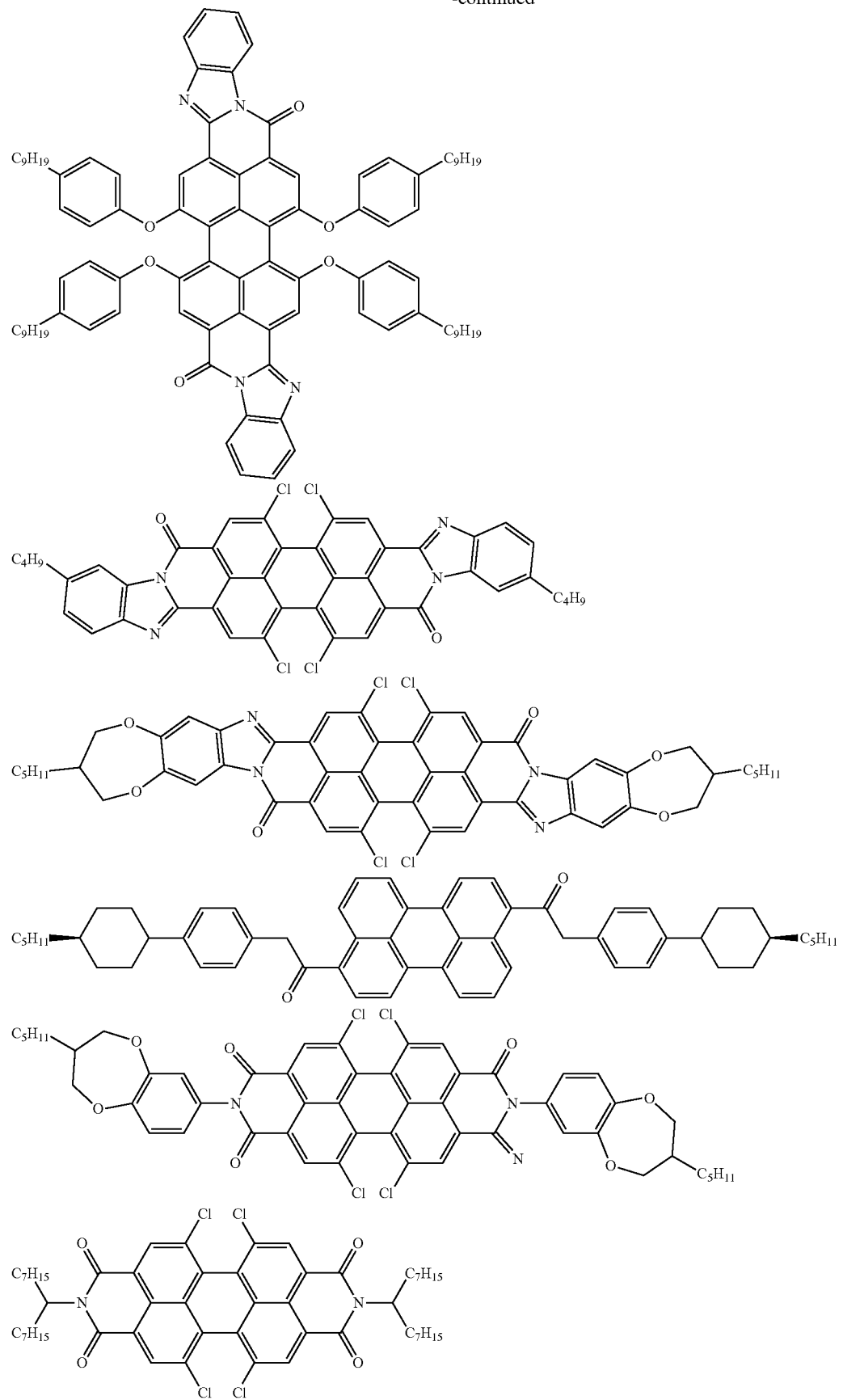

-continued
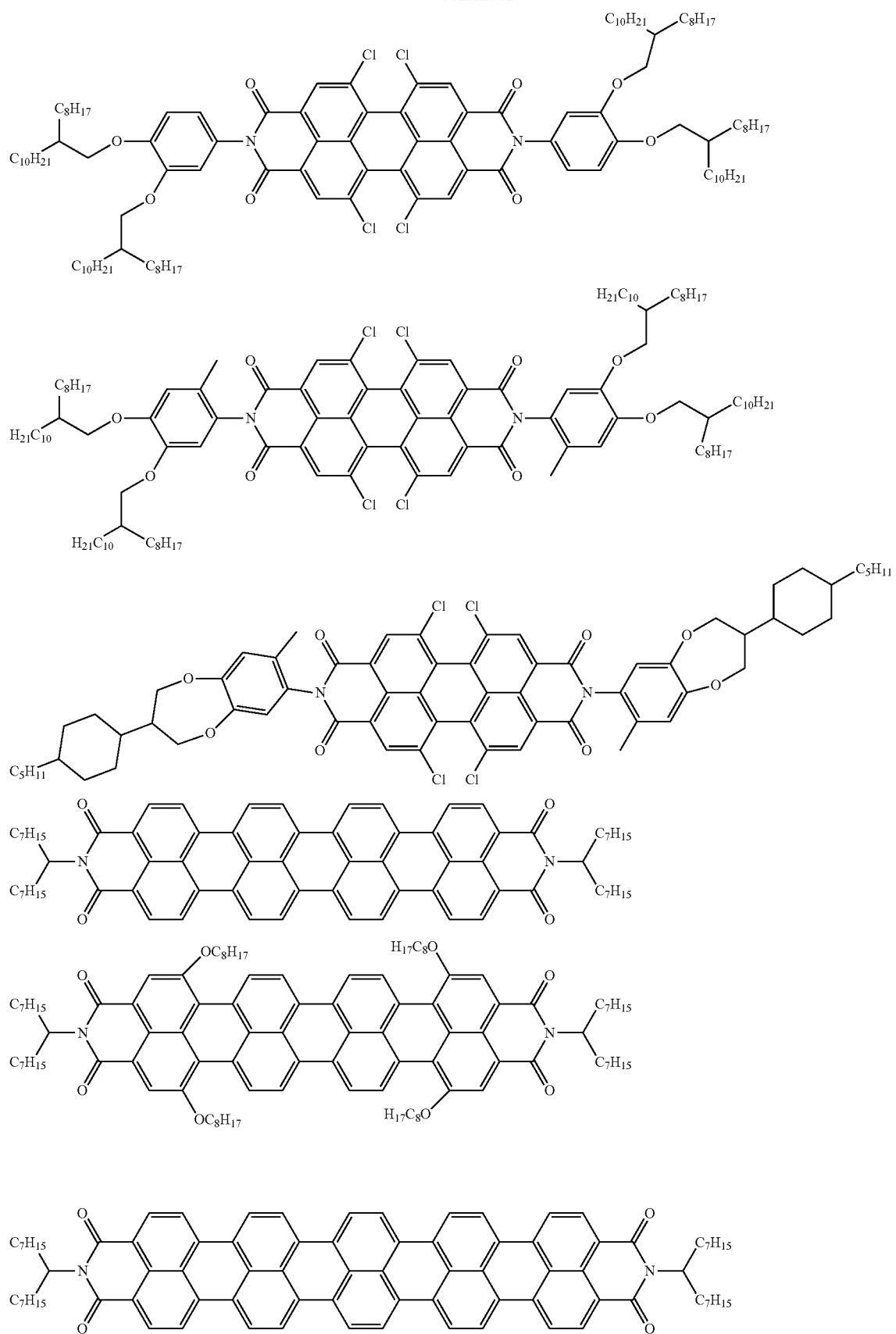

-continued
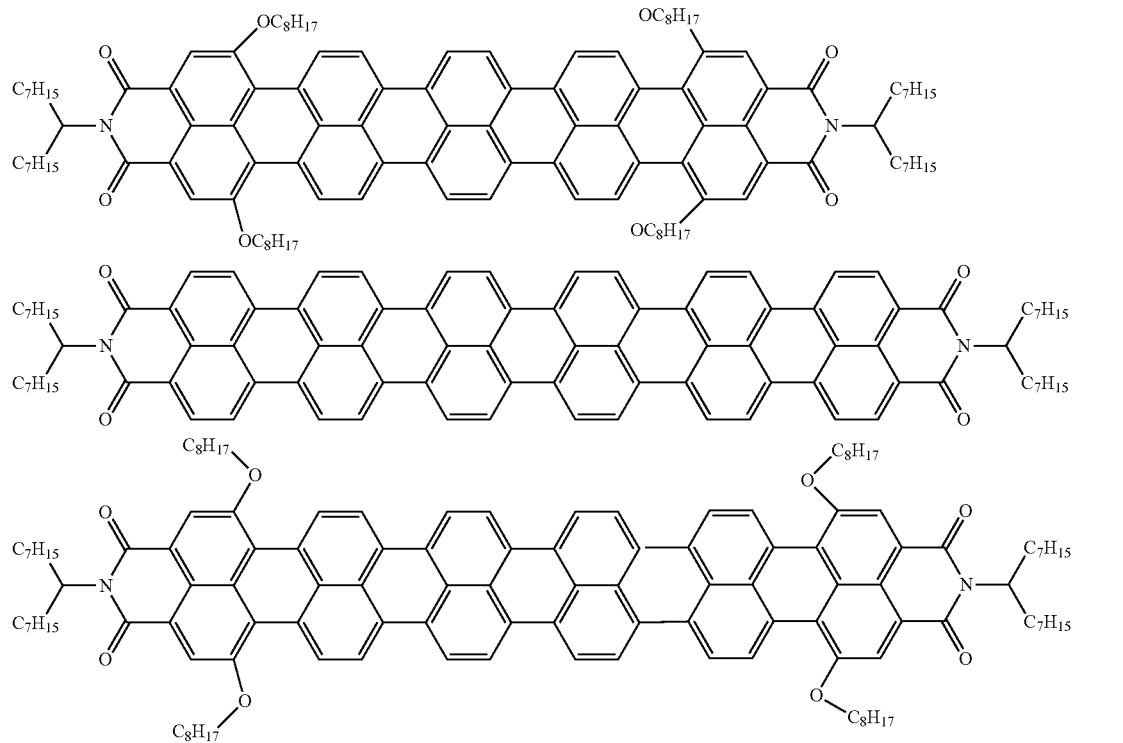
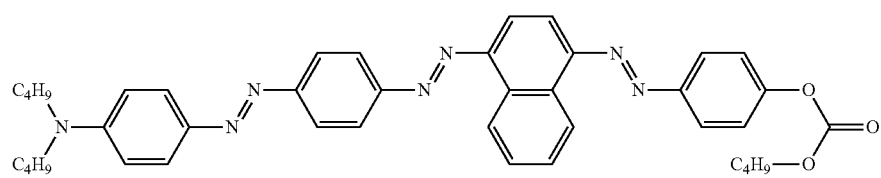
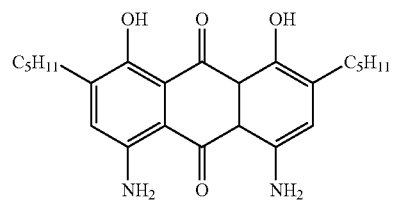
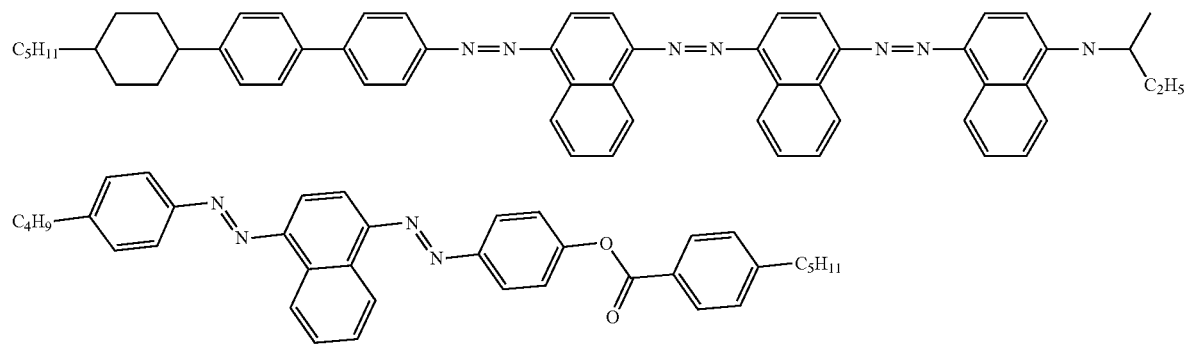

-continued

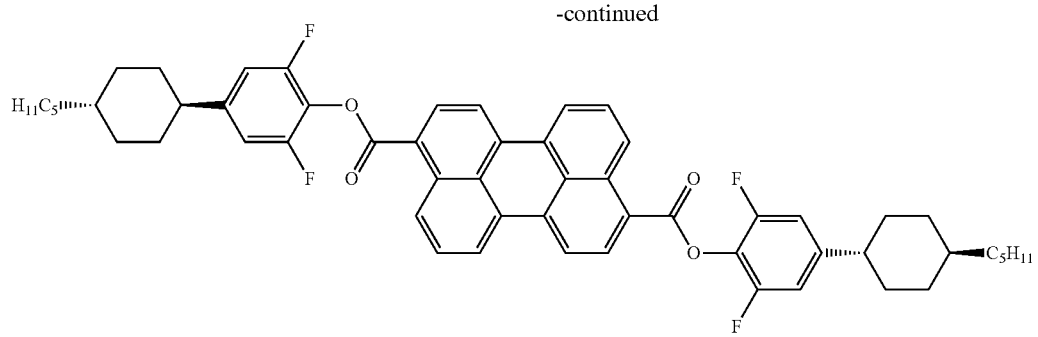

In a particularly preferred embodiment the mesogenic medium further comprises at least one compound of formula

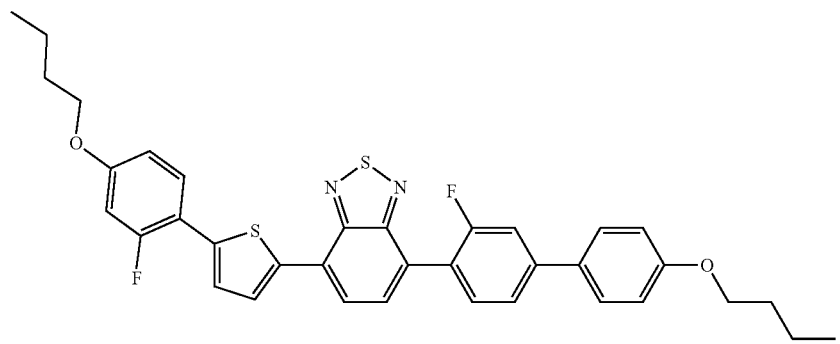

BT-1 or formula

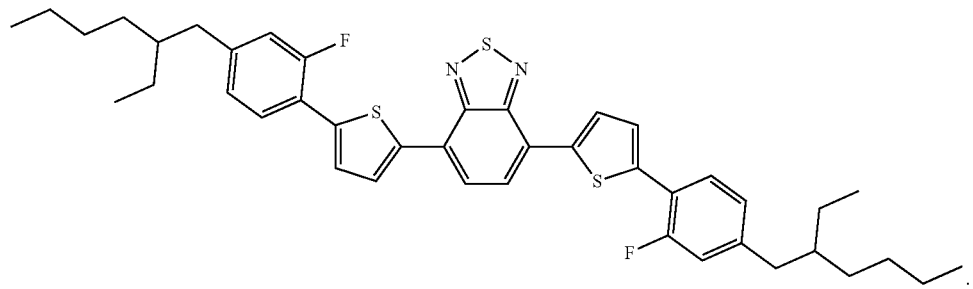

BT-2

In a preferred embodiment, the switching layer of the device according to the invention comprises one or more quencher compounds. This is particularly preferred if the device according to the invention comprises one or more fluorescent dyes in the switching layer.

Quencher compounds are compounds which quench fluorescence. The quencher compounds can take on the electronic excitation energy of adjacent molecules, such as, for example, fluorescent dyes, in the switching layer and undergo a transition into an electronically excited state in the process. The fluorescent dye to be quenched is thus converted into the electronic ground state and is thus prevented from emitting fluorescence or undergoing a subsequent reaction. The quencher compound itself returns to the ground state through radiation-free deactivation or by emission of light and is again available for further quenching.

The quencher compound may have various functions in the switching layer of the device according to the invention.

Firstly, the quencher compound may contribute to extending the lifetime of a dye system by deactivation of electronic excitation energy. Secondly, the quencher compound can eliminate additional colour effects which may be aesthetically undesirable, for example coloured emission in the inside space emanating from the fluorescent dyes in the switching layer.

In order to achieve effective quenching, the quencher compound should be adapted to the respective dye system, in particular the dye absorbing at the longest wavelength in a dye combination. The way to do this is known in the art.

Preferred quencher compounds are described, for example, in Table 8.1 on page 279 in J. R. Lakowicz, Principles of Fluorescence Spectroscopy, $3^{rd}$ Edition, 2010, ISBN 10: 0-387-31278-1, Springer Science+Business Media LLC. Further classes of compounds, e.g. so-called dark quenchers or black hole quenchers, are known in the art. Examples include azo dyes and aminoanthraquinones. The quencher compounds used in the switching layer of the device according to the invention may also be non-fluorescent dyes or dyes which only fluoresce in the NIR.

In a preferred embodiment of the switching layer according to the invention, any quencher compounds present are selected so that fluorescence in the visible part of the spectrum is suppressed.

The device according to the invention is preferably suitable for regulating the passage of energy in the form of sunlight from the environment into an inside space. The passage of energy to be regulated here takes place from the environment, i.e. an outside space, into an inside space.

The inside space here can be any desired space that is substantially sealed off from the environment, for example a building, a vehicle or a container.

The invention therefore furthermore relates to the use of the device for regulating the passage of energy from an outside space into an inside space.

However, the device can also be employed for aesthetic room design, for example for light and colour effects. For example, door and wall elements containing the device according to the invention in grey or in colour can be switched to transparent. Furthermore, the device may also comprise white or coloured flat backlighting which is modulated in brightness or yellow flat backlighting which is modulated in colour by means of a blue guest-host display. In case glass substrates are used in the device, one or both glass sides of the device according to the invention may be provided with roughened or structured glass for the coupling-out of light and/or for the generation of light effects.

In a further alternative use, the device is employed for regulating the incidence of light on the eyes, for example in protective goggles, visors or sunglasses, where the device keeps the incidence of light on the eyes low in one switching state and reduces the incidence of light to a lesser extent in another switching state.

The device according to the invention is preferably arranged in an opening in a relatively large two-dimensional structure, where the two-dimensional structure itself only allows slight passage of energy or none at all, and where the opening has relatively high energy transmissivity. The two-dimensional structure is preferably a wall or another boundary of an inside space to the outside. Furthermore, the two-dimensional structure preferably covers an area of at least equal size, particularly preferably an area at least twice as large as the opening in it in which the device according to the invention is disposed.

The device is preferably characterised in that it has an area of at least 0.05 $m^2$, preferably at least 0.1 $m^2$, particularly preferably at least 0.5 $m^2$ and very particularly preferably at least 1.0 $m^2$.

The device is preferably accommodated in an opening having relatively high energy transmissivity, as described above, in a building, a container, a vehicle or another substantially closed space. The device can generally be used for any desired inside spaces, particularly if they have only limited exchange of air with the environment and have light-transmitting boundary surfaces through which input of energy from the outside in the form of light energy can take place. The use of the device for inside spaces which are subjected to strong insolation through light-transmitting areas, for example through window areas, is particularly preferred.

The device according to the invention is switchable. Switching here is taken to mean a change in the passage of energy through the device. The device according to the invention is preferably electrically switchable, as described, for example, in WO 2009/141295 and in WO 2014/090373. However, the device may also be thermally switchable, as described, for example, in WO 2010/118422. In this case, the switching preferably takes place by a transition from a nematic state to an isotropic state through a change in the temperature of the switching layer comprising the compound(s) of formula Ia, Ib and/or Ic and a liquid-crystalline medium. In the nematic state, the molecules of the liquid-crystalline medium are in ordered form, and thus also the compound(s) of formula Ia, Ib and/or Ic, for example aligned parallel to the surface of the device through the action of an alignment layer. In the isotropic state, the molecules are in disordered form, and thus also the compound(s) of formula Ia, Ib and/or Ic. The difference between ordered and disordered presence of the dichroic compound (s) causes a difference in the light transmissivity of the switching layer of the device according to the invention, in accordance with the principle that dichroic compounds have a higher or lower absorption coefficient depending on the alignment in relation to the polarization plane of the light.

In the case where the device is electrically switchable, it preferably comprises two or more electrodes, which are preferably installed on both sides of the switching layer. The electrodes preferably consist of ITO or a thin, preferably transparent metal and/or metal-oxide layer, for example silver or FTO (fluorine-doped tin oxide) or an alternative material known in the art for this use. The electrodes are preferably provided with electrical connections. The voltage is preferably provided by a battery, a rechargeable battery or an external power supply, in particular an external power supply.

The switching operation in the case of electrical switching takes place by a (re)alignment of the molecules of the liquid-crystalline medium by the application of voltage.

In a preferred embodiment, the device is converted from a state having high absorption, i.e. low light transmissivity, which is present without voltage, into a state having lower absorption, i.e. higher light transmissivity. The liquid-crystalline medium of the switching layer is preferably nematic in both states. The voltage-free state is preferably characterised in that the molecules of the liquid-crystalline medium, and thus the molecules of the compound(s) of formula Ia, Ib and/or Ic, are aligned parallel to the plane of the switching layer. This is preferably achieved by a correspondingly selected alignment layer. The state where voltage is applied is preferably characterised in that the molecules of the liquid-crystalline medium, and thus molecules of the compound(s) of formula Ia, Ib and/or Ic, are perpendicular to the plane of the switching layer.

In an alternative embodiment, the device is switchable from a state having low absorption, i.e. high light transmissivity, which is present without voltage, into a state having higher absorption, i.e. lower light transmissivity. The liquid-crystalline medium of the switching layer is preferably nematic in both states. The voltage-free state is preferably characterised in that the molecules of the liquid-crystalline medium of the switching layer, and thus the molecules of the compound(s) of formula Ia, Ib and/or Ic, are aligned perpendicular to the plane of the switching layer. This is preferably achieved by a correspondingly selected alignment layer. The state where voltage is applied is preferably characterised in that the molecules of the liquid-crystalline medium of the switching layer, and thus the molecules of the compound(s) of formula Ia, Ib and/or Ic, are parallel to the plane of the switching layer.

According to a preferred embodiment of the invention, the device can be operated without an external power supply by providing the energy required by means of a solar cell or another device for conversion of light and/or heat energy into electrical energy which is connected to the device. The provision of the energy by means of the solar cell can take place directly or indirectly, i.e. via a battery or rechargeable battery or other unit for the storage of energy connected in-between. The solar cell is preferably mounted on the outside of the device or is an internal component of the device, as disclosed, for example, in WO 2009/141295. Particular preference is given here to solar cells which are particularly efficient in the case of diffuse light, and transparent solar cells.

The device according to the invention preferably has the following layer sequence, where further layers may additionally be present. The layers indicated below are preferably directly adjacent to one another in the device:

substrate layer, preferably comprising glass or polymer
electrically conductive transparent layer, preferably comprising ITO
alignment layer
switching layer comprising one or more compounds selected from the group of compounds of formulae Ia, Ib and Ic
alignment layer
electrically conductive transparent layer, preferably comprising ITO
substrate layer, preferably comprising glass or polymer.

The device according to the invention preferably comprises one or more, particularly preferably two, alignment layers. The alignment layers are preferably directly adjacent to the two sides of the switching layer comprising the compound(s) of formula Ia, Ib and/or Ic.

The alignment layers used in the device according to the invention can be any desired layers known to the person skilled in the art for this purpose. Preference is given to polyimide layers, particularly preferably layers comprising rubbed polyimide. In an embodiment planar alignment is provided, where more preferably a slight pretilt angle may be set. In an alternative embodiment homeotropic alignment is provided, where more preferably high pretilt angles are set.

Furthermore, polymers obtained by an exposure process to polarised light can be used as alignment layer in order to achieve alignment of the compounds of the liquid-crystalline medium in accordance with an alignment axis, i.e. photoalignment.

The switching layer in the device according to the invention is furthermore preferably arranged between two substrate layers or enclosed thereby.

The substrate layers can consist, for example, of glass or a polymer, preferably a light-transmitting polymer.

The device is preferably characterised in that it does not comprise a polymer-based polariser, particularly preferably does not comprise a polariser in the solid material phase and very particularly preferably does not comprise a polariser at all.

However, in accordance with an alternative embodiment, the device may also comprise one or more polarisers. The polarisers in this case are preferably linear polarisers.

If precisely one polariser is present, its absorption direction is preferably perpendicular to the orientation axis of the compounds of the liquid-crystalline medium of the device according to the invention on the side of the switching layer on which the polariser is located.

In the device according to the invention, both absorptive and also reflective polarisers can optionally be employed. Preference is given to the use of polarisers which are in the form of thin optical films. Examples of reflective polarisers which can be used in the device according to the invention are DRPF (diffusive reflective polariser film, 3M), DBEF (dual brightness enhanced film, 3M), DBR (layered-polymer distributed Bragg reflectors, as described in U.S. Pat. Nos. 7,038,745 and 6,099,758) and APF films (advanced polariser film, 3M, cf. Technical Digest SID 2006, 45.1, US 2011/0043732 and U.S. Pat. No. 7,023,602). It is furthermore possible to employ polarisers based on wire grids (WGPs, wire-grid polarisers) which reflect infrared light. Examples of absorptive polarisers which optionally can be employed in the device according to the invention are the Itos XP38 polariser film and the Nitto Denko GU-1220DUN polariser film. An example of a circular polariser which can be used in accordance with the invention is the APNCP37-035-STD polariser (American Polarizers). A further example is the CP42 polariser (ITOS).

In a preferred embodiment, the device according to the invention is a constituent of a window, more preferably a window component comprising at least one glass surface, particularly preferably a component of an insulated glazing unit.

Window here is taken to mean in particular a structure in a building which comprises a frame and at least one glass pane surrounded by this frame. It preferably comprises a heat-insulating frame and two or more glass panes, i.e. multipane insulating glass.

According to a preferred embodiment, the device according to the invention is applied directly to a glass surface of a window, particularly preferably in the interspace between two glass panes of multipane insulating glass.

The invention furthermore relates to a window comprising a device according to the invention, preferably having the preferred features indicated above.

Owing to the electronic properties of the compounds according to the invention, these compounds are also suitable, besides the use as dye, as organic semiconductors.

The invention therefore furthermore relates to the use of compounds of the formula Ia, Ib and/or Ic in organic electronic components, such as, for example, organic light-emitting diodes (OLEDs), organic field-effect transistors (OFETs), printed circuits, radio frequency identification elements (RFIDs), lighting elements, photovoltaic devices and optical sensors.

Owing to their coloured nature and good solubility in organic materials, the compounds according to the invention are eminently suitable as dyes. The invention therefore likewise relates to the use of dyes of the formula Ia, Ib and/or Ic for colouring a polymer.

In the present invention and especially in the following examples, the structures of the mesogenic compounds are indicated by means of abbreviations, also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, each having n, m and l C atoms respectively. Table A lists the codes used for the ring elements of the core structures of the compounds, while Table B shows the linking groups. Table C gives the meanings of the codes for the left-hand or right-hand end groups. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

| Code | Structure | Code | Structure |
|---|---|---|---|
| C | cyclohexane-1,4-diyl | C(CN) | 1-cyano-cyclohexane-1,4-diyl |
| P | 1,4-phenylene | P(F, CN) | 2-fluoro-3-cyano-1,4-phenylene |
| D | 1,3-dioxane-2,5-diyl | DI | 1,3-dioxane-5,2-diyl |
| A | tetrahydropyran-2,5-diyl | AI | tetrahydropyran-5,2-diyl |
| G | 2-fluoro-1,4-phenylene | GI | 3-fluoro-1,4-phenylene |
| U | 2,3-difluoro-1,4-phenylene | UI | 3,2-difluoro-1,4-phenylene |
| Y | 2,3-difluoro-1,4-phenylene | | |
| M | pyrimidine-2,5-diyl | MI | pyrimidine-5,2-diyl |
| N | pyridine-2,5-diyl | NI | pyridine-5,2-diyl |
| Np | naphthalene-2,6-diyl | dH | decahydronaphthalene-2,6-diyl |
| N3f | trifluoronaphthalene | N3fI | trifluoronaphthalene |
| tH | tetrahydronaphthalene-2,6-diyl | tHI | tetrahydronaphthalene-6,2-diyl |

TABLE A-continued

Ring elements

| | | | |
|---|---|---|---|
| tH2f | 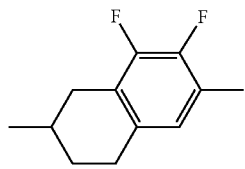 | tH2fI | 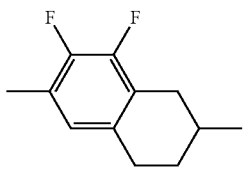 |
| K | 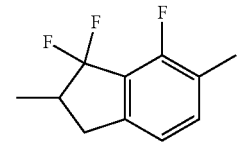 | KI | 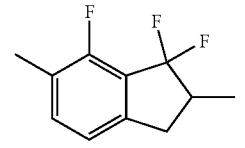 |
| L | 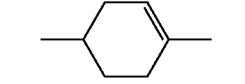 | LI |  |
| F | 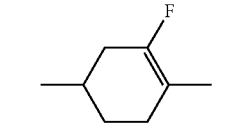 | FI | 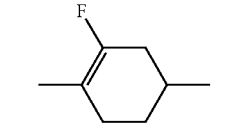 |
| Nf | 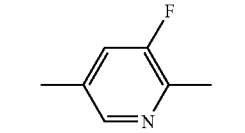 | NfI | 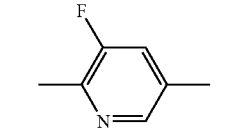 |
| B | 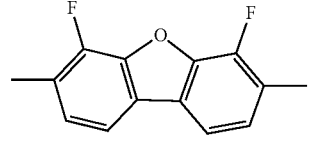 | | |

TABLE B

Linking groups

| | | | | | | | |
|---|---|---|---|---|---|---|---|
| E | —CH$_2$CH$_2$— | Z | —CO—O— | B | —CF=CF— | Q | —CF$_2$—O— |
| V | —CH=CH— | ZI | —O—CO— | T | —C≡C— | QI | —O—CF$_2$— |
| X | —CF=CH— | O | —CH$_2$—O— | W | —CF$_2$CF$_2$— | | |
| XI | —CH=CF— | OI | —O—CH$_2$— | | | | |

TABLE C

End groups

| Left-hand side | | Right-hand side | |
|---|---|---|---|
| Use alone | | | |
| -n- | C$_n$H$_{2n+1}$— | -n | —C$_n$H$_{2n+1}$ |
| -nO- | C$_n$H$_{2n+1}$—O— | -On | —O—C$_n$H$_{2n+1}$ |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n+1}$— | -Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| -N- | N≡C— | -N | —C≡N |
| -S- | S=C=N— | -S | —N=C=S |
| -F- | F— | -F | —F |
| -Cl- | Cl— | -Cl | —Cl |
| -M- | CFH$_2$— | -M | —CFH$_2$ |
| -D- | CF$_2$H— | -D | —CF$_2$H |
| -T- | CF$_3$— | -T | —CF$_3$ |

TABLE C-continued

| | End groups | | |
|---|---|---|---|
| Left-hand side | | Right-hand side | |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -OXF- | CF$_2$=CH—O— | -OXF | —O—CH=CF$_2$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |
| Use together with one another and with others | | | |
| -...A...- | —C≡C— | -...A... | —C≡C— |
| -...V...- | CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m each denote integers, and the three dots " . . . " are place-holders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

C$_n$H$_{2n+1}$—[cyclohexyl]—[cyclohexyl]—C$_m$H$_{2m+1}$     CC-n-m

C$_n$H$_{2n+1}$—[cyclohexyl]—[cyclohexyl]—O—C$_m$H$_{2m+1}$     CC-n-Om

C$_n$H$_{2n+1}$—[cyclohexyl]—[cyclohexyl]—CH=CH$_2$     CC-n-V

C$_n$H$_{2n+1}$—[cyclohexyl]—[cyclohexyl]—CH=CH—C$_m$H$_{2m+1}$     CC-n-Vm

C$_n$H$_{2n+1}$—[cyclohexyl]—[cyclohexyl]—(CH$_2$)$_m$—CH=CH$_2$     CC-n-mV

C$_n$H$_{2n+1}$—[cyclohexyl]—[cyclohexyl]—(CH$_2$)$_m$—CH=CH—C$_l$H$_{2l+1}$     CC-n-mVl H$_2$C=CH—[cyclohexyl]—[cyclohexyl]—CH=CH$_2$     CC-V-V CH$_2$=CH—[cyclohexyl]—[cyclohexyl]—(CH$_2$)$_m$—CH=CH$_2$     CC-V-mV CH$_2$=CH—[cyclohexyl]—[cyclohexyl]—CH=CH—C$_m$H$_{2m+1}$     CC-V-Vm TABLE D-continued
| Illustrative structures | |
|---|---|
| 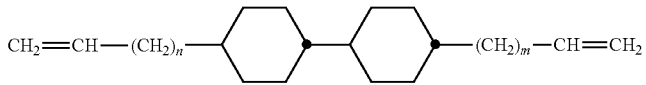 | CC-Vn-mV |
| 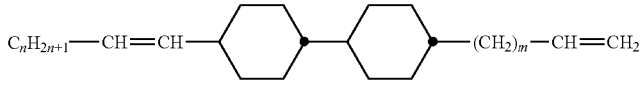 | CC-nV-mV |
| 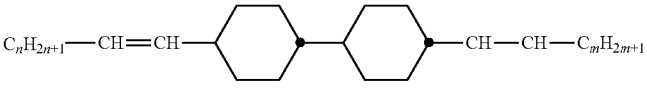 | CC-nV-Vm |
| 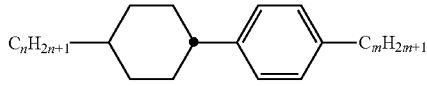 | CP-n-m |
|  | CP-nO-m |
| 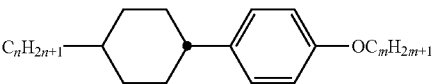 | CP-n-Om |
| 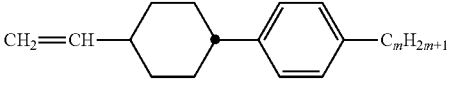 | CP-V-m |
|  | CP-Vn-m |
| 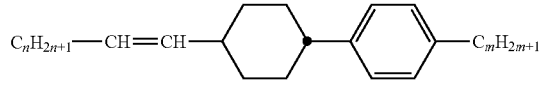 | CP-nV-m |
| 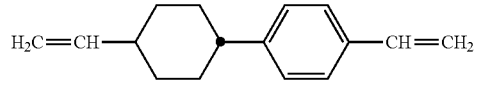 | CP-V-V |
| 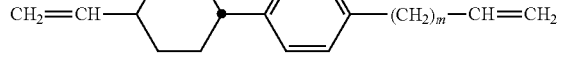 | CP-V-mV |
| 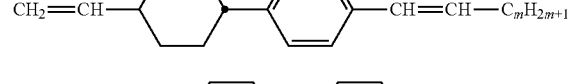 | CP-V-Vm |
| 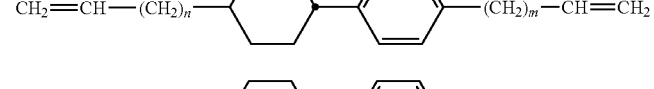 | CP-Vn-mV |
|  | CP-nV-mV |
| 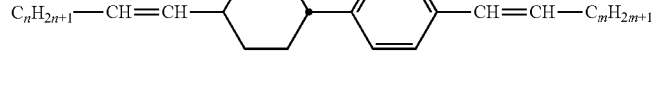 | CP-nV-Vm |

TABLE D-continued

Illustrative structures

| Structure | Code |
|---|---|
| $C_nH_{2n+1}$—⌬—⌬—$C_mH_{2m+1}$ | PP-n-m |
| $C_nH_{2n+1}$—⌬—⌬—$OC_mH_{2m+1}$ | PP-n-Om |
| $C_nH_{2n+1}$—⌬—⌬—$CH=CH_2$ | PP-n-V |
| $C_nH_{2n+1}$—⌬—⌬—$CH=CH-C_mH_{2m+1}$ | PP-n-Vm |
| $C_nH_{2n+1}$—⌬—⌬—$(C_mH_{2m})-CH=CH_2$ | PP-n-mV |
| $C_nH_{2n+1}$—⌬—⌬—$(CH_2)_m-CH=CH-C_lH_{2l+1}$ | PP-n-mVl |
| $C_nH_{2n+1}$—⌬—⌬—⌬—$C_mH_{2m+1}$ | CCP-n-m |
| $C_nH_{2n+1}O$—⌬—⌬—⌬—$C_mH_{2m+1}$ | CCP-nO-m |
| $C_nH_{2n+1}$—⌬—⌬—⌬—$OC_mH_{2m+1}$ | CCP-n-Om |
| $C_nH_{2n+1}$—⌬—⌬—⌬—$CH=CH_2$ | CCP-n-V |
| $C_nH_{2n+1}$—⌬—⌬—⌬—$CH=CH-C_mH_{2m+1}$ | CCP-n-Vm |
| $C_nH_{2n+1}$—⌬—⌬—⌬—$(C_mH_{2m})-CH=CH_2$ | CCP-n-mV |
| $C_nH_{2n+1}$—⌬—⌬—⌬—$(C_mH_{2m})-CH=CH-C_lH_{2l+1}$ | CCP-n-mVl |
| $H_2C=CH$—⌬—⌬—⌬—$C_mH_{2m+1}$ | CCP-V-m |
| $C_nH_{2n+1}-CH=CH$—⌬—⌬—⌬—$C_mH_{2m+1}$ | CCP-nV-m |
| $CH_2=CH-(CH_2)_n$—⌬—⌬—⌬—$C_mH_{2m+1}$ | CCP-Vn-m |

TABLE D-continued

| Illustrative structures | |
|---|---|
| $C_nH_{2n+1}$—CH=CH—$(CH_2)_m$—[Cy]—[Cy]—[Ph]—$C_lH_{2l+1}$ | CCP-nVm-I |
| $C_nH_{2n+1}$—[Cy]—[Ph]—[Ph]—$C_mH_{2m+1}$ | CPP-n-m |
| $C_nH_{2n+1}$—[Cy]—[Ph]—[Ph(F)]—$C_mH_{2m+1}$ | CPG-n-m |
| $C_nH_{2n+1}$—[Cy]—[Ph(F)]—[Ph]—$C_mH_{2m+1}$ | CGP-n-m |
| $C_nH_{2n+1}$O—[Cy]—[Ph]—[Ph]—$C_mH_{2m+1}$ | CPP-nO-m |
| $C_nH_{2n+1}$—[Cy]—[Ph]—[Ph]—O$C_mH_{2m+1}$ | CPP-n-Om |
| $H_2C$=CH—[Cy]—[Ph]—[Ph]—$C_mH_{2m+1}$ | CPP-V-m |
| $C_nH_{2n+1}$—CH=CH—[Cy]—[Ph]—[Ph]—$C_mH_{2m+1}$ | CPP-nV-m |
| $CH_2$=CH—$(C_nH_{2n})$—[Cy]—[Ph]—[Ph]—$C_mH_{2m+1}$ | CPP-Vn-m |
| $C_nH_{2n+1}$—CH=CH—$(C_mH_{2m})$—[Cy]—[Ph]—[Ph]—$C_lH_{2l+1}$ | CPP-nVm-I |
| $C_nH_{2n+1}$—[Ph]—[Ph(F)]—[Ph]—$C_mH_{2m+1}$ | PGP-n-m |
| $C_nH_{2n+1}$—[Ph]—[Ph(F)]—[Ph]—CH=$CH_2$ | PGP-n-V |
| $C_nH_{2n+1}$—[Ph]—[Ph(F)]—[Ph]—CH=CH—$C_mH_{2m+1}$ | PGP-n-Vm |

TABLE D-continued

| Illustrative structures | |
|---|---|
| $C_nH_{2n+1}$—[Ph]—[Ph(F)]—[Ph]—$(CH_2)_m$—CH=CH$_2$ | PGP-n-mV |
| $C_nH_{2n+1}$—[Ph]—[Ph(F)]—[Ph]—$(CH_2)_m$—CH=CH—$C_lH_{2l+1}$ | PGP-n-mVI |
| $C_nH_{2n+1}$—[Cy]—[Cy]—$CH_2$—$CH_2$—[Cy]—$C_mH_{2m+1}$ | CCEC-n-m |
| $C_nH_{2n+1}$—[Cy]—[Cy]—$CH_2$—$CH_2$—[Cy]—O—$C_mH_{2m+1}$ | CCEC-n-Om |
| $C_nH_{2n+1}$—[Cy]—[Cy]—C(O)—O—[Cy]—O—$C_mH_{2m+1}$ | CCZC-n-Om |
| $C_nH_{2n+1}$—[Cy]—[Cy]—$CH_2$—$CH_2$—[Ph]—$C_mH_{2m+1}$ | CCEP-n-m |
| $C_nH_{2n+1}$—[Cy]—[Cy]—$CH_2$—$CH_2$—[Ph(F)]—$C_mH_{2m+1}$ | CCEGI-n-m |
| $C_nH_{2n+1}$—[Cy]—[Cy]—$CH_2$—$CH_2$—[Ph]—F | CCEP-n-F |
| $C_nH_{2n+1}$—[Cy]—[Cy]—$CH_2$—$CH_2$—[Ph]—O—$C_mH_{2m+1}$ | CCEP-n-Om |
| $C_nH_{2n+1}$—[Cy]—[Ph]—[Ph]—[Cy]—$C_mH_{2m+1}$ | CPPC-n-m |
| $C_nH_{2n+1}$—[Cy]—[Ph(F)]—[Ph]—[Cy]—$C_mH_{2m+1}$ | CGPC-n-m |
| $C_nH_{2n+1}$—[Cy]—[Ph]—[Ph]—[Cy]—$C_mH_{2m+1}$ | CCPC-n-m |
| $C_nH_{2n+1}$—[Cy]—[Cy]—CO—O—[Ph]—[Cy]—$C_mH_{2m+1}$ | CCZPC-n-m |
| $C_nH_{2n+1}$—[Cy]—[Cy]—CO—O—[Ph]—$C_mH_{2m+1}$ | CCZP-n-m |

TABLE D-continued

| Illustrative structures | |
|---|---|
| (structure) | CCZGI-n-m |
| (structure) | CPGP-n-m |
| (structure) | CPGP-n-mV |
| (structure) | CPGP-n-mVI |
| (structure) | PGIGP-n-m |
| (structure) | CP-n-F |
| (structure) | CP-n-N |
| (structure) | CP-n-Cl |
| (structure) | GP-n-F |
| (structure) | GP-n-Cl |
| (structure) | PZG-n-N |
| (structure) | CCP-n-OT |

TABLE D-continued

| Illustrative structures | |
|---|---|
| $C_nH_{2n+1}$—[Cy]—[Cy]—[Ph(3-F, 4-OCF$_3$)] | CCG-n-OT |
| $C_nH_{2n+1}$—[Cy]—[Cy]—[Ph(4-CF$_3$)] | CCP-n-T |
| $C_nH_{2n+1}$—[Cy]—[Cy]—[Ph(3,4-F$_2$)] | CCG-n-F |
| $H_2C=CH$—[Cy]—[Cy]—[Ph(3,4-F$_2$)] | CCG-V-F |
| $H_2C=CH$—[Cy]—[Cy]—[Ph(3,4-F$_2$)] | CCG-V-F |
| $C_nH_{2n+1}$—[Cy]—[Cy]—[Ph(3,4,5-F$_3$)] | CCU-n-F |
| $C_nH_{2n+1}$—[Cy]—[1,3-dioxane]—[Ph(3,4,5-F$_3$)] | CDU-n-F |
| $C_nH_{2n+1}$—[Cy]—[Ph]—[Ph(3,4-F$_2$)] | CPG-n-F |
| $C_nH_{2n+1}$—[Cy]—[Ph]—[Ph(3,4,5-F$_3$)] | CPU-n-F |
| $C_nH_{2n+1}$—[Cy]—[Ph(2-F)]—[Ph(3,4,5-F$_3$)] | CGU-n-F |

TABLE D-continued

| Illustrative structures | |
|---|---|
| (structure) | PGU-n-F |
| (structure) | GGP-n-F |
| (structure) | GGP-n-Cl |
| (structure) | GIGIP-n-F |
| (structure) | GIGIP-n-Cl |
| (structure) | CCPU-n-F |
| (structure) | CCGU-n-F |
| (structure) | CPGU-n-F |
| (structure) | CPGU-n-OT |

TABLE D-continued
| Illustrative structures | |
|---|---|
| 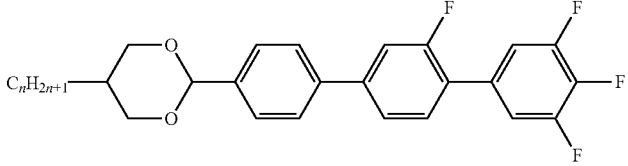 | DPGU-n-F |
| 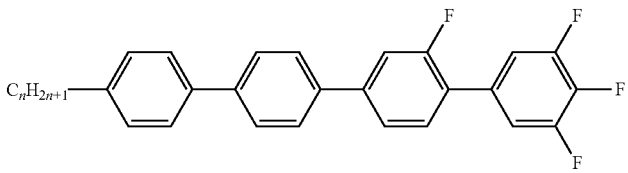 | PPGU-n-F |
| 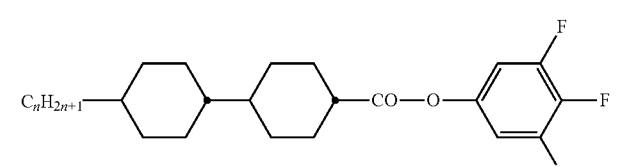 | CCZU-n-F |
| 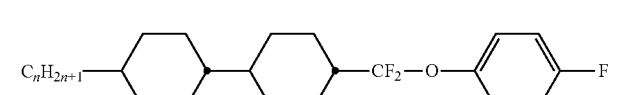 | CCQP-n-F |
| 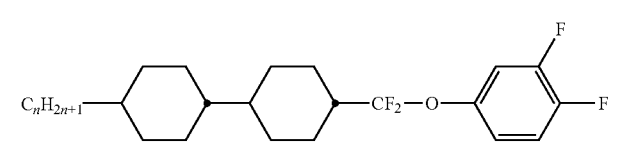 | CCQG-n-F |
| 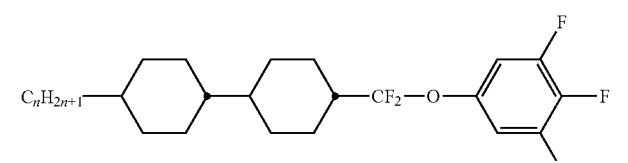 | CCQU-n-F |
| 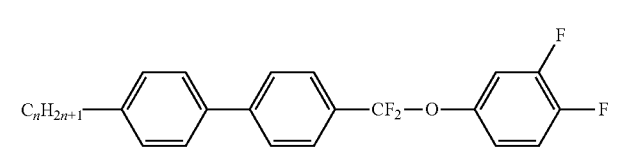 | PPQG-n-F |
| 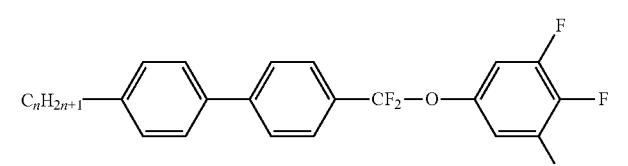 | PPQU-n-F |
| 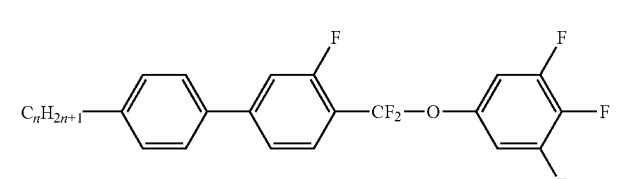 | PGQU-n-F |

TABLE D-continued

| Illustrative structures | |
|---|---|
| (structure) | GGQU-n-F |
| (structure) | PUQU-n-F |
| (structure) | MUQU-n-F |
| (structure) | NUQU-n-F |
| (structure) | CDUQU-n-F |
| (structure) | CPUQU-n-F |
| (structure) | CGUQU-n-F |
| (structure) | PGPQP-n-F |
| (structure) | PGPQG-n-F |

TABLE D-continued

| Illustrative structures | |
|---|---|
| $C_nH_{2n+1}$—⟨phenyl⟩—⟨phenyl(F)⟩—⟨phenyl⟩—$CF_2$—O—⟨phenyl(F,F,F)⟩ | PGPQU-n-F |
| $C_nH_{2n+1}$—⟨phenyl⟩—⟨phenyl(F)⟩—⟨phenyl(F,F)⟩—$CF_2$—O—⟨phenyl(F,F,F)⟩ | PGUQU-n-F |
| $C_nH_{2n+1}$—⟨tetrahydropyran⟩—⟨phenyl⟩—⟨phenyl(F,F)⟩—$CF_2$—O—⟨phenyl(F,F,F)⟩ | APUQU-n-F |
| $C_nH_{2n+1}$—⟨dioxane⟩—⟨phenyl(F)⟩—⟨phenyl(F,F)⟩—$CF_2$—O—⟨phenyl(F,F,F)⟩ | DGUQU-n-F |
| $C_nH_{2n+1}$—⟨cyclohexyl⟩—⟨cyclohexyl(F,F)⟩—$OC_mH_{2m+1}$ | CY-n-Om |
| $C_nH_{2n+1}$—⟨cyclohexyl⟩—⟨cyclohexyl(F,F)⟩—$C_mH_{2m+1}$ | CY-n-m |
| $CH_2=CH$—⟨cyclohexyl⟩—⟨cyclohexyl(F,F)⟩—$OC_mH_{2m+1}$ | CY-V-Om |
| $C_nH_{2n+1}$—CH=CH—⟨cyclohexyl⟩—⟨cyclohexyl(F,F)⟩—(O)—$C_mH_{2m+1}$ | CY-nV-(O)m |
| $C_nH_{2n+1}$—⟨cyclohexyl⟩—CH=CH—⟨cyclohexyl⟩—$C_mH_{2m+1}$ | CVC-n-m |
| $CH_2=CH$—⟨cyclohexyl⟩—CH=CH—⟨cyclohexyl(F,F)⟩—$C_mH_{2m+1}$ | CVY-V-m |

TABLE D-continued
Illustrative structures
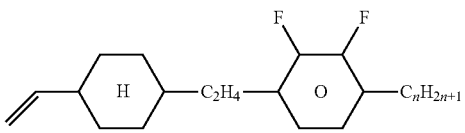
CEY-V-m
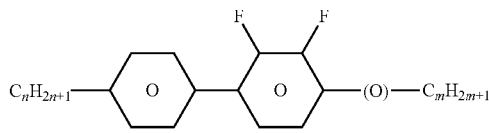
PY-n-(O)m
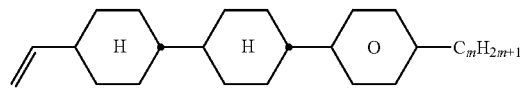
CCP-V-m
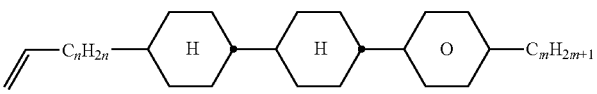
CCP-Vn-m
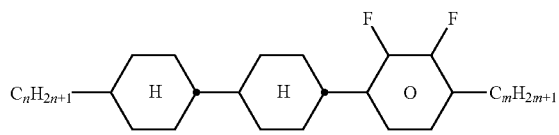
CCY-n-m
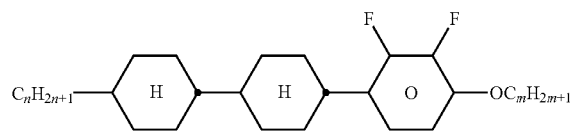
CCY-n-Om
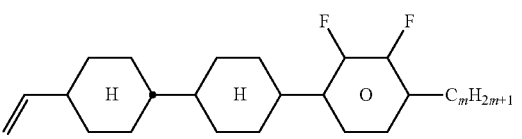
CCY-V-m
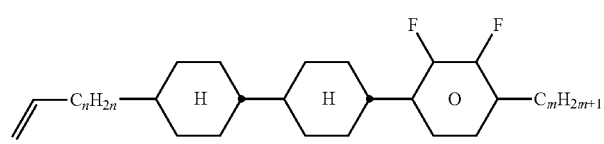
CCY-Vn-m
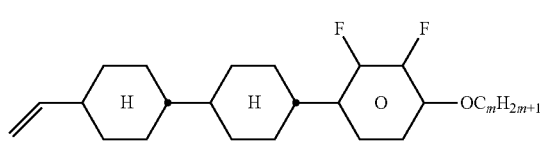
CCY-V-Om
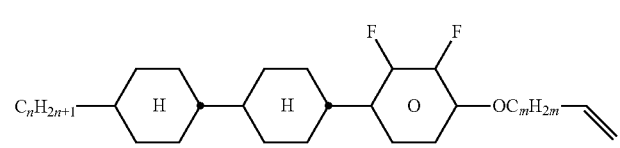
CCY-n-OmV
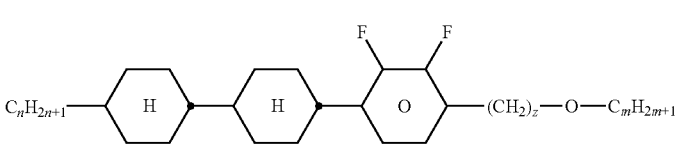
CCY-n-zOm
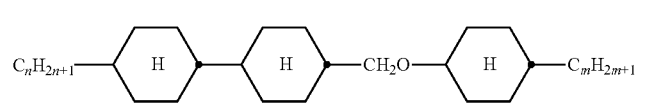
CCOC-n-m TABLE D-continued

| Illustrative structures | |
|---|---|
| $C_nH_{2n+1}$—[H]—[O]—[O(F,F)]—(O)—$C_mH_{2m+1}$ | CPY-n-(O)m |
| CH$_2$=CH—[H]—[O]—[O(F,F)]—OC$_m$H$_{2m+1}$ | CPY-V-Om |
| $C_nH_{2n+1}$—[H]—CF$_2$O—[O(F,F)]—(O)—$C_mH_{2m+1}$ | CQY-n-(O)m |
| $C_nH_{2n+1}$—[H]—OCF$_2$—[O(F,F)]—(O)—$C_mH_{2m+1}$ | CQIY-n-(O)m |
| $C_nH_{2n+1}$—[H]—[H]—CF$_2$O—[O(F,F)]—(O)—$C_mH_{2m+1}$ | CCQY-n-(O)m |
| $C_nH_{2n+1}$—[H]—[H]—OCF$_2$—[O(F,F)]—(O)—$C_mH_{2m+1}$ | CCQIY-n-(O)m |
| $C_nH_{2n+1}$—[H]—[O]—CF$_2$O—[O(F,F)]—(O)—$C_mH_{2m+1}$ | CPQY-n-(O)m |
| $C_nH_{2n+1}$—[H]—[O]—OCF$_2$—[O(F,F)]—(O)—$C_mH_{2m+1}$ | CPQIY-n-Om |
| $C_nH_{2n+1}$—[H]—[=]—[O(F,F)]—(O)$C_mH_{2m+1}$ | CLY-n-(O)m |
| $C_nH_{2n+1}$—[H]—[O(F,F)]—[=]—$C_mH_{2m+1}$ | CYLI-n-m |
| $C_nH_{2n+1}$—[=]—[O(F,F)]—[=]—$C_mH_{2m+1}$ | LYLI-n-m |

TABLE D-continued
| Illustrative structures | |
|---|---|
| 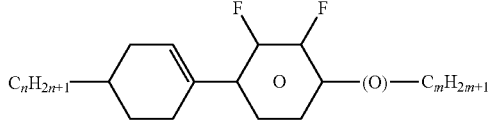 | LY-n-(O)m |
| 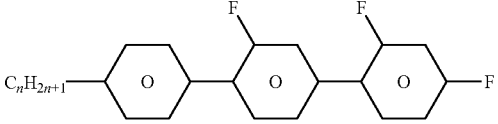 | PGIGI-n-F |
| 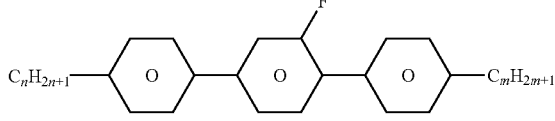 | PGP-n-m |
| 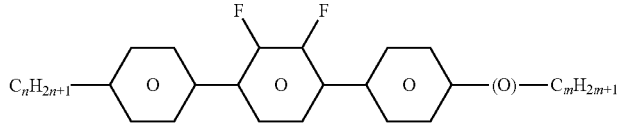 | PYP-n-(O)m |
| 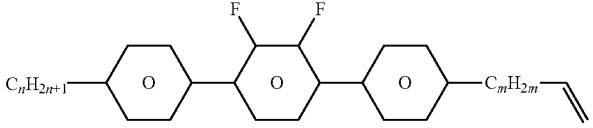 | PYP-n-mV |
| 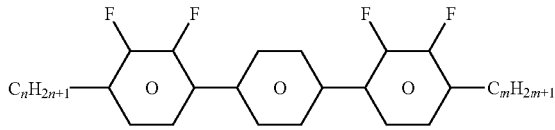 | YPY-n-m |
| 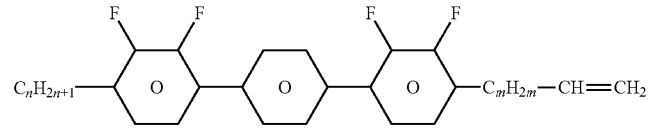 | YPY-n-mV |
|  | BCH-nm |
| 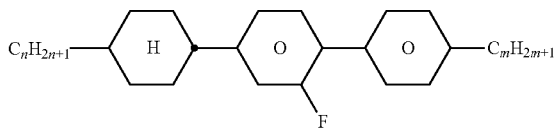 | BCH-nmF |
| 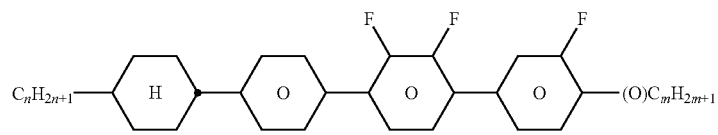 | CPYP-n-(O)m |
| 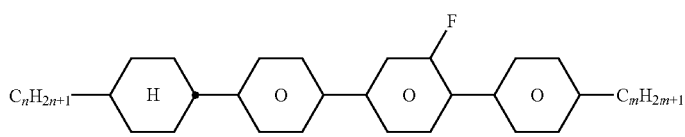 | CPGP-n-m |

TABLE D-continued

| Illustrative structures | |
|---|---|
| (structure) | CPYC-n-m |
| (structure) | CYYC-n-m |
| (structure) | CCYY-n-m |
| (structure) | CPYG-n-(O)m |
| (structure) | CBC-nm |
| (structure) | CBC-nmF |
| (structure) | CNap-n-Om |
| (structure) | CCNap-n-Om |
| (structure) | CENap-n-Om |
| (structure) | CTNap-n-Om |

TABLE D-continued

| Illustrative structures | |
|---|---|
| (structure) | CETNap-n-Om |
| (structure) | CK-n-F |
| (structure) | DFDBC-n(O)-(O)m |
| (structure) | C-DFDBF-n-(O)m |
| (structure) | B-n(O)-(O)m |
| (structure) | B(S)-n(O)-(O)m |
| (structure) | CC(CN)-n-m |
| (structure) | CC(CN)C-n-m |
| (structure) | PPC(CN)-n-m |
| (structure) | CPP(F,CN)-n-Om | in which n, m and l preferably, independently of one another, denote 1 to 7.

The following table, Table E, shows illustrative compounds which can optionally be used as stabilisers in the mesogenic media according to the present invention.
TABLE E
Table E shows possible stabilisers which can be added to the LC media according to the invention, wherein n denotes an integer from 1 to 12, preferably 1, 2, 3, 4, 5, 6, 7 or 8.
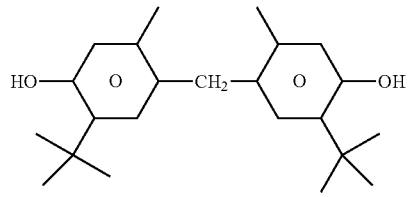
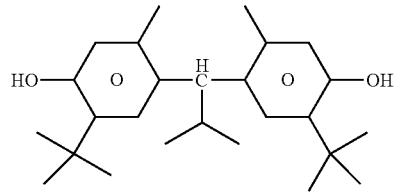
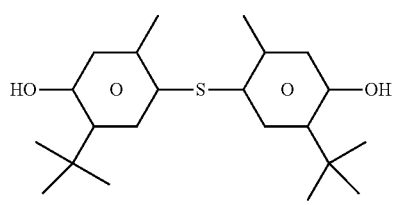
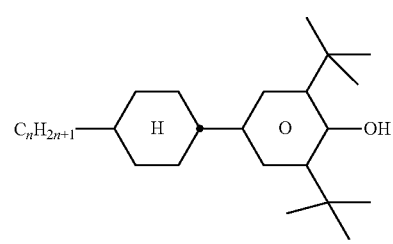
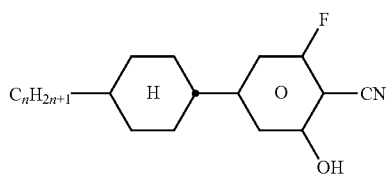
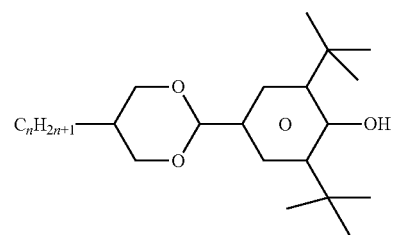
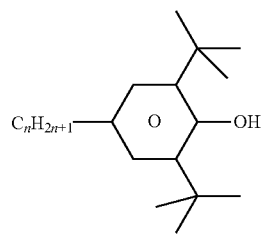
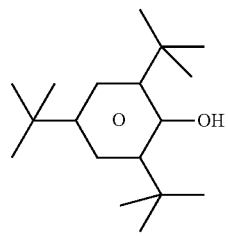
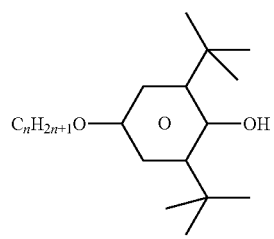
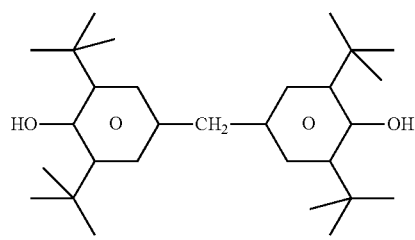
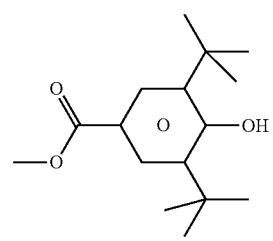
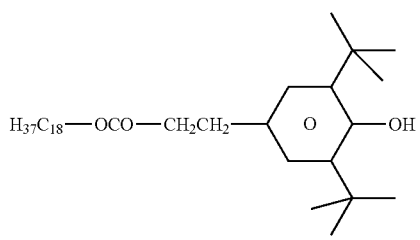

TABLE E-continued
Table E shows possible stabilisers which can be added to the LC media according to the invention, wherein n denotes an integer from 1 to 12, preferably 1, 2, 3, 4, 5, 6, 7 or 8.
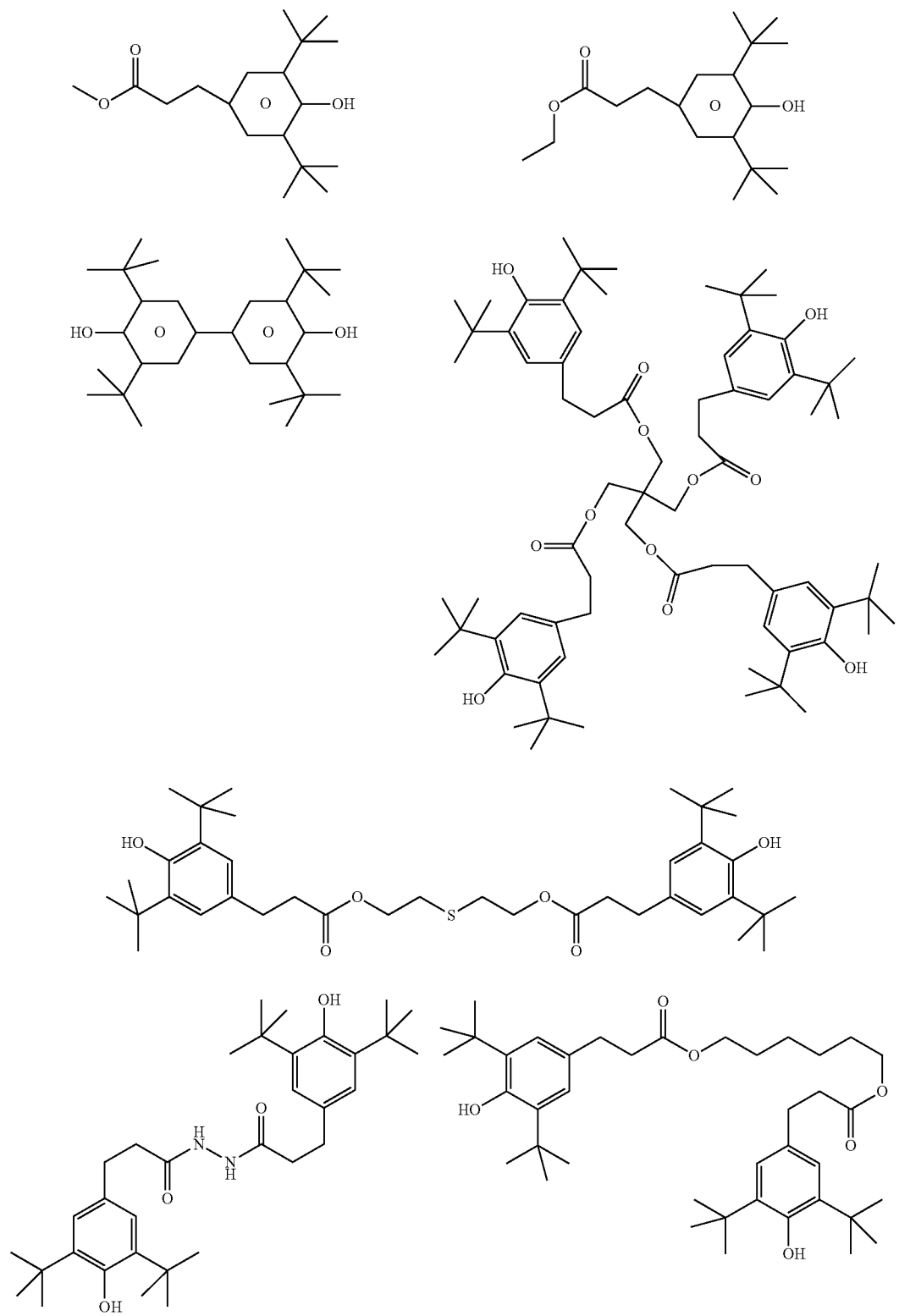

TABLE E-continued
Table E shows possible stabilisers which can be added to the LC media according to the invention, wherein n denotes an integer from 1 to 12, preferably 1, 2, 3, 4, 5, 6, 7 or 8.
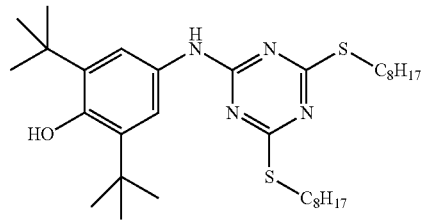
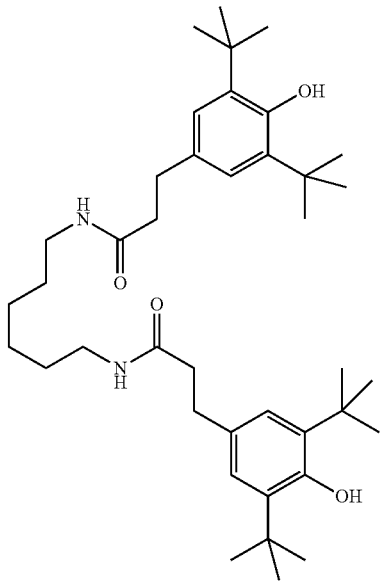 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
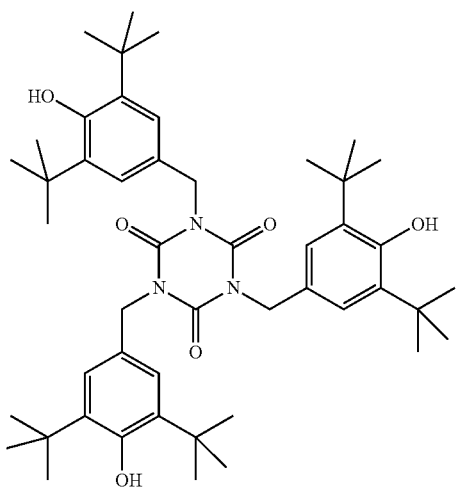 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
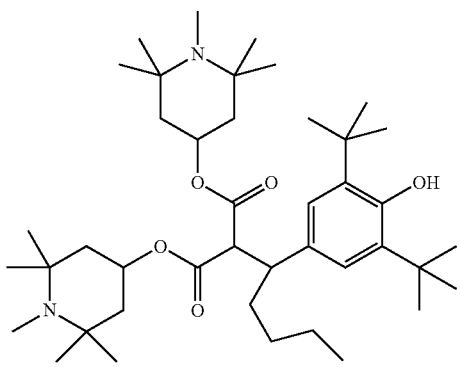 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
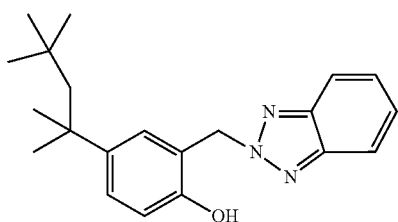 [SMILES: CC(C)(C)CC(C)(C)c1ccc(O)c(Cn2nc3ccccc3n2)c1]
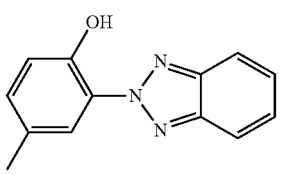 [SMILES: Cc1ccc(O)c(-n2nc3ccccc3n2)c1]
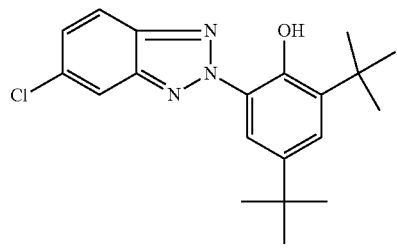 [SMILES: CC(C)(C)c1cc(-n2nc3ccc(Cl)cc3n2)c(O)c(C(C)(C)C)c1]
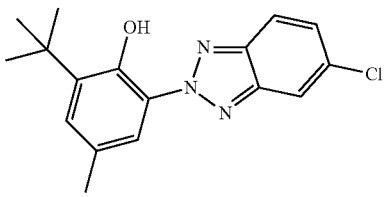 [SMILES: Cc1cc(-n2nc3ccc(Cl)cc3n2)c(O)c(C(C)(C)C)c1]

TABLE E-continued
Table E shows possible stabilisers which can be added to the LC media according to the invention, wherein n denotes an integer from 1 to 12, preferably 1, 2, 3, 4, 5, 6, 7 or 8.
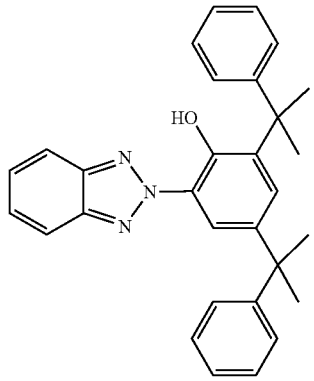 [SMILES: CC(C)(c1ccccc1)c1cc(-n2nc3ccccc3n2)c(O)c(C(C)(C)c2ccccc2)c1]
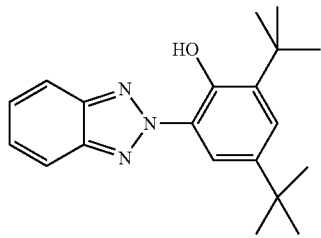 [SMILES: CC(C)(C)c1cc(-n2nc3ccccc3n2)c(O)c(C(C)(C)C)c1]
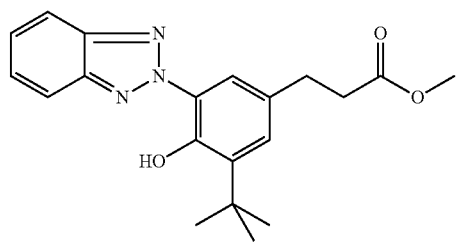 [SMILES: COC(=O)CCc1cc(-n2nc3ccccc3n2)c(O)c(C(C)(C)C)c1]
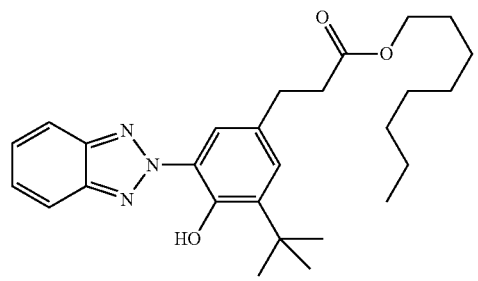 [SMILES: CCCCCCCCOC(=O)CCc1cc(-n2nc3ccccc3n2)c(O)c(C(C)(C)C)c1]
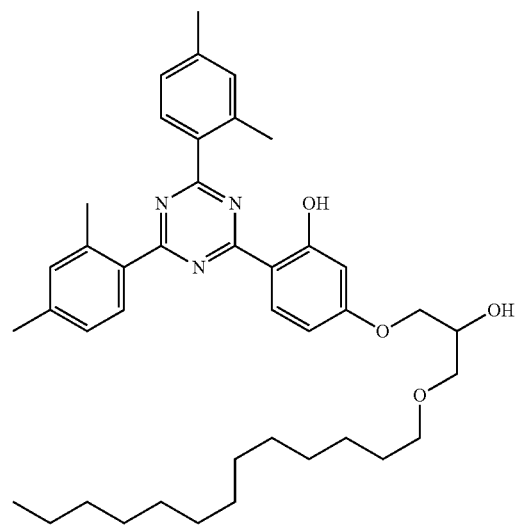

TABLE E-continued
Table E shows possible stabilisers which can be added to the LC media according to the invention, wherein n denotes an integer from 1 to 12, preferably 1, 2, 3, 4, 5, 6, 7 or 8.
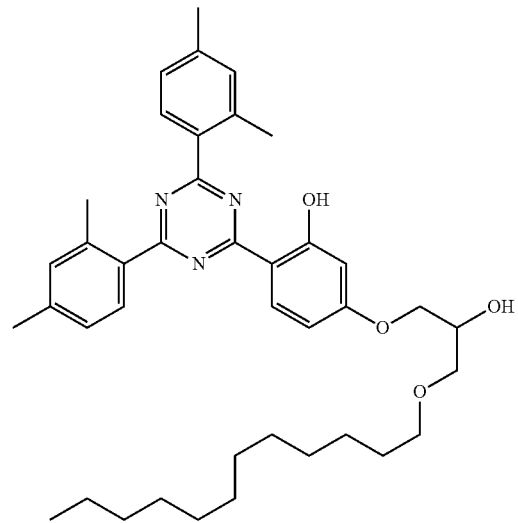
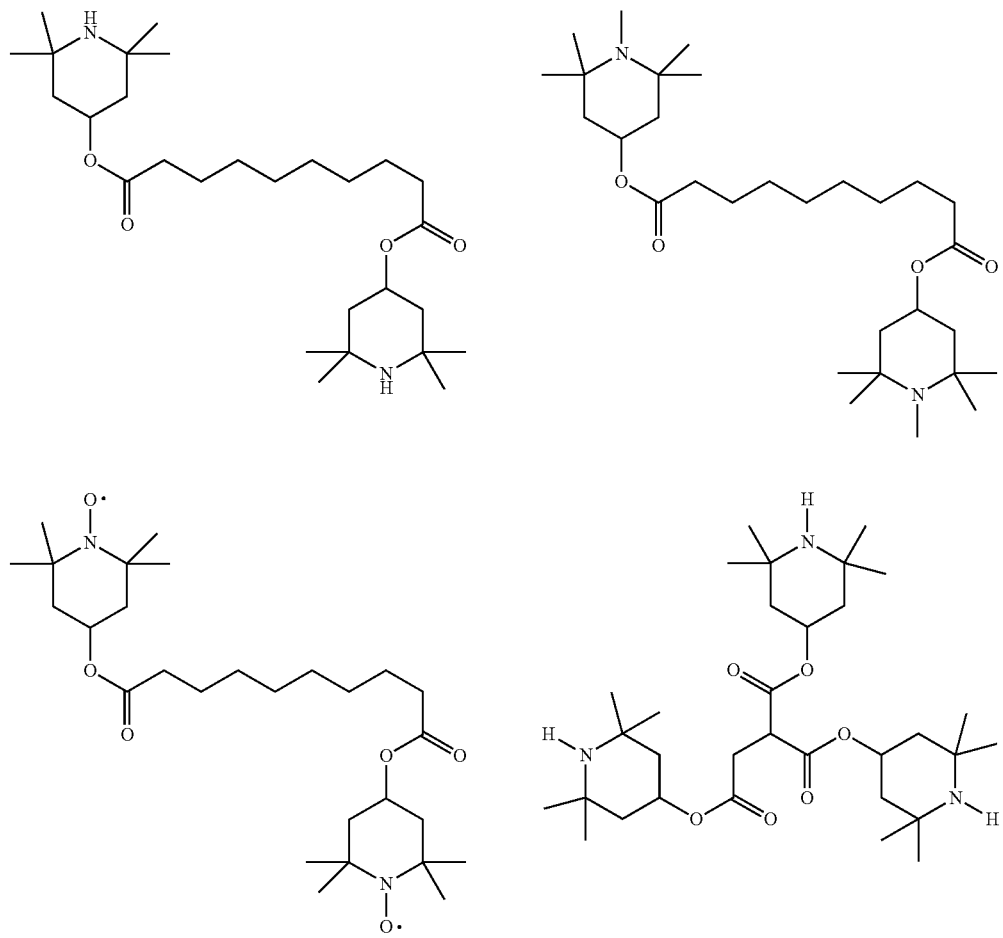

TABLE E-continued
Table E shows possible stabilisers which can be added to the LC media according to the invention, wherein n denotes an integer from 1 to 12, preferably 1, 2, 3, 4, 5, 6, 7 or 8.
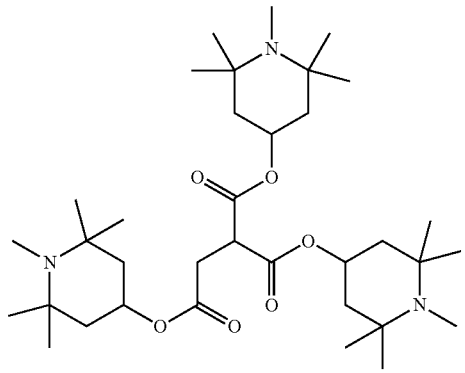
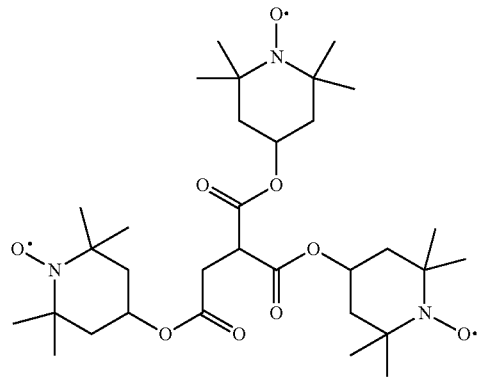
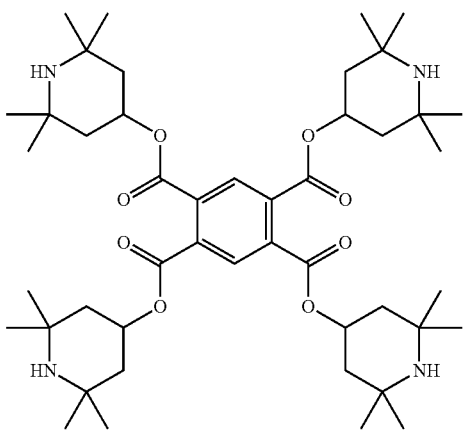
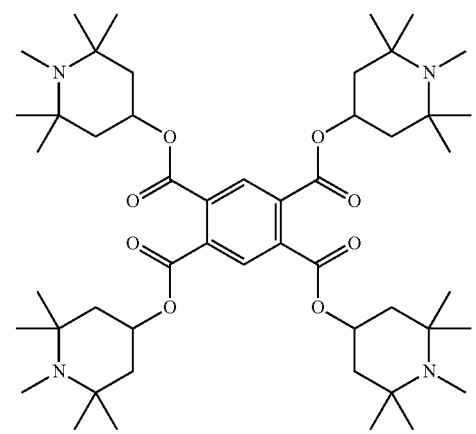
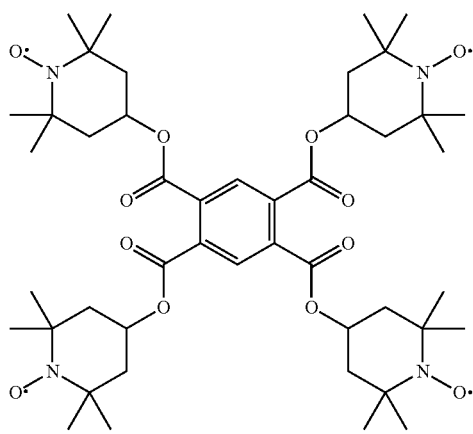

The LC media preferably comprise 0 to 10% by weight, in particular 1 ppm to 5% by weight, particularly preferably 1 ppm to 1% by weight, of stabilisers.
Table F below shows illustrative compounds which can preferably be used as chiral dopants in the mesogenic media according to the present invention.
TABLE F
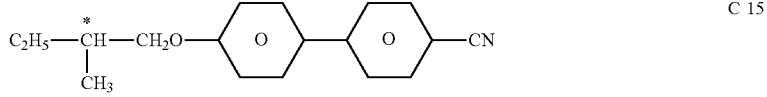
C 15
CB 15
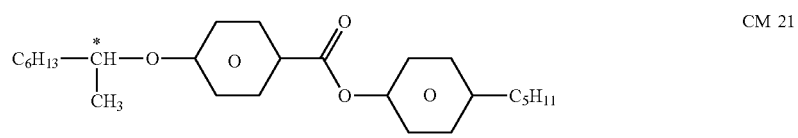
CM 21
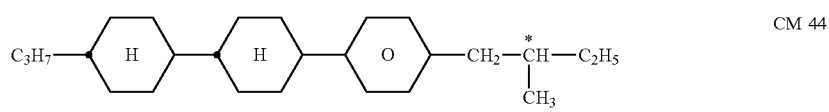
CM 44
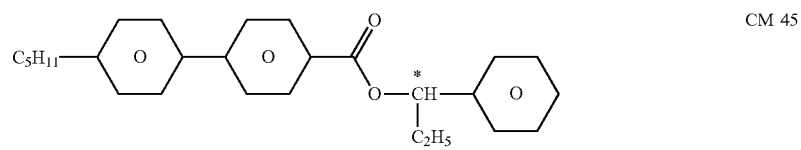
CM 45
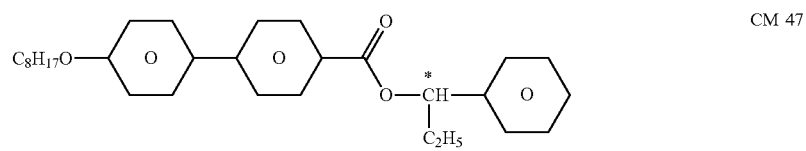
CM 47
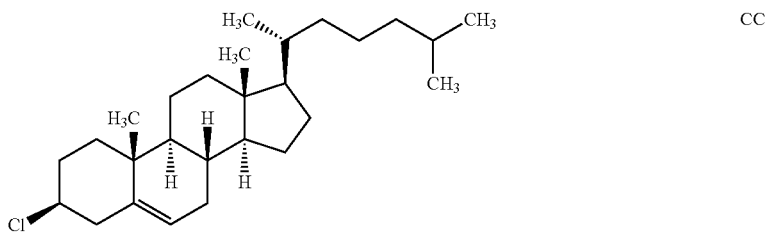
CC
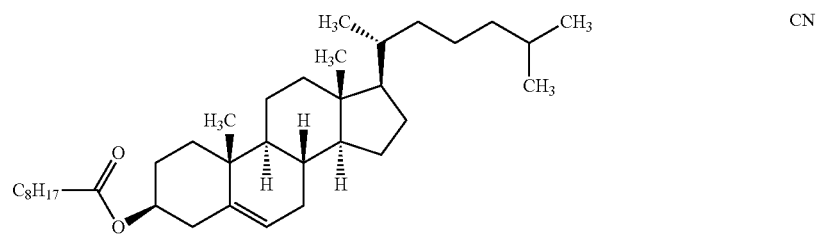
CN
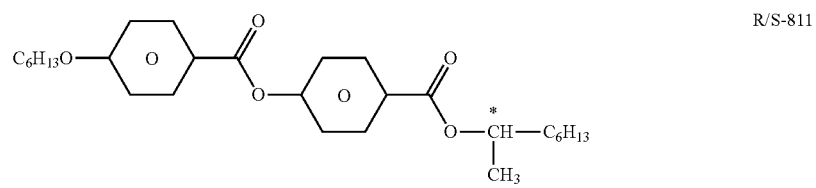
R/S-811

TABLE F-continued

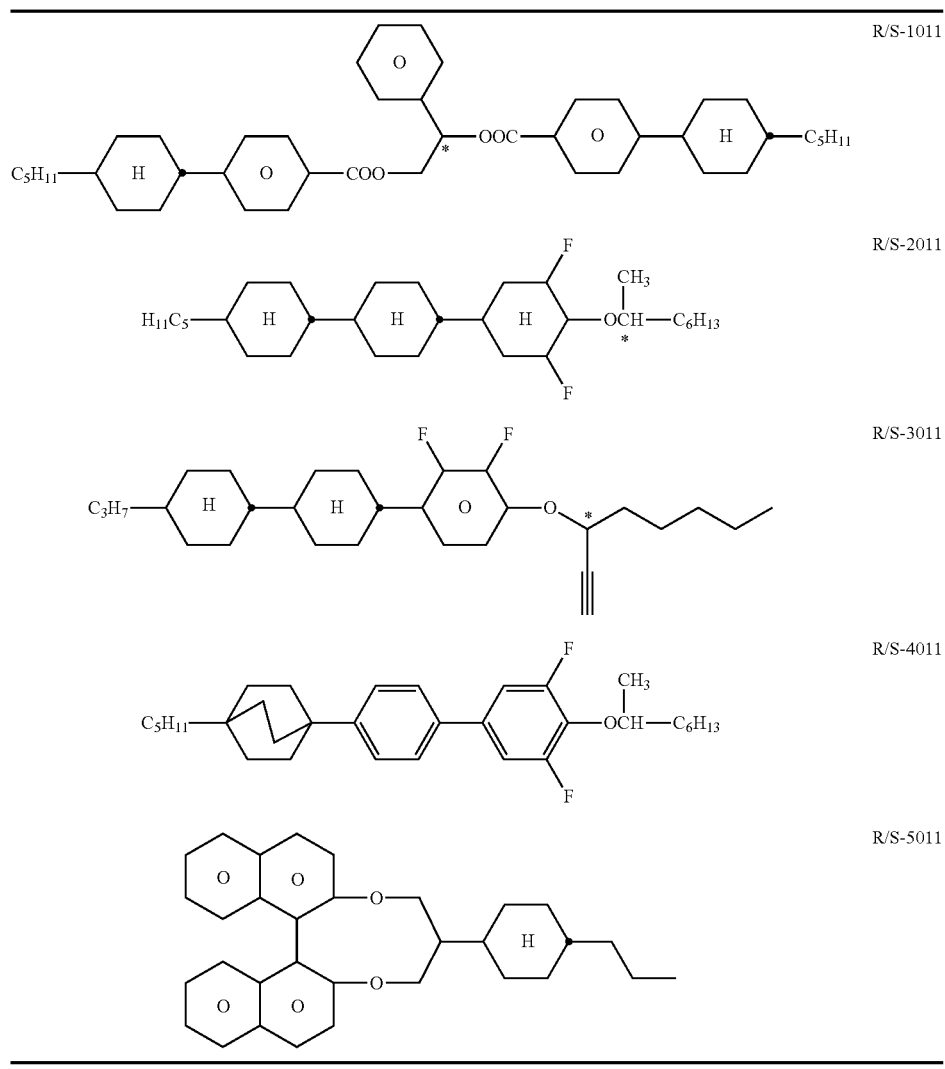

In a preferred embodiment of the present invention, the mesogenic media comprise one or more compounds selected from the group of compounds from Table F.

The mesogenic media according to the present invention preferably comprise two or more, preferably four or more, compounds selected from the group of compounds from the above Tables D, E and F.

The liquid-crystal media according to the present invention preferably comprise seven or more, preferably eight or more, individual compounds selected from the group of compounds from Table D, preferably three or more, particularly preferably four or more having different formulae selected from the formulae shown in Table D.

The LC media according to the invention may also comprise compounds in which, for example, H, N, O, Cl or F have been replaced by the corresponding isotopes.

All percent data and amount ratios given herein are percent by weight unless explicitly indicated otherwise.

All physical properties are determined in accordance with "Merck Liquid Crystals, Physical Properties of Liquid Crystals", Status November 1997, Merck KGaA, Germany, and apply for a temperature of 20° C., unless explicitly indicated otherwise. The value of $\Delta n$ is determined at 589 nm, and the value of $\Delta \varepsilon$ is determined at 1 kHz, unless explicitly indicated otherwise in each case. $n_e$ and $n_o$ are in each case the refractive indices of the extraordinary and ordinary light beam under the conditions indicated above.

The degree of anisotropy R is determined from the value for the extinction coefficient E(p) (extinction coefficient of the mixture in the case of parallel alignment of the molecules to the polarisation direction of the light) and the value for the extinction coefficient of the mixture E(s) (extinction coefficient of the mixture in the case of perpendicular alignment of the molecules to the polarisation direction of the light), in each case at the wavelength of the maximum of the absorption band of the dye in question. If the dye has a plurality of absorption bands, typically the strongest absorption band is selected. The alignment of the molecules of the mixture is achieved by an alignment layer, as known in the art. In order to eliminate influences by liquid-crystalline medium, other absorptions or reflections, each measurement is carried out against an identical mixture comprising no dye, and the value obtained is subtracted.

The measurement is carried out using linear-polarised light whose vibration direction is either parallel to the alignment direction (determination of E(p)) or perpendicular to the alignment direction (determination of E(s)). This can be achieved by a linear polariser, where the polariser is rotated with respect to the device in order to achieve the two different polarisation directions. The measurement of E(p) and E(s) is thus carried out via the rotation of the polarisation direction of the incident polarised light.

The degree of anisotropy R is calculated from the resultant values for E(s) and E(p) in accordance with the formula $$R=[E(p)-E(s)]/[E(p)+2*E(s)],$$

as indicated, inter alia, in "Polarized Light in Optics and Spectroscopy", D. S. Kliger et al., Academic Press, 1990. A detailed description of the method for the determination of the degree of anisotropy of liquid-crystalline media comprising a dichroic dye is also given in B. Bahadur, Liquid Crystals—Applications and Uses, Vol. 3, 1992, World Scientific Publishing, Section 11.4.2.

The following examples are merely illustrative of the present invention and they should not be considered as limiting the scope of the invention in any way. The examples and modifications or other equivalents thereof will become apparent to those skilled in the art in the light of the present disclosure.

EXAMPLES

In the Examples,
$V_o$ denotes threshold voltage, capacitive [V] at 20° C.,
$n_e$ denotes extraordinary refractive index at 20° C. and 589 nm,
$n_o$ denotes ordinary refractive index at 20° C. and 589 nm,
$\Delta n$ denotes optical anisotropy at 20° C. and 589 nm,
$\epsilon\|$ denotes dielectric permittivity parallel to the director at 20° C. and 1 kHz,
$\Delta\perp$ denotes dielectric permittivity perpendicular to the director at 20° C. and 1 kHz,
$\Delta\epsilon$ denotes dielectric anisotropy at 20° C. and 1 kHz,
cl.p., T(N,I) denotes clearing point [° C.],
$\gamma_1$ denotes rotational viscosity measured at 20° C. [mPa·s], determined by the rotation method in a magnetic field,
$K_1$ denotes elastic constant, "splay" deformation at 20° C. [pN],
$K_2$ denotes elastic constant, "twist" deformation at 20° C. [pN],
$K_3$ denotes elastic constant, "bend" deformation at 20° C. [pN], The term "threshold voltage" for the present invention relates to the capacitive threshold ($V_0$), unless explicitly indicated otherwise. In the Examples, as is generally usual, the optical threshold can also be indicated for 10% relative contrast ($V_{10}$).

Synthesis Examples

Compounds 1 to 9 are prepared according to the following scheme.

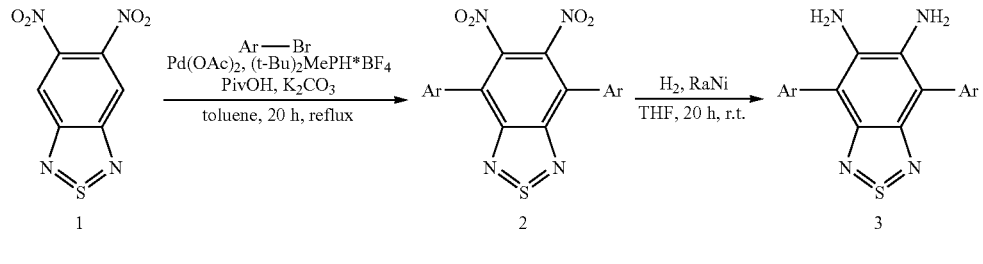

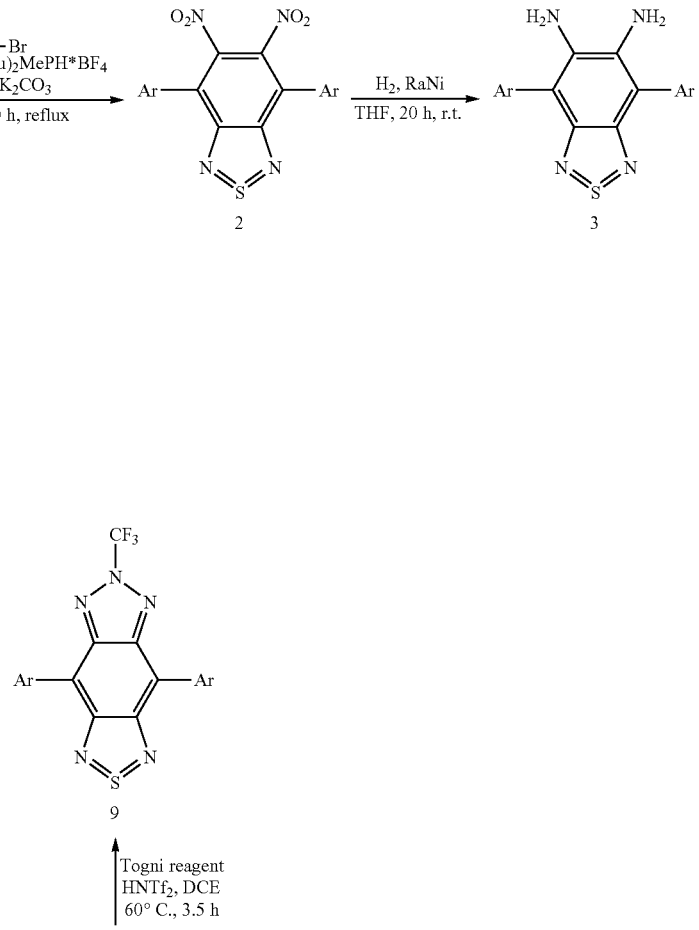

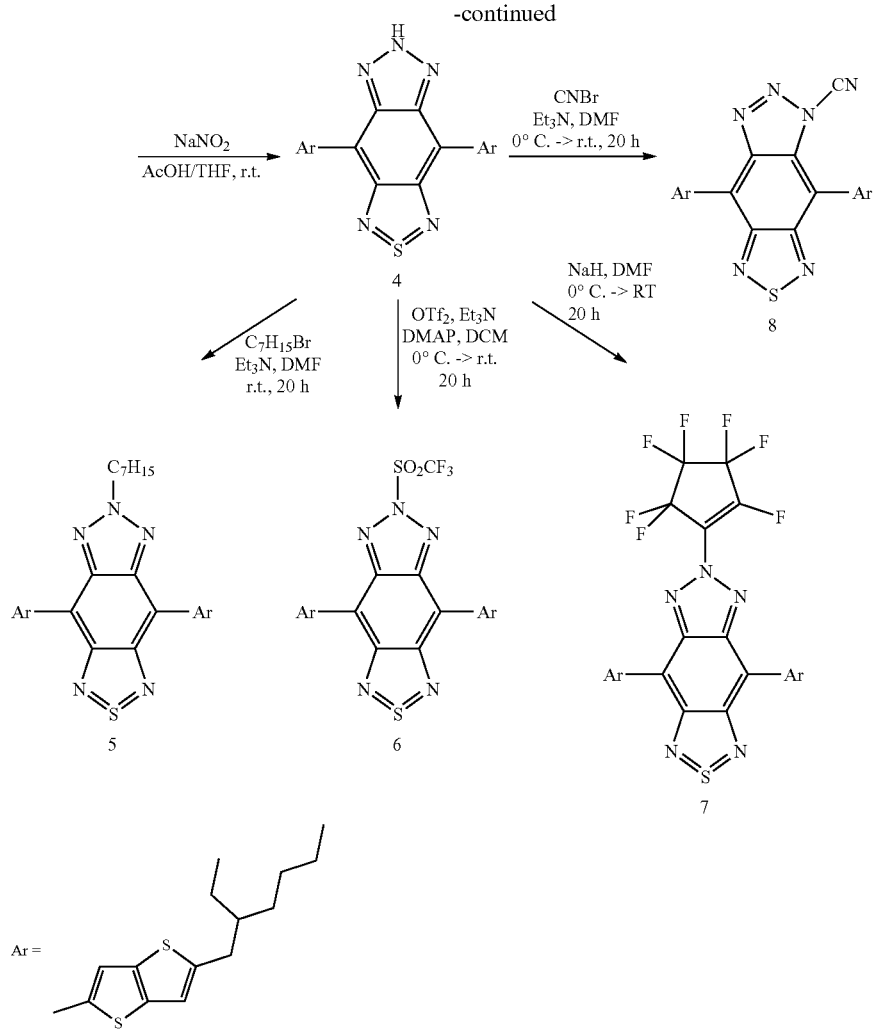

Synthesis Example 1

Preparation of 5,6-dinitrobenzo[2,1,3]benzothiadiazole (Compound 1)

The precursors for compound 1 are prepared according to methods known in the art, see e.g. G. W. H. Cheeseman, Quinoxalines and Related Compounds. Part VI, 1962, 1170-1176.

A 1 l four-necked apparatus with a stirrer and a thermometer is charged with 15.00 g of 4,5-dinitro-1,2-phenylenediamine (55.3 mmol) in 125 ml of dichloromethane under a nitrogen atmosphere and cooled to −10° C. Then 30.00 ml of triethylamine (221 mmol) and 8.00 ml of thionyl chloride (110 mmol) are consecutively added dropwise, wherein the temperature does not exceed 10° C. The mixture is slowly warmed up to room temperature and then stirred for 20 h. The reaction solution is added to 200 ml of ice water, chloroform (300 ml) is added, and the phases are separated. The aqueous phase is extracted once with chloroform, the combined organic phases are washed once with water, dried over sodium sulphate and filtered, and the solvent is removed under reduced pressure. The residue is subjected to chromatography over silica gel using toluene and then recrystallized from 100 ml of heptane/toluene (3:1) and dried under vacuum. The product is obtained as beige-coloured crystals.

Synthesis Example 2

Preparation of 4,7-bis-[5-(2-ethylhexyl)-thieno[3,2-b]thiophen-2-yl]-5,6-dinitrobenzo[2,1,3]thiadiazol (Compound 2)

A 250 ml brown glass four-necked apparatus with a stirrer, a thermometer and a reflux condenser is charged with 2.00 g of 5,6-dinitrobenzo[2,1,3]benzothiadiazole (8.44 mmol), 6.30 g of 2-bromo-5-(2-ethylhexyl)-thieno[3,2-b] thienothiophene (18.6 mmol), 3.50 g of potassium carbonate (25.3 mmol), 862 mg of pivalic acid (8.44 mmol) and 423 mg of di-tert-butylmethylphosphoniumtetrafluoroborate [(t-Bu)$_2$MeP*BF$_4$] (1.70 mmol) in 60 ml of toluene under a nitrogen atmosphere. Then 190 mg of palladium(II) acetate (0.84 mmol) are added, and the mixture is heated under reflux for 20 h. Then the reaction solution is cooled to room temperature, 20 ml of dichloromethane are added, and filtration using a thin layer of celite is carried out. The filtrate is concentrated under reduced pressure. The crude product is subjected to chromatography over silica gel using toluene/heptane (1:2). The product is obtained as a red oil.

Synthesis Example 3

Preparation of 4,7-bis-[5-(2-ethylhexyl)-thieno[3,2-b]thiophen-2-yl]-benzo[2,1,3]thiadiazole-5,6-diamine (Compound 3)

In a reaction vessel 1.65 g of 4,7-bis-[5-(2-ethylhexyl)-thieno[3,2-b]thiophen-2-yl]-5,6-dinitro-benzo[2,1,3]thiadiazole (Compound 2, 2.07 mmol) are dissolved in 50 ml tetrahydrofuran, 1.00 g of Raney nickel are added and hydrogen is introduced. After 6 h a further 1.00 g of Raney nickel is added and stirring for another 17 h at room temperature is continued, wherein in total 188 ml of hydrogen are used. The reaction mixture is then filtered and the residue is washed with tetrahydrofuran. The solvent is removed from the combined filtrate under reduced pressure. The product is obtained is a yellowish brown solid.

Synthesis Example 4

Preparation of 4,7-bis-[5-(2-ethylhexyl)-thieno[3,2-b]thiophen-2-yl]-2H-benzo[d]-[1,2,3]-triazolo-[2,1,3]-thiadiazole (Compound 4)

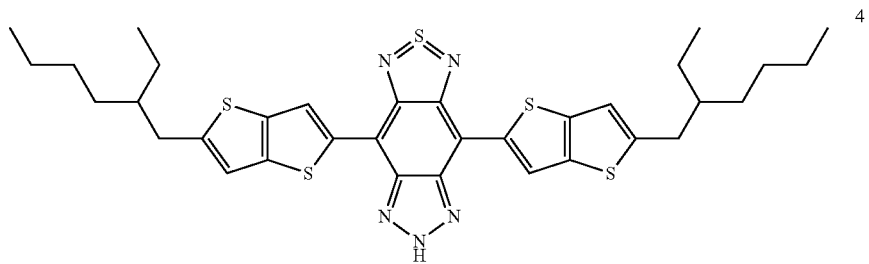 [SMILES: CCCCC(CC)Cc1cc2sc(-c3c4c(c(-c5cc6sc(CC(CC)CCCC)cc6s5)c5n[nH]nc35)N=S=N4)cc2s1]

4

A 25 ml two-necked flask is charged under a nitrogen atmosphere with 350 mg of 4,7-bis-[5-(2-ethylhexyl)-thieno[3,2-b]thiophen-2-yl]-5,6-diaminobenzo[2,1,3]thiadiazole (0.52 mmol) in 3 ml concentrated acetic acid and 3 ml tetrahydrofuran. Then 40 mg of sodium nitrite (0.58 mmol) in 2 ml are slowly added dropwise. The mixture is stirred for 1.5 h at room temperature, wherein a dark solid precipitates. Then 20 ml of water are added, the mixture is cooled to 0° C., and the precipitate is filtered and dried. The crude product is subjected to chromatography over silica gel using toluene and then recrystallized from 15 ml of heptane/toluene (1:2). The product is obtained as a dark blue solid.

The product exhibits an absorption maximum at 635 nm with an average extinction coefficient of 450 [%*cm] and only minimal fluorescence. The degree of anisotropy R as determined in Host Mixture H-1 as given below is 0.70.

Synthesis Example 5

Preparation of 4,7-bis-[5-(2-ethylhexyl)-thieno[3,2-b]thiophen-2-yl]-2-heptyl-benzo[d]-[1,2,3]-triazolo-[2,1,3]-thiadiazole (Compound 5)

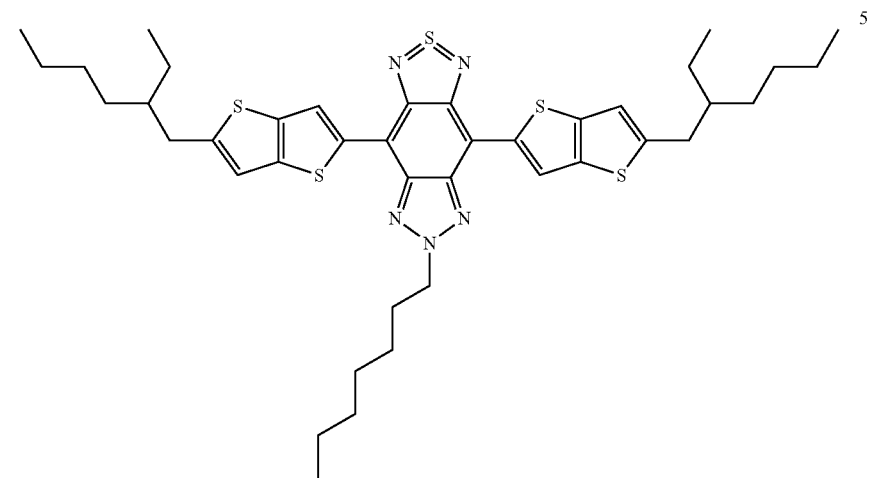 [SMILES: CCCCCCCn1nc2c(-c3cc4sc(CC(CC)CCCC)cc4s3)c3c(c(-c4cc5sc(CC(CC)CCCC)cc5s4)c2n1)N=S=N3]

5

A 50 ml two-necked flask is charged under a nitrogen atmosphere with 500 mg of 4,7-bis-[5-(2-ethylhexyl)-thieno[3,2-b]thiophen-2-yl]-2H-benzo[d]-[1,2,3]-triazolo-[2,1,3]-thiadiazole (0.74 mmol) in 15 ml dimethylformamide. Then 0.12 ml of triethylamine (0.84 mmol) is added dropwise. The mixture is stirred for 1 h at room temperature, then 0.13 ml of 1-bromoheptane (0.84 mmol) is added dropwise and stirring at room temperature is continued for 20 h. Then 20 ml of water and 10 ml of dichloromethane are added, and the phases are separated. The aqueous phase is extracted twice with 20 ml dichloromethane. The combined organic phases are washed twice with 50 ml water, dried over sodium sulphate and filtered, and the solvent is removed under reduced pressure. The crude product is subjected twice to chromatography over silica gel using heptane/toluene (4:1) and then recrystallized from 10 ml of heptane. The product is obtained as blue-black needle-shaped crystals.

The product exhibits an absorption maximum at 720 nm with an average extinction coefficient of 450 [%*cm] and only minimal fluorescence. The degree of anisotropy R as determined in Host Mixture H-1 as given below is 0.67.

Synthesis Example 6

Preparation of 4,7-bis-[5-(2-ethylhexyl)-thieno[3,2-b]thiophen-2-yl]-2-triflyl-benzo[d]-[1,2,3]-triazolo-[2,1,3]-thiadiazole (Compound 6)

A 25 ml two-necked flask is charged under a nitrogen atmosphere with 500 mg of 4,7-bis-[5-(2-ethylhexyl)-thieno[3,2-b]thiophen-2-yl]-2H-benzo[d]-[1,2,3]-triazolo-[2,1,3]-thiadiazole (0.74 mmol) in 4.7 ml of dichloromethane, and the mixture is cooled to 0° C. Then 0.14 ml of triethylamine Synthesis Example 7

Preparation of 4,7-bis-[5-(2-ethylhexyl)-thieno[3,2-b]thiophen-2-yl]-2-(1,3,3,4,4,5,5-heptafluoro-2-cyclopentenyl)-benzo[d]-[1,2,3]-triazolo-[2,1,3]-thiadiazole (Compound 7)

A 50 ml two-necked flask is charged under a nitrogen atmosphere with 200 mg of 4,7-bis-[5-(2-ethylhexyl)-thieno[3,2-b]thiophen-2-yl]-2H-benzo[d]-[1,2,3]-triazolo-[2,1,3]-thiadiazole (0.29 mmol) in 2.2 ml dimethylformamide, and the mixture is cooled to 0° C. Then 17.7 mg of sodium hydride (60% suspension in paraffin oil, 0.44 mmol) are added in portions and the mixture is stirred for 30 minutes. Then 81.3 mg of 1,2,3,3,4,4,5,5-octafluorocyclopentene (0.38 mmol) in 1 ml dimethylformamide are added dropwise, wherein the mixture changed to a green colour. The cooling is stopped and the mixture is stirred at room temperature for 20 h. Then 20 ml of a saturated ammonium chloride solution are added to the reaction mixture. 10 ml of methyl tert-butyl ether are added, the phases are separated, and the aqueous phase is extracted twice with 20 ml methyl tert-butyl ether. The combined organic phases are washed twice with 50 ml water, dried over sodium sulphate and filtered, and the solvent is removed under reduced pressure. The crude product is subjected to chromatography over silica gel using heptane/toluene (1:1) and then to chromatography over silica gel using heptane/toluene (4:1). The product is obtained as a dark green oil.

The product exhibits an absorption maximum at 724 nm and only minimal fluorescence.

Synthesis Example 8

Preparation of 4,7-bis-[5-(2-ethylhexyl)-thieno[3,2-b]thiophen-2-yl]-2-cyano-benzo[d]-[1,2,3]-triazolo-[2,1,3]-thiadiazol (Compound 8)

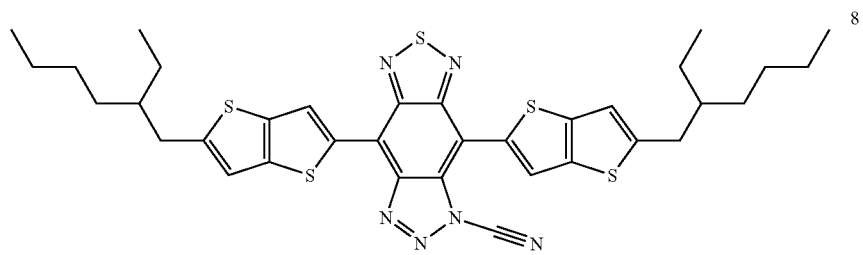 [SMILES: CCCCC(CC)Cc1cc2sc(-c3c4nsnc4c(-c4cc5sc(CC(CC)CCCC)cc5s4)c4c3nnn4C#N)cc2s1]

8

(1.03 mmol) and 1.80 mg of 4-(dimethylamino)pyridine (0.01 mmol) are added dropwise. The mixture is stirred for 15 minutes, and then 0.17 ml of trifluoromethanesulfonic anhydride (1.03 mmol) is added dropwise, wherein the mixture immediately changes to a green colour. The cooling is stopped and the mixture is stirred at room temperature for 20 h. Then 20 ml of water and 10 ml of dichloromethane are added to the reaction solution, the phases are separated, and the aqueous phase is extracted twice with 20 ml dichloromethane. The combined organic phases are washed twice with 50 ml water, dried over sodium sulphate and filtered, and the solvent is removed under reduced pressure. The crude product is recrystallized from 15 ml of heptane/chlorobutane (2:1). The product is obtained as dark green residue.

The product exhibits an absorption maximum at 844 nm and only minimal fluorescence.

A 50 ml two-necked flask is charged under a nitrogen atmosphere with 1.00 g of 4,7-bis-[5-(2-ethylhexyl)-thieno[3,2-b]thiophen-2-yl]-2H-benzo[d]-[1,2,3]-triazolo-[2,1,3]-thiadiazole (1.47 mmol) in 11.5 ml dimethylformamide. Then 0.23 ml of triethylamine (1.68 mmol) are added dropwise. The mixture is stirred for 1 h, and then 156 mg of cyanogen bromide (1.47 mmol) is added. The mixture is stirred at room temperature for 20 h. 50 ml of water are added, and the precipitating solid is filtered, washed with water and dried. The crude product is subjected to chromatography over silica gel using heptane/toluene (4:1) and then recrystallized from 15 ml of heptane/toluene (9:1). The product is obtained as a dark, almost black solid.

The product exhibits an absorption maximum at 612 nm with an average extinction coefficient of 277 [%*cm] and only minimal fluorescence. The degree of anisotropy R as determined in Host Mixture H-2 as given below is 0.73.

Synthesis Example 9

Preparation of 4,7-bis-[5-(2-ethylhexyl)-thieno[3,2-b]thiophen-2-yl]-2-trifluoromethyl-benzo[d]-[1,2,3]-triazolo-[2,1,3]-thiadiazole (Compound 9)

A 50 ml two-necked flask is charged under a nitrogen atmosphere with 500 mg of 4,7-bis-[5-(2-ethylhexyl)-thieno[3,2-b]thiophen-2-yl]-2H-benzo[d]-[1,2,3]-triazolo-[2,1,3]-thiadiazole (0.74 mmol) and 267 mg of 3,3-dimethyl-1-(trifluoromethyl)-1,2-benziodoxole (0.81 mmol) in 10 ml dichloroethane. Then 21 mg of bis(trifluoromethanesulfonyl)amine (0.07 mmol) in 1 ml dichlorethane are added dropwise. The mixture is heated to 60° C. and stirred for 3.5 h auf 60° C. The mixture is then cooled to room temperature, and the solvent is removed under reduce pressure. The crude product is subjected to chromatography over silica gel using heptane/toluene (4:1) and then recrystallized from 15 ml of heptane/toluene (9:1). The product is obtained a dark blue solid.

The product exhibits an absorption maximum at 610 nm and only minimal fluorescence.

Synthesis Examples 10, 11, 12, 13 and 14

In an analogy to the Synthesis Examples 1 to 9 above, Compounds 10 to 14 are prepared according to the following scheme, wherein Ar has the meaning as given in the Synthesis Examples 1 to 9.

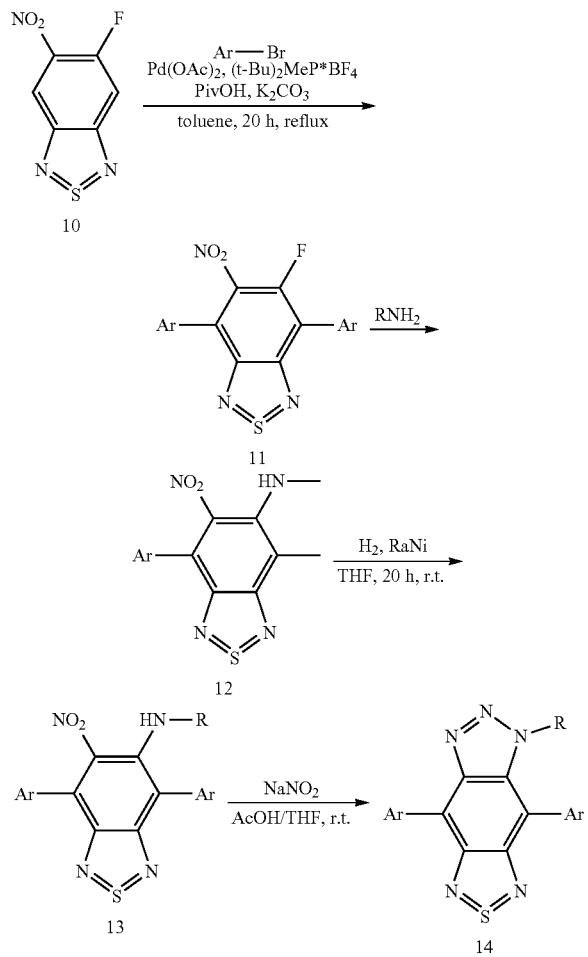

Synthesis Examples 15 to 22

In accordance with Synthesis Examples 2 to 9, compounds are prepared wherein for Ar—Br 2-bromo-5-[4-(2-ethylhexyl)phenyl]thiophene is used instead of 2-bromo-5-(2-ethylhexyl)-thieno[3,2-b]thienothiophene.

Use Examples

The dyes prepared are investigated with respect to their physical properties and their suitability for use in devices for regulating energy transmission.

Reference Example 1

A liquid-crystal base mixture B-1 is prepared and characterized with respect to its general physical properties, having the composition and properties as indicated in the following table.

| | | | |
|---|---|---|---|
| CPG-3-F | 5.00% | clearing point [° C.]: | 114.5 |
| CPG-5-F | 5.00% | $\Delta n$ [589 nm, 20° C.]: | 0.135 |
| CPU-3-F | 15.00% | $n_e$ [589 nm, 20° C.]: | 1.63 |
| CPU-5-F | 15.00% | $\Delta \varepsilon$ [1 kHz, 20° C.]: | 11.3 |
| CP-3-N | 16.00% | $\varepsilon_\perp$ [1 kHz, 20° C.]: | 4.2 |
| CP-5-N | 16.00% | $K_1$ [pN, 20° C.]: | 13.4 |
| CCGU-3-F | 7.00% | $K_3$ [pN, 20° C.]: | 18.5 |
| CBC-33F | 4.00% | $V_0$ [V, 20° C.]: | 1.15 |
| CBC-53F | 4.00% | | |
| CBC-55F | 4.00% | | |
| CCZPC-3-3 | 3.00% | | |
| CCZPC-3-4 | 3.00% | | |
| CCZPC-3-5 | 3.00% | | |
| $\Sigma$ 100.00% | | | |

A host mixture H-1 is prepared by mixing 99.97% of mixture B-1 with 0.03% of the compound of formula

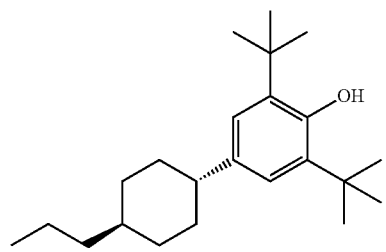

Examples 1, 2, 3 and 4

The following mixtures M-1, M-2, M-3 and M-4 are prepared based on the host mixture H-1, wherein the following dichroic dye compounds are added according to the following Table and wherein BT-1 and BT-2 are compounds of formula BT-1 and respectively BT-2 as given above.

| | M-1 | M-2 | M-3 | M-4 |
|---|---|---|---|---|
| H-1 | 98.716% | 98.365% | 98.024% | 97.290% |
| BT-1 | 0.167% | 0.250% | 0.066% | 0.093% |
| BT-2 | 0.261% | 0.310% | 0.464% | 0.608% |
| Compound 4 | 0.039% | 0.119% | 0.473% | 0.915% |
| Compound 5 | 0.412% | 0.345% | 0.973% | 1.094% |
| Compound 8 | 0.405% | 0.611% | — | — |

The mixtures M-1, M-2, M-3 and M-4 are respectively filled into electrically switchable devices having a double cell set-up where the switching layers have a thickness of 25 μm and the performance for the bright state and the dark state are evaluated. Measurements are performed according to norm EN410.

|  | M-1 | M-2 | M-3 | M-4 |
|---|---|---|---|---|
| light transmittance $\tau_v$ (dark state) | 10% | 4.5% | 10% | 5% |
| light transmittance $\tau_v$ (bright state) | 56% | 47% | 51% | 40% |
| solar direct transmittance $\tau_e$ (dark state) | 44% | 41% | 40% | 38% |
| solar direct transmittance $\tau_e$ (bright state) | 68% | 64% | 58% | 52% |
| chromaticity coordinate x (dark state) | 0.312 | 0.313 | 0.313 | 0.313 |
| chromaticity coordinate y (dark state) | 0.328 | 0.329 | 0.329 | 0.329 |
| chromaticity coordinate x (bright state) | 0.317 | 0.320 | 0.303 | 0.299 |
| chromaticity coordinate y (bright state) | 0.335 | 0.337 | 0.337 | 0.340 |

The mixtures M-1, M-2, M-3 and M-4 are well suited for the use in devices for regulating the passage of energy from an outside space into an inside space, for example in windows.

Reference Example 2

A liquid-crystal host mixture H-2 is prepared and characterized with respect to its general physical properties, having the composition and properties as indicated in the following table.

| CPG-3-F | 8.00% | clearing point [° C.]: | 114 |
|---|---|---|---|
| CPG-5-F | 8.00% | Δn [589 nm, 20° C.]: | 0.130 |
| CPU-5-F | 14.00% | $n_e$ [589 nm, 20° C.]: | 1.62 |
| CPU-7-F | 11.00% | Δε [1 kHz, 20° C.]: | 10.0 |
| CP-5-N | 18.00% | $\varepsilon_\perp$ [1 kHz, 20° C.]: | 4.0 |
| CP-7-N | 13.00% | | |
| CCGU-3-F | 7.00% | | |
| CC-3-O3 | 2.00% | | |
| CBC-33F | 4.00% | | |
| CBC-53F | 4.00% | | |
| CBC-55F | 3.00% | | |
| CCZPC-3-3 | 3.00% | | |
| CCZPC-3-4 | 3.00% | | |
| CCZPC-3-5 | 2.00% | | |
| Σ | 100.00% | | |

Reference Example 3

A mixture H-3 is prepared by mixing 99.92% of mixture H-2 as described in Reference Example 2 above with 0.05% of the compound of formula S-811 as described in Table F above and with 0.03% of the compound of formula

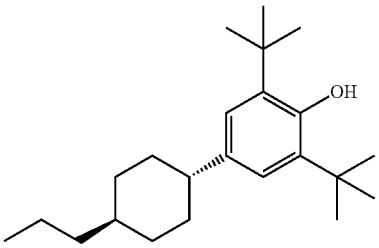

Reference Example 4

A mixture H-4 is prepared by mixing 99.80% of mixture H-2 as described in Reference Example 2 above with 0.10% of the compound of formula

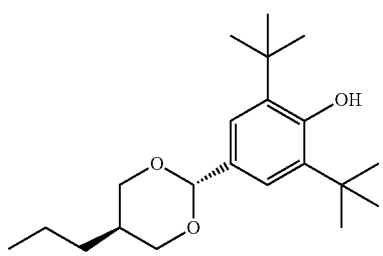 [SMILES: CCC[C@H]1CO[C@H](c2cc(C(C)(C)C)c(O)c(C(C)(C)C)c2)OC1]

and 0.10% of the compound of formula

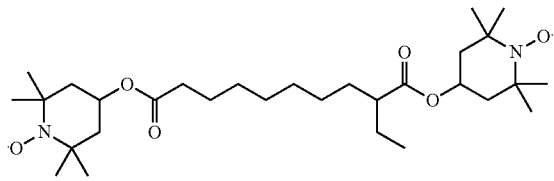

Reference Example 5

A liquid-crystal base mixture B-5 is prepared and characterized with respect to its general physical properties, having the composition and properties as indicated in the following table.

| CY-3-O2 | 9.00% | clearing point [° C.]: | 110.5 |
|---|---|---|---|
| CY-3-O4 | 9.00% | Δn [589 nm, 20° C.]: | 0.132 |
| CY-5-O2 | 12.00% | $n_e$ [589 nm, 20° C.]: | 1.62 |
| CY-5-O4 | 8.00% | Δε [1 kHz, 20° C.]: | −4.9 |
| CCY-3-O2 | 5.00% | $\varepsilon_\perp$ [1 kHz, 20° C.]: | 8.8 |
| CCY-3-O3 | 5.00% | $K_1$ [pN, 20° C.]: | 16.8 |
| CCY-4-O2 | 5.00% | $K_3$ [pN, 20° C.]: | 20.4 |
| CPY-2-O2 | 7.00% | $V_0$ [V, 20° C.]: | 2.14 |
| CPY-3-O2 | 6.00% | | |
| PYP-2-3 | 12.00% | | |
| CCP-V-1 | 6.00% | | |
| CCZPC-3-3 | 3.00% | | |
| CCZPC-3-4 | 3.00% | | |
| CBC-33F | 5.00% | | |
| CBC-53F | 5.00% | | |
| Σ | 100.00% | | |

A host mixture H-5 is prepared by mixing 99.97% of mixture B-5 with 0.03% of the compound of formula

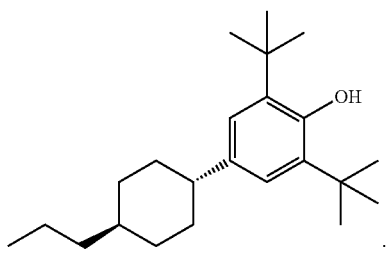 [SMILES: CCC[C@H]1CC[C@H](c2cc(C(C)(C)C)c(O)c(C(C)(C)C)c2)CC1]

Reference Example 6

A liquid-crystal host mixture H-6 is prepared and characterized with respect to its general physical properties, having the composition and properties as indicated in the following table.

| | | | |
|---|---|---|---|
| CY-3-O4 | 25.00% | clearing point [° C.]: | 75.4 |
| CCY-3-O2 | 6.00% | $\Delta n$ [589 nm, 20° C.]: | 0.100 |
| CCY-3-O3 | 7.00% | $n_e$ [589 nm, 20° C.]: | 1.58 |
| CPY-2-O2 | 8.00% | $\Delta\varepsilon$ [1 kHz, 20° C.]: | −3.0 |
| CPY-3-O2 | 8.00% | $\varepsilon_\perp$ [1 kHz, 20° C.]: | 6.4 |
| PYP-2-3 | 3.00% | $K_1$ [pN, 20° C.]: | 12.8 |
| CC-3-V1 | 9.00% | $K_3$ [pN, 20° C.]: | 14.4 |
| CC-3-V | 25.00% | $V_0$ [V, 20° C.]: | 2.32 |
| BCH-32 | 9.00% | | |
| Σ | 100.00% | | |

Reference Example 7

A liquid-crystal host mixture H-7 is prepared and characterized with respect to its general physical properties, having the composition and properties as indicated in the following table.

| | | | |
|---|---|---|---|
| CCU-1-F | 5.00% | clearing point [° C.]: | 85 |
| CCU-2-F | 8.00% | $\Delta n$ [589 nm, 20° C.]: | 0.071 |
| CCU-3-F | 10.00% | $n_e$ [589 nm, 20° C.]: | 1.55 |
| CCQU-3-F | 11.00% | $\Delta\varepsilon$ [1 kHz, 20° C.]: | 4.2 |
| CCQU-5-F | 9.00% | $\varepsilon_\perp$ [1 kHz, 20° C.]: | 3.2 |
| CCZC-3-3 | 3.00% | | |
| CCZC-4-5 | 3.00% | | |
| CCZPC-3-5 | 3.00% | | |
| CC-3-O1 | 11.00% | | |
| CP-3-O1 | 12.00% | | |
| CC-3-V1 | 6.00% | | |
| CCP-V-1 | 10.00% | | |
| CC-5-V | 9.00% | | |
| Σ | 100.00% | | |

Reference Example 8

A liquid-crystal host mixture H-8 is prepared and characterized with respect to its general physical properties, having the composition and properties as indicated in the following table.

| | | | |
|---|---|---|---|
| CC(CN)-4-7 | 14.00% | clearing point [° C.]: | 114.6 |
| CC(CN)-5-5 | 14.00% | $\Delta n$ [589 nm, 20° C.]: | 0.045 |
| CC(CN)-3-3 | 6.00% | $n_e$ [589 nm, 20° C.]: | 1.52 |
| CCZC-3-3 | 3.00% | $\Delta\varepsilon$ [1 kHz, 20° C.]: | −5.2 |
| CCZC-3-5 | 3.00% | $\varepsilon_\perp$ [1 kHz, 20° C.]: | 8.5 |
| CCZC-4-3 | 3.00% | | |
| CCZC-4-5 | 3.00% | | |
| CC-3-O1 | 11.00% | | |
| CC-5-O1 | 4.00% | | |
| CC-5-O2 | 4.00% | | |
| CC(CN)C-3-5 | 10.00% | | |
| CC(CN)C-5-5 | 12.00% | | |
| CC(CN)C-5-3 | 10.00% | | |
| CCZPC-3-3 | 3.00% | | |
| Σ | 100.00% | | |

Reference Example 9

A liquid-crystal host mixture H-9 is prepared and characterized with respect to its general physical properties, having the composition and properties as indicated in the following table.

| | | | |
|---|---|---|---|
| PGIGI-3-F | 10.00% | clearing point [° C.]: | 105 |
| CPG-2-F | 6.00% | $\Delta n$ [589 nm, 20° C.]: | 0.160 |
| CPG-3-F | 7.00% | $n_e$ [589 nm, 20° C.]: | 1.66 |
| CPG-5-F | 5.00% | $\Delta\varepsilon$ [1 kHz, 20° C.]: | 11.4 |
| CPU-5-F | 10.00% | $\varepsilon_\perp$ [1 kHz, 20° C.]: | 4.3 |
| CPG-7-F | 10.00% | | |
| PGU-3-F | 4.00% | | |
| PGU-5-F | 7.00% | | |
| CCGU-3-F | 8.00% | | |
| CPP-3-2 | 4.00% | | |
| CBC-33F | 3.00% | | |
| CBC-53F | 3.00% | | |
| CBC-55F | 3.00% | | |
| CPGU-3-OT | 5.00% | | |
| CP-5-N | 15.00% | | |
| Σ | 100.00% | | |

Reference Example 10

A liquid-crystal host mixture H-10 is prepared and characterized with respect to its general physical properties, having the composition and properties as indicated in the following table.

| | | | |
|---|---|---|---|
| CP-5-N | 15.00% | clearing point [° C.]: | 92 |
| CP-7-N | 14.00% | $\Delta n$ [589 nm, 20° C.]: | 0.163 |
| CPG-2-F | 6.00% | $n_e$ [589 nm, 20° C.]: | 1.67 |
| CPG-3-F | 6.00% | | |
| CPG-5-F | 5.00% | | |
| PGU-2-F | 9.00% | | |
| PGU-3-F | 9.00% | | |
| PGU-5-F | 9.00% | | |
| CPP-3-2 | 7.00% | | |
| CBC-33F | 3.00% | | |
| CBC-53F | 3.00% | | |
| CBC-55F | 3.00% | | |
| CBC-33 | 4.00% | | |
| PGIGI-3-F | 7.00% | | |
| Σ | 100.00% | | |

Reference Example 11

A liquid-crystal base mixture B-11 is prepared and characterized with respect to its general physical properties, having the composition and properties as indicated in the following table.

| | | | |
|---|---|---|---|
| CP-1V-N | 10.00% | clearing point [° C.]: | 113 |
| PZG-3-N | 4.00% | Δn [589 nm, 20° C.]: | 0.297 |
| PZG-4-N | 13.00% | $n_e$ [589 nm, 20° C.]: | 1.82 |
| PTP-1-O2 | 4.00% | Δε [1 kHz, 20° C.]: | 13.6 |
| PTP-2-O1 | 5.00% | $ε_⊥$ [1 kHz, 20° C.]: | 4.5 |
| PTP-3-O1 | 5.00% | | |
| CPTP-3-O1 | 4.00% | | |
| PPTUI-3-2 | 20.00% | | |
| PPTUI-3-4 | 35.00% | | |
| Σ | 100.00% | | |

A mixture H-11 is prepared by mixing 98.41% of mixture B-11 with 1.59% of the compound of formula R-5011 as described in Table F above.

Examples 5 to 14

Mixtures M-5 to M-14 are prepared analogous to mixture M-1 described in Example 1, wherein instead of host mixture H-1 respectively H-2 to H-11 are used as the host mixtures.

The mixtures M-5 to M-14 are treated and analysed analogous to M-1 described in Example 1 above. The mixtures are suitable for the use in devices for regulating the passage of energy from an outside space into an inside space, for example in windows.

The invention claimed is:
1. A mesogenic medium comprising one or more compounds selected from the group of compounds of formulae Ia, Ib and Ic

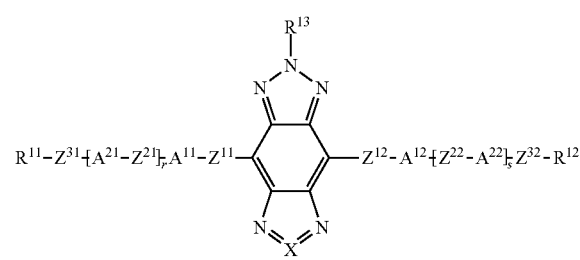
Ia

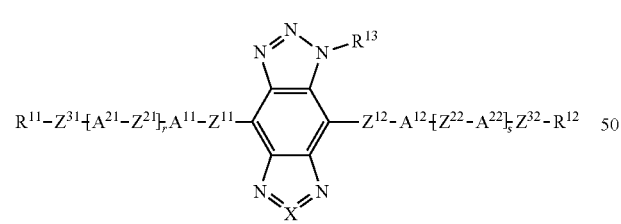
Ib

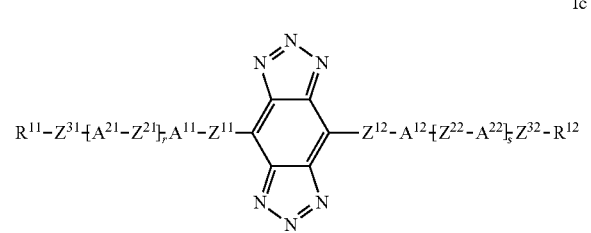
Ic wherein
$R^{11}$, $R^{12}$, $R^{13}$ identically or differently, denote H, F, CN, CO, $N(R^z)_2$, $SO_2R^z$,

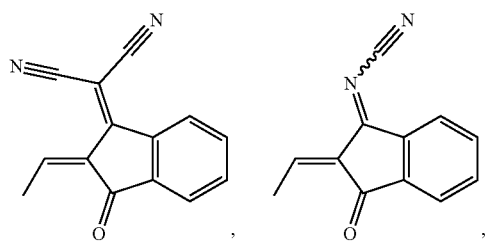

$CH=C(CN)_2$, or a straight-chain alkyl having 1 to 20 C atoms, or branched or cyclic alkyl having 3 to 20 C atoms, in which one or more non-adjacent $CH_2$ groups may each be replaced, independently of one another, by $—C(R^z)=C(R^z)—$, $—C≡C—$,

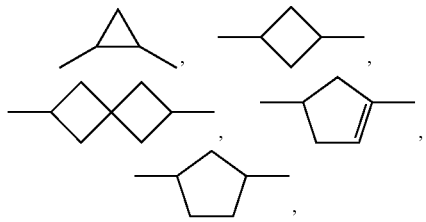

$—N(R^z)—$, $—O—$, $—S—$, $—CO—$, $—CO—O—$, $—O—CO—$ or $—O—CO—O—$ in such a way that O and/or S atoms are not linked directly to one another, and in which one or more H atoms may be replaced by F, Cl, Br, I or CN,
$R^z$ on each occurrence, identically or differently, denotes H, halogen, a straight-chain alkyl having 1 to 12 C atoms, or branched or cyclic alkyl having 3 to 12 C atoms, in which one or more non-adjacent $CH_2$ groups may be replaced by $—O$, $S$, $CO$, $CO\ O—$, $—O—CO—$ or $—O—CO—O—$ in such a way that O and/or S atoms are not linked directly to one another, and in which one or more H atoms may be replaced by F or Cl,
$A^{11}$, $A^{12}$ each, independently of one another, denote an aryl or heteroaryl group, which may be substituted by one or more radicals L,
$A^{21}$, $A^{22}$ on each occurrence, identically or differently, denote an aryl or heteroaryl group, which may be substituted by one or more radicals L, or a cyclic alkyl group having 3 to 10 C atoms, in which one or more non-adjacent $CH_2$ groups may be replaced by O,
L on each occurrence, identically or differently, denotes F, Cl, CN, OH, SCN, $SF_5$ or a straight-chain, in each case optionally fluorinated, alkyl, alkoxy, alkylcarbonyl, alkoxycarbonyl, alkylcarbonyloxy or alkoxycarbonyloxy having 1 to 12 C atoms, or a branched, in each case optionally fluorinated, alkyl, alkoxy, alkylcarbonyl, alkoxycarbonyl, alkylcarbonyloxy or alkoxycarbonyloxy having 3 to 12 C atoms,
X is S, Se or Te,
$Z^{11}$, $Z^{12}$ on each occurrence, identically or differently, denote a single bond, $—CR^{x1}=CR^{x2}—$, $—C(O)—$, $—CR^{x1}=CR^{x2}—CO—$, $—CO—CR^{x1}=CR^{x2}—$, $—CR^{x1}=CR^{x2}—COO—$, $—OCO—CR^{x1}=CR^{x2}—$ or $—N=N—$,
$Z^{21}$, $Z^{22}$ on each occurrence, identically or differently, denote a single bond, $—O—$, $—S—$, $—C(O)—$, $—CR^{y1}R^{y2}—$, $—CF_2O—$, $—OCF_2—$, $—C(O)—O—$, $—O—C(O)—$, $—O—C(O)—O—$, $—OCH_2—$, $—CH_2O—$, $—SCH_2—$, $—CH_2S—$, $—CF_2S—$, —SCF$_2$—, —(CH$_2$)$_{n1}$—, —CF$_2$CH$_2$—, —CH$_2$CF$_2$—, —(CF$_2$)$_{n1}$—, —CR$^{x1}$=CR$^{x2}$—, —CR$^{x1}$=CR$^{x2}$—CO—, —CO—CR$^{x1}$=CR$^{x2}$—, —CR$^{x1}$=CR$^{x2}$—COO—, —OCO—CR$^{x1}$=CR$^{x2}$— or —N=N—, Z$^{31}$, Z$^{32}$ on each occurrence, identically or differently, denote a single bond, —O—, —CF$_2$O—, —OCF$_2$—, —CF$_2$—, —CF$_2$CF$_2$— or —C(O)—, R$^{x1}$, R$^{x2}$ independently of one another, denote H, F, Cl, CN or alkyl having 1 to 12 C atoms, R$^{y1}$ denotes H or alkyl having 1 to 12 C atoms, R$^{y2}$ denotes alkyl having 1 to 12 C atoms, n1 denotes 1, 2, 3 or 4, and r, s independently of one another, denote 0, 1, 2 or 3.

2. The mesogenic medium according to claim 1, wherein A$^{11}$ and A$^{12}$ denote, independently of one another, 1,4-phenylene, 1,4-naphthylene, 2,6-naphthylene, thiazole-2,5-diyl, thiophene-2,5-diyl or thienothiophene-2,5-diyl, wherein one or more H atoms may be replaced by the group L.

3. The mesogenic medium according to claim 1, wherein Z$^{11}$ and Z$^{12}$ denote a single bond.

4. The mesogenic medium according to claim 1, wherein the medium additionally comprises one or more compounds selected from the group of compounds of formulae CY, PY and AC

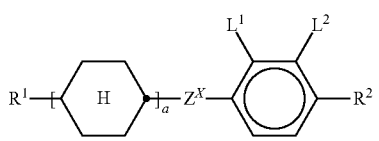
CY

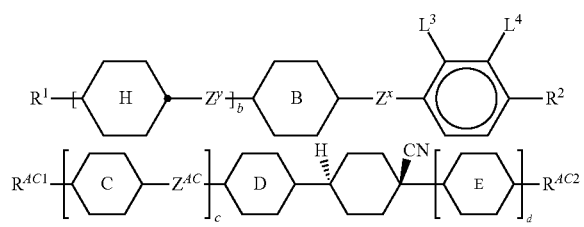
PY

AC
wherein

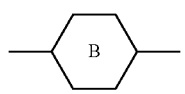
denotes

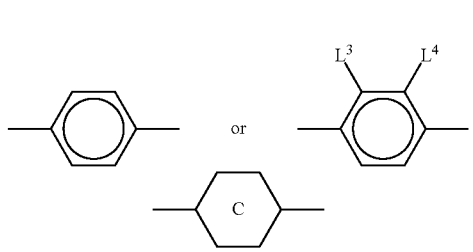

and

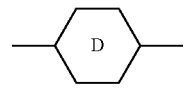
denote denotes

R$^1$, R$^2$, R$^{AC1}$, R$^{AC2}$ each, independently of one another, denote alkyl having 1 to 12 C atoms, where one or two non-adjacent CH$_2$ groups may be replaced by —O—, —CH=CH—, —CO—, —OCO—, or —COO— in such a way that O atoms are not linked directly to one another, Z$^x$, Z$^y$, Z$^{AC}$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, L$^1$, L$^2$, L$^3$, L$^4$ each, independently of one another, denote F, Cl, CN, OCF$_3$, CF$_3$, CH$_3$, CH$_2$F, or CHF$_2$, a is 1 or 2, b is 0 or 1, c is 0, 1 or 2, and d is 0 or 1.

5. The mesogenic medium according to claim 1, wherein the medium additionally comprises one or more compounds selected from the group of compounds of formulae II to VIII II
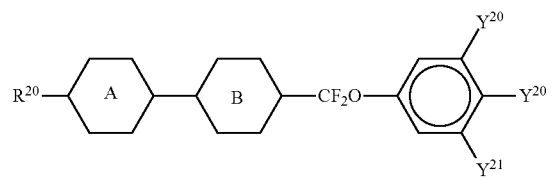

III
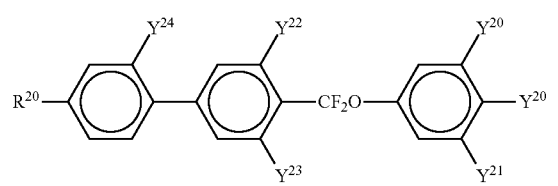

IV
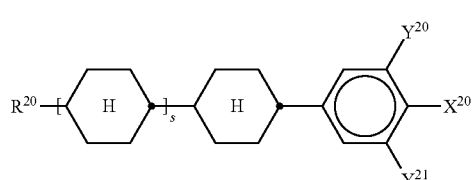

V
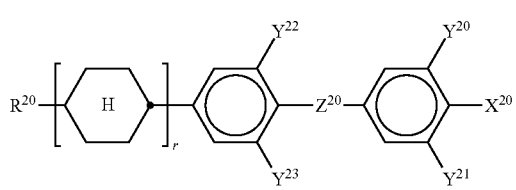

VI
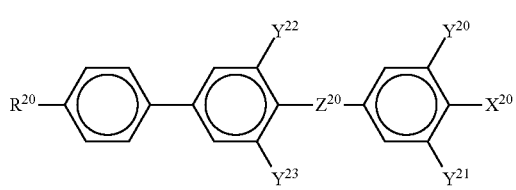

VII
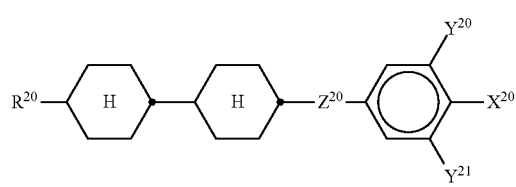

VIII
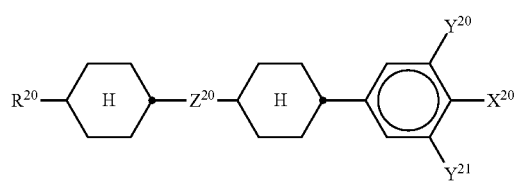

wherein

 and 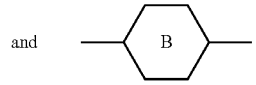

each, independently of one another, denote

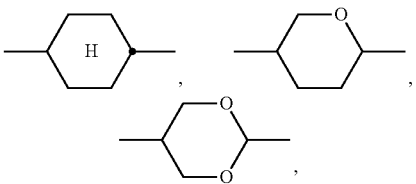

$R^{20}$ identically or differently, denotes a halogenated or unsubstituted alkyl or alkoxy radical having 1 to 15 C atoms, where one or more $CH_2$ groups in these radicals may each be replaced, independently of one another, by —C≡C—, —$CF_2$O—, —CH=CH—,

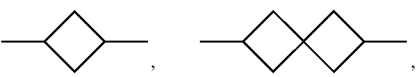

—O—, —CO—O— or —O—CO— in such a way that O atoms are not linked directly to one another, $X^{20}$ identically or differently, denotes F, Cl, CN, $SF_5$, SCN, NCS, a halogenated alkyl radical, a halogenated alkenyl radical, a halogenated alkoxy radical or a halogenated alkenyloxy radical, each having 1 to 6 C atoms, $Y^{20}$, $Y^{21}$, $Y^{22}$, $Y^{23}$, $Y^{24}$ each, identically or differently, denote H or F, $Z^{20}$ denotes —$C_2H_4$—, —$(CH_2)_4$—, —CH=CH—, —CF=CF—, —$C_2F_4$—, —$CH_2CF_2$—, —$CF_2CH_2$—, —$CH_2O$—, —$OCH_2$—, —COO— or —$OCF_2$—, in formulae V and VI also a single bond, in formulae V and VIII also —$CF_2O$—, r denotes 0 or 1, and s denotes 0 or 1.

6. The mesogenic medium according to claim 1, wherein the medium additionally comprises one or more compounds selected from the group of compounds of formulae DK and O DK

O

wherein $R^5$, $R^6$, $R^{O1}$ and $R^{O2}$ each, independently of one another, denote alkyl having 1 to 12 C atoms, where one or two non-adjacent $CH_2$ groups may be replaced by —O—, —CH=CH—, —CO—, —OCO—, or —COO— in such a way that O atoms are not linked directly to one another,

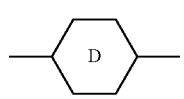

denotes

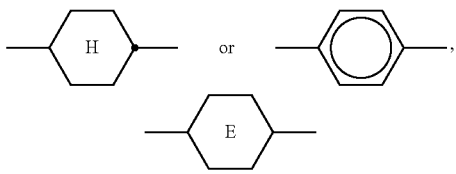

denotes

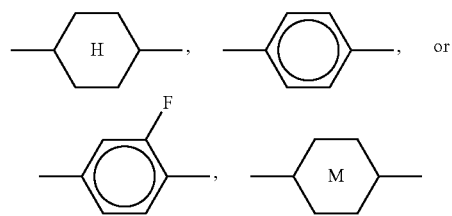

denotes

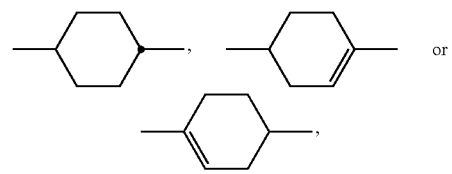

and

denotes

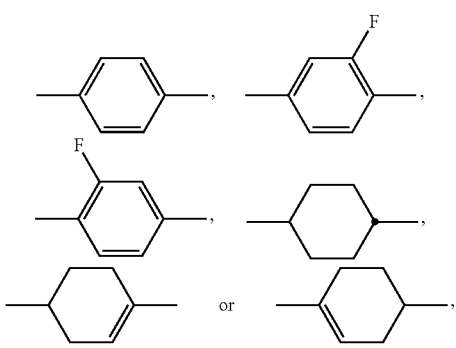

$Z^{O1}$ denotes —CH$_2$CH$_2$—, —CF$_2$CF$_2$—, —C≡C— or a single bond,
$Z^{O2}$ denotes CH$_2$O, —C(O)O—, —CH$_2$CH$_2$—, —CF$_2$CF$_2$—, or a single bond,
o is 1 or 2, and
e is 1 or 2.

7. The mesogenic medium according to claim 1, wherein the medium additionally comprises one or more compounds selected from the group of compounds of formulae O3 to O5

O3
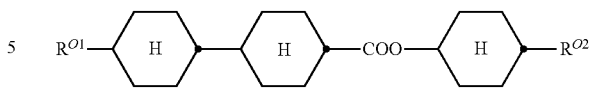

O4
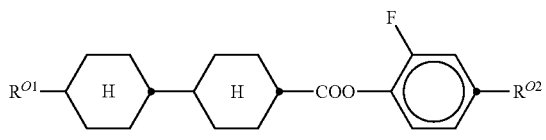

O5
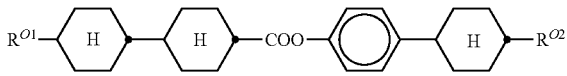

wherein $R^{O1}$ and $R^{O2}$, identically or differently, denote straight-chain alkyl having 1 to 6 C atoms or straight-chain alkenyl having 2 to 6 C atoms.

8. The mesogenic medium according to claim 1, wherein the medium additionally comprises one or more compounds selected from the group of compounds of formulae DK1 to DK12:

DK1
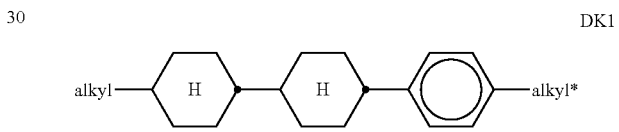

DK2

DK3
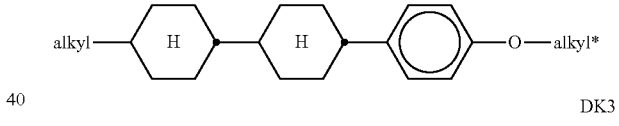

DK4
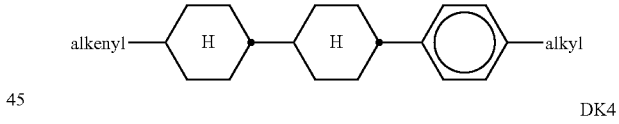

DK5
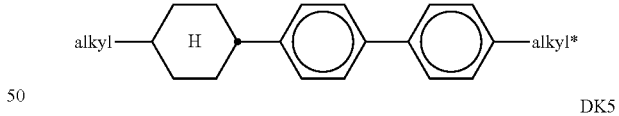

DK6
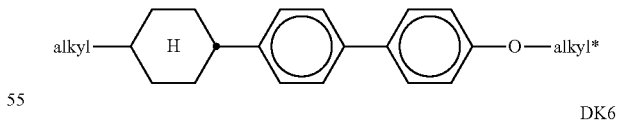

DK7
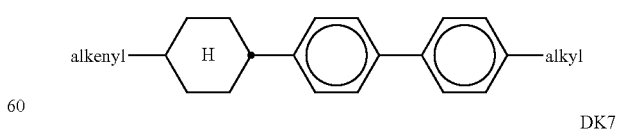

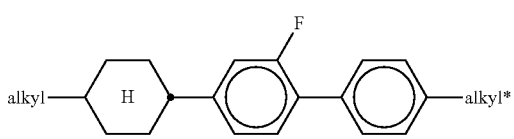

-continued

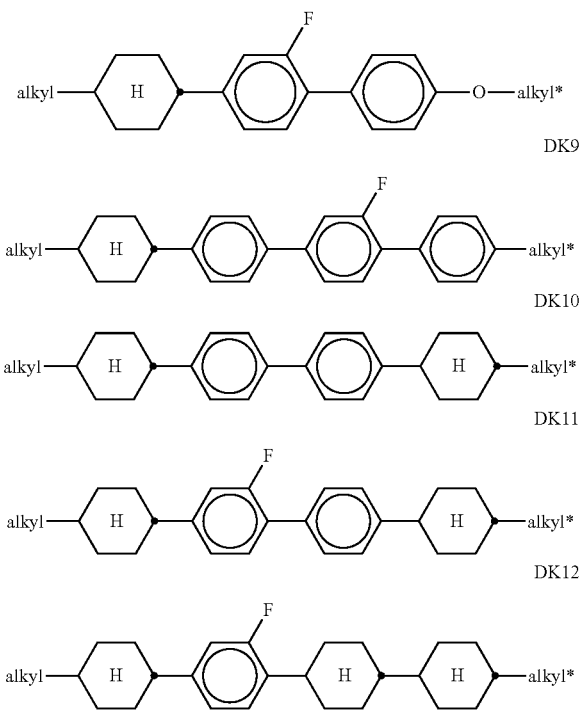

in which alkyl and alkyl* each, independently of one another, denote a straight-chain alkyl radical having 1 to 6 C atoms, and alkenyl denotes a straight-chain alkenyl radical having 2 to 6 C atoms.

9. A device for regulating the passage of energy from an outside space into an inside space, wherein the device contains a switching layer comprising the mesogenic medium according to claim 1.

10. A window comprising the device according to claim 9.

11. An electro-optical display, a device for regulating the passage of energy from an outside space into an inside space, an electrical semiconductor, an organic field-effect transistor, a printed circuit, a radio frequency identification element, an organic light-emitting diode, a lighting element, a photovoltaic device, an optical sensor, an effect pigment, a decorative element or as a dye for colouring polymers, comprising the mesogenic medium according to claim 1.

12. A mesogenic medium comprising one or more compounds of formula Ia

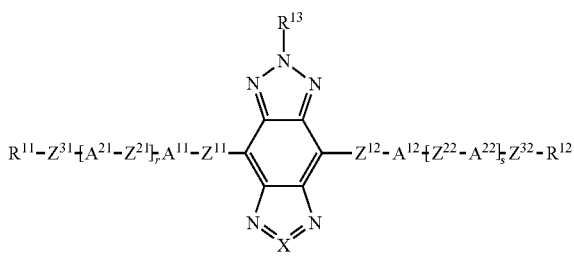

Ia wherein
$R^{11}$, $R^{12}$, $R^{13}$ identically or differently, denote H, F, CN, CO, $N(R^z)_2$, $SO_2R^z$,

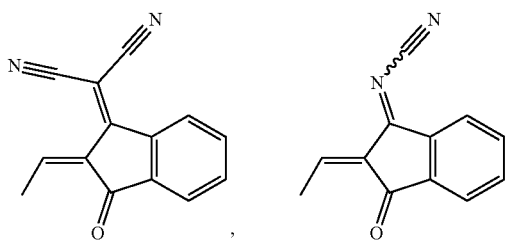

$CH=C(CN)_2$, or a straight-chain alkyl having 1 to 20 C atoms, or branched or cyclic alkyl having 3 to 20 C atoms, in which one or more non-adjacent $CH_2$ groups may each be replaced, independently of one another, by $—C(R^z)=C(R^z)—$, $—C\equiv C—$,

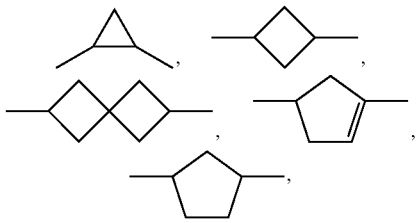

$—N(R^z)—$, $—O—$, $—S—$, $—CO—$, $—CO—O—$, $—O—CO—$ or $—O—CO—O—$ in such a way that O and/or S atoms are not linked directly to one another, and in which one or more H atoms may be replaced by F, Cl, Br, I or CN, wherein at least one of $R^{11}$, $R^{12}$ and $R^{13}$ is

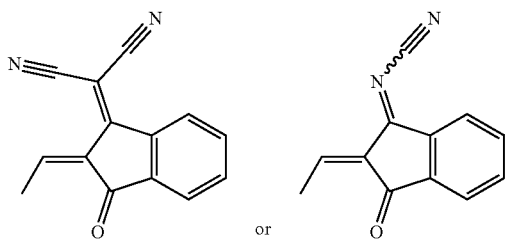

or , $R^z$ on each occurrence, identically or differently, denotes H, halogen, a straight-chain alkyl having 1 to 12 C atoms, or branched or cyclic alkyl having 3 to 12 C atoms, in which one or more non-adjacent $CH_2$ groups may be replaced by $—O$, $S$, $CO$, $CO$ $O—$, $—O—CO—$ or $—O—CO—O—$ in such a way that O and/or S atoms are not linked directly to one another, and in which one or more H atoms may be replaced by F or Cl, $A^{11}$, $A^{12}$ each, independently of one another, denote an aryl or heteroaryl group, which may be substituted by one or more radicals L, $A^{21}$, $A^{22}$ on each occurrence, identically or differently, denote an aryl or heteroaryl group, which may be substituted by one or more radicals L, or a cyclic alkyl group having 3 to 10 C atoms, in which one or more non-adjacent $CH_2$ groups may be replaced by O, L on each occurrence, identically or differently, denotes F, Cl, CN, OH, SCN, $SF_5$ or a straight-chain, in each case optionally fluorinated, alkyl, alkoxy, alkylcarbonyl, alkoxycarbonyl, alkylcarbonyloxy or alkoxycarbonyloxy having 1 to 12 C atoms, or a branched, in each case optionally fluorinated, alkyl, alkoxy, alkylcarbonyl, alkoxycarbonyl, alkylcarbonyloxy or alkoxycarbonyloxy having 3 to 12 C atoms, X is S, Se or Te, $Z^{11}$, $Z^{12}$ on each occurrence, identically or differently, denote a single bond, —$CR^{x1}$=$CR^{x2}$—, —C(O)—, —$CR^{x1}$=$CR^{x2}$—CO—, —CO—$CR^{x1}$=$CR^{x2}$—, —$CR^{x1}$=$CR^{x2}$—COO—, —OCO—$CR^{x1}$=$CR^{x2}$— or —N=N—, $Z^{21}$, $Z^{22}$ on each occurrence, identically or differently, denote a single bond, —O—, —S—, —C(O)—, —$CR^{y1}R^{y2}$—, —$CF_2O$—, —$OCF_2$—, —C(O)—O—, —O—C(O)—, —O—C(O)—O—, —$OCH_2$—, —$CH_2O$—, —$SCH_2$—, —$CH_2S$—, —$CF_2S$—, —$SCF_2$—, —$(CH_2)_{n1}$—, —$CF_2CH_2$—, —$CH_2CF_2$—, —$(CF_2)_{n1}$—, —$CR^{x1}$=$CR^{x2}$—, —C≡C—, —$CR^{x1}$=$CR^{x2}$—CO—, —CO—$CR^{x1}$=$CR^{x2}$—, —$CR^{x1}$=$CR^{x2}$—COO—, —OCO—$CR^{x1}$=$CR^{x2}$— or —N=N—, $Z^{31}$, $Z^{32}$ on each occurrence, identically or differently, denote a single bond, —O—, —$CF_2O$—, —$OCF_2$—, —$CF_2$—, —$CF_2CF_2$— or —C(O)—, $R^{x1}$, $R^{x2}$ independently of one another, denote H, F, Cl, CN or alkyl having 1 to 12 C atoms, $R^{y1}$ denotes H or alkyl having 1 to 12 C atoms, $R^{y2}$ denotes alkyl having 1 to 12 C atoms, n1 denotes 1, 2, 3 or 4, and r, s independently of one another, denote 0, 1, 2 or 3.

13. The mesogenic medium according to claim 12, wherein $A^{11}$ and $A^{12}$ denote, independently of one another, 1,4-phenylene, 1,4-naphthylene, 2,6-naphthylene, thiazole-2,5-diyl, thiophene-2,5-diyl or thienothiophene-2,5-diyl, wherein one or more H atoms may be replaced by the group L.

14. The mesogenic medium according to claim 12, wherein $Z^{11}$ and $Z^{12}$ denote a single bond.

15. The mesogenic medium according to claim 12, wherein the medium additionally comprises one or more compounds selected from the group of compounds of formulae CY, PY and AC

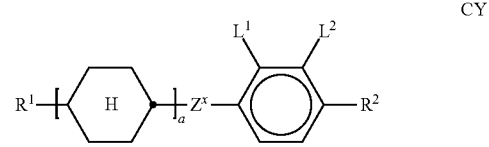

CY

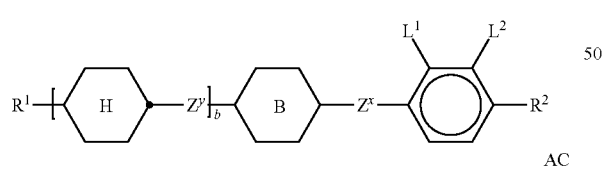

PY

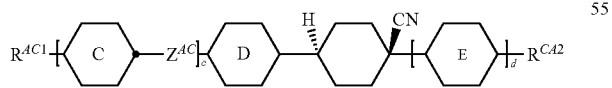

AC wherein

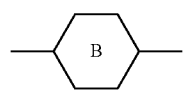

denotes

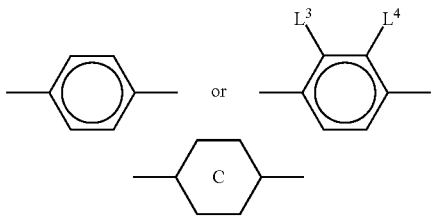

and

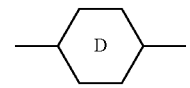

denote

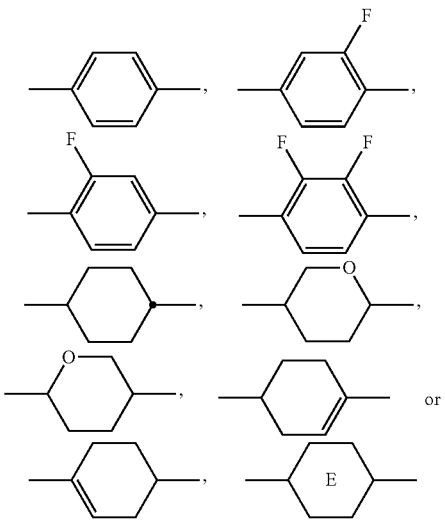

denotes $R^1$, $R^2$ $R^{AC1}$, $R^{AC2}$ each, independently of one another, denote alkyl having 1 to 12 C atoms, where one or two non-adjacent $CH_2$ groups may be replaced by —O—, —CH=CH—, —CO—, —OCO—, or —COO— in such a way that O atoms are not linked directly to one another, $Z_x$, $Z^y$, $Z^{AC}$ each, independently of one another, denote —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond, L¹, L², L³, L⁴ each, independently of one another, denote
F, Cl, CN, OCF₃, CF₃, CH₃, CH₂F, or CHF₂,
a is 1 or 2,
b is 0 or 1,
c is 0, 1 or 2, and
d is 0 or 1.

16. The mesogenic medium according to claim 12, wherein the medium additionally comprises one or more compounds selected from the group of compounds of formulae II to VIII

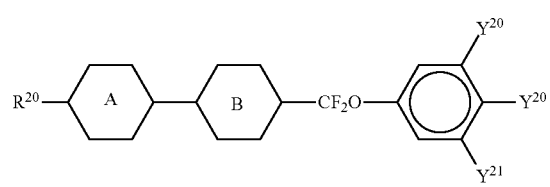
II

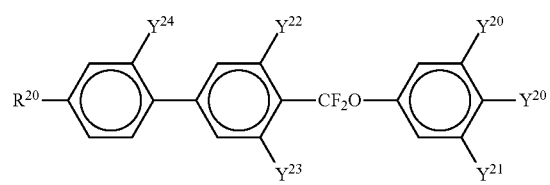
III

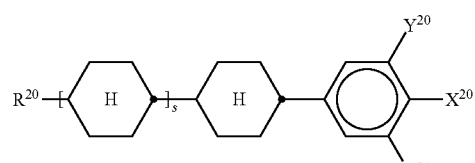
IV

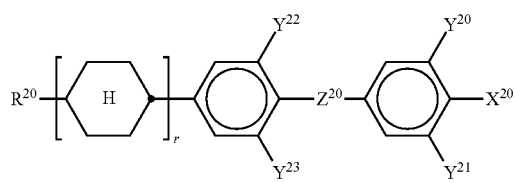
V

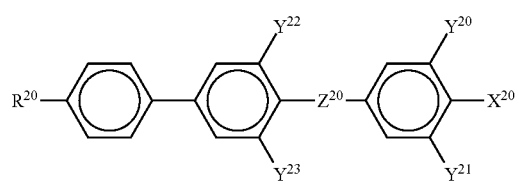
VI

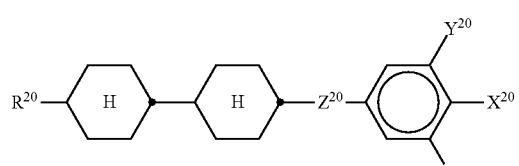
VII

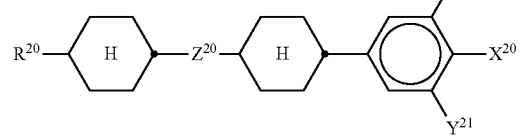
VIII wherein

each, independently of one another, denote

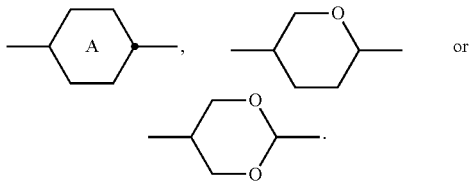

$R^{20}$ identically or differently, denotes a halogenated or unsubstituted alkyl or alkoxy radical having 1 to 15 C atoms, where one or more CH₂ groups in these radicals may each be replaced, independently of one another, by —C≡C—, —CF₂O—, —CH=CH—,

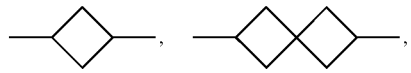

—O—, —CO—O— or —O—CO— in such a way that O atoms are not linked directly to one another,
$X^{20}$ identically or differently, denotes F, Cl, CN, SF₅, SCN, NCS, a halogenated alkyl radical, a halogenated alkenyl radical, a halogenated alkoxy radical or a halogenated alkenyloxy radical, each having 1 to 6 C atoms,
$Y^{20}$, $Y^{21}$, $Y^{22}$, $Y^{23}$, $Y^{24}$ each, identically or differently, denote H or F,
$Z^{20}$ denotes —C₂H₄—, —(CH₂)₄—, —CH=CH—, —CF=CF—, —C₂F₄—, —CH₂CF₂—, —CF₂CH₂—, —CH₂O—, —OCH₂—, —COO— or —OCF₂—, in formulae V and VI also a single bond, in formulae V and VIII also —CF₂O—,
r denotes 0 or 1, and
s denotes 0 or 1.

17. The mesogenic medium according to claim 12, wherein the medium additionally comprises one or more compounds selected from the group of compounds of formulae DK and O

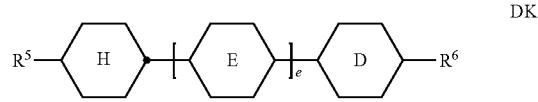
DK

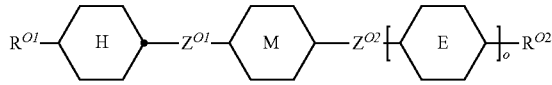
O wherein $R^5$, $R^6$, $R^{O1}$ and $R^{O2}$ each, independently of one another, denote alkyl having 1 to 12 C atoms, where one or two non-adjacent CH₂ groups may be replaced by —O—, —CH=CH—, —CO—, —OCO—, or —COO— in such a way that O atoms are not linked directly to one another,

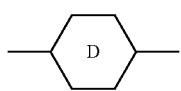

denotes

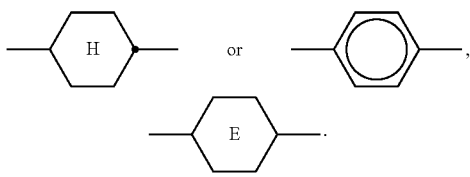

denotes

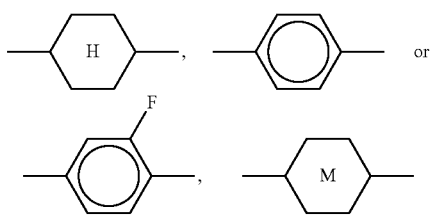

denotes

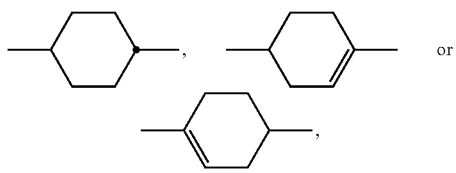

and

denotes

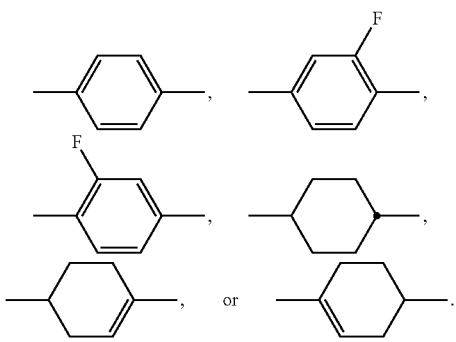

$Z^{O1}$ denotes —CH$_2$CH$_2$—, —CF$_2$CF$_2$—, —C≡C— or a single bond, $Z^{O2}$ denotes CH$_2$O, —C(O)O—, —CH$_2$CH$_2$—, —CF$_2$CF$_2$—, or a single bond, o is 1 or 2, and e is 1 or 2.

18. The mesogenic medium according to claim 12, wherein the medium additionally comprises one or more compounds selected from the group of compounds of formulae O3 to O5

O3

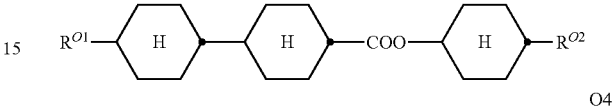

O4

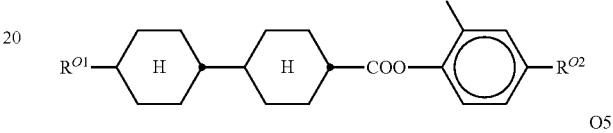

O5

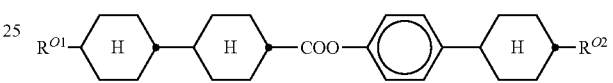

wherein $R^{O1}$ and $R^{O2}$, identically or differently, denote straight-chain alkyl having 1 to 6 C atoms or straight-chain alkenyl having 2 to 6 C atoms.

19. The mesogenic medium according to claim 12, wherein the medium additionally comprises one or more compounds selected from the group of compounds of formulae DK1 to DK12:

DK1

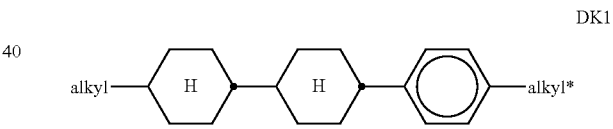

DK2

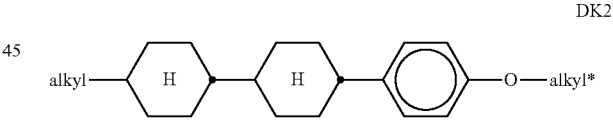

DK3

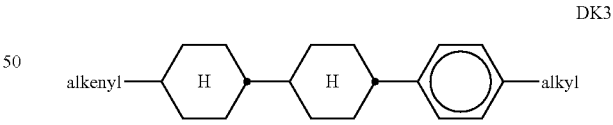

DK4

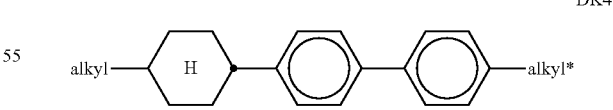

DK5

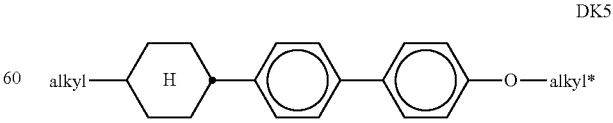

DK6

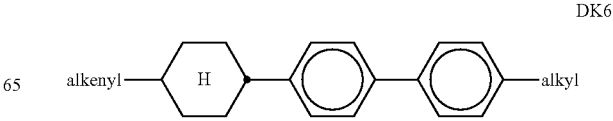

-continued

DK7

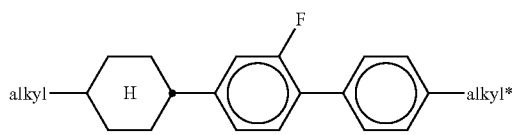

DK8

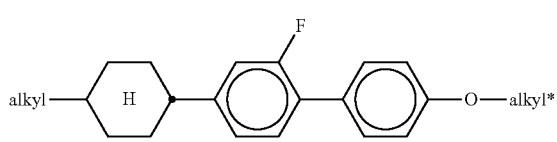

DK9

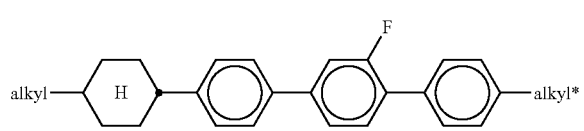

DK10

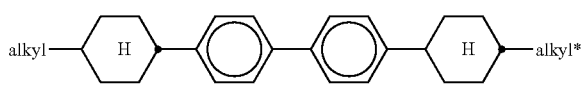

DK11

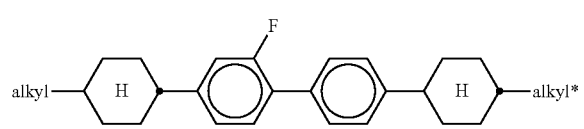

DK12

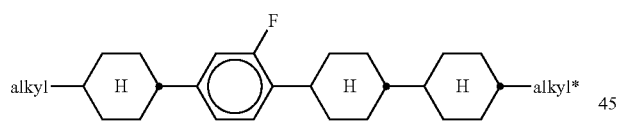

in which alkyl and alkyl* each, independently of one another, denote a straight-chain alkyl radical having 1 to 6 C atoms, and alkenyl denotes a straight-chain alkenyl radical having 2 to 6 C atoms.

20. A device for regulating the passage of energy from an outside space into an inside space, wherein the device contains a switching layer comprising the mesogenic medium according to claim 12.

21. A window comprising the device according to claim 20.

22. An electro-optical display, a device for regulating the passage of energy from an outside space into an inside space, an electrical semiconductor, an organic field-effect transistor, a printed circuit, a radio frequency identification element, an organic light-emitting diode, a lighting element, a photovoltaic device, an optical sensor, an effect pigment, a decorative element or as a dye for colouring polymers, comprising the mesogenic medium according to claim 12.

23. A compound of formula Ia

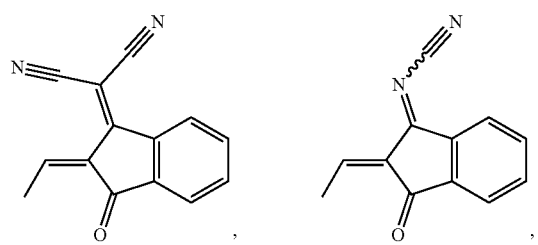 [SMILES: C/C=C1\C(=O)c2ccccc2C1=C(C#N)C#N ; C/C=C1\C(=O)c2ccccc2C1=NC#N]

Ia wherein
$R^{11}$, $R^{12}$, $R^{13}$ identically or differently, denote H, F, CN, CO, $N(R^z)_2$, $SO_2R^z$,

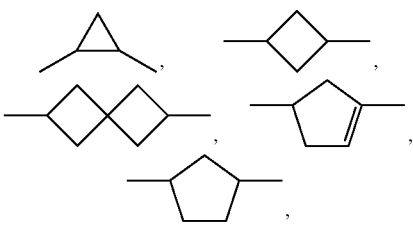

$CH=C(CN)_2$, or a straight-chain alkyl having 1 to 20 C atoms, or branched or cyclic alkyl having 3 to 20 C atoms, in which one or more non-adjacent $CH_2$ groups may each be replaced, independently of one another, by $-C(R^z)=C(R^z)-$, $-C\equiv C-$, —$N(R^z)$—, —O—, —S—, —CO—, —CO—O—, —O—CO— or —O—CO—O— in such a way that O and/or S atoms are not linked directly to one another, and in which one or more H atoms may be replaced by F, Cl, Br, I or CN, wherein at least one of $R^{11}$, $R^{12}$ and $R^{13}$ is

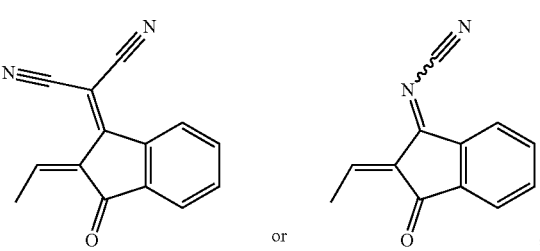

$R^z$ on each occurrence, identically or differently, denotes H, halogen, a straight-chain alkyl having 1 to 12 C atoms, or branched or cyclic alkyl having 3 to 12 C atoms, in which one or more non-adjacent CH$_2$ groups may be replaced by —O—, —S—, —CO—, —CO—O—, —O—CO— or —O—CO—O— in such a way that O and/or S atoms are not linked directly to one another, and in which one or more H atoms may be replaced by F or Cl, A$^{11}$, A$^{12}$ each, independently of one another, denote an aryl or heteroaryl group, which may be substituted by one or more radicals L, A$^{21}$, A$^{22}$ on each occurrence, identically or differently, denote an aryl or heteroaryl group, which may be substituted by one or more radicals L, or a cyclic alkyl group having 3 to 10 C atoms, in which one or more non-adjacent CH$_2$ groups may be replaced by O, L on each occurrence, identically or differently, denotes F, Cl, CN, OH, SCN, SF$_5$ or a straight-chain, in each case optionally fluorinated, alkyl, alkoxy, alkylcarbonyl, alkoxycarbonyl, alkylcarbonyloxy or alkoxycarbonyloxy having 1 to 12 C atoms, or a branched, in each case optionally fluorinated, alkyl, alkoxy, alkylcarbonyl, alkoxycarbonyl, alkylcarbonyloxy or alkoxycarbonyloxy having 3 to 12 C atoms X is S, Se or Te, Z$^{11}$, Z$^{12}$ on each occurrence, identically or differently, denote a single bond, —CR$^{x1}$=CR$^{x2}$—, —C(O)—, —CR$^{x1}$=CR$^{x2}$—CO—, —CO—CR$^{x1}$=CR$^{x2}$—, —CR$^{x1}$=CR$^{x2}$—COO—, —OCO—CR$^{x1}$=CR$^{x2}$— or —N=N—, Z$^{21}$, Z$^{22}$ on each occurrence, identically or differently, denote a single bond, —O—, —S—, —C(O)—, —CR$^{y1}$R$^{y2}$—, —CF$_2$O—, —OCF$_2$—, —C(O)—O—, —O—C(O)—, —O—C(O)—O—, —OCH$_2$—, —CH$_2$O—, —SCH$_2$—, —CH$_2$S—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CR$^{x1}$=CR$^{x2}$—, —CR$^{x1}$=CR$^{x2}$—CO—, —CO—CR$^{x1}$=CR$^{x2}$—, —CR$^{x1}$=CR$^{x2}$—COO—, —OCO—CR$^{x1}$=CR$^{x2}$— or —N=N—, Z$^{31}$, Z$^{32}$ on each occurrence, identically or differently, denote a single bond, —O—, —CF$_2$O—, —OCF$_2$—, —CF$_2$—, —CF$_2$CF$_2$— or —C(O)—, R$^{x1}$, R$^{x2}$ independently of one another, denote H, F, Cl, CN or alkyl having 1 to 12 C atoms, R$^{y1}$ denotes H or alkyl having 1 to 12 C atoms, R$^{y2}$ denotes alkyl having 1 to 12 C atoms, n1 denotes 1, 2, 3 or 4, and r, s independently of one another, denote 0, 1, 2 or 3.

24. The compound according to claim 23, wherein the compound exhibits an absorption maximum at a wavelength of greater than 600 nm.

25. The compound according to claim 23, wherein

X is S,

Z$^{11}$, Z$^{12}$ denote a single bond,

A$^{11}$, A$^{12}$ denote, independently of one another, 1,4-phenylene, thiophene-2,5-diyl or thienothiophene-2,5-diyl, wherein one or more H atoms may be replaced by the group L, and r, s independently of one another, denote 0, 1 or 2.

26. A method for preparing a compound of formula Ia according to claim 23, comprising subjecting a compound of formula I-SM to a chemical reaction

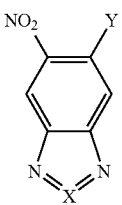

I-SM wherein

X is S, Se or Te, and

Y is NO$_2$ or halogen.

* * * * *